US010633668B2

(12) United States Patent
Kaeppler et al.

(10) Patent No.: US 10,633,668 B2
(45) Date of Patent: Apr. 28, 2020

(54) EXTENDING JUVENILITY IN GRASSES

(71) Applicant: Wisconsin Alumni Research Foundation, Madison, WI (US)

(72) Inventors: Shawn Kaeppler, Oregon, WI (US); Natalia de Leon Gatti, Middleton, WI (US); Jillian Foerster, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 44 days.

(21) Appl. No.: 15/482,588

(22) Filed: Apr. 7, 2017

(65) Prior Publication Data

US 2017/0275643 A1 Sep. 28, 2017

Related U.S. Application Data

(62) Division of application No. 13/834,114, filed on Mar. 15, 2013, now Pat. No. 9,617,558.

(60) Provisional application No. 61/651,540, filed on May 24, 2012.

(51) Int. Cl.
*C12N 15/82* (2006.01)

(52) U.S. Cl.
CPC ..... *C12N 15/8266* (2013.01); *C12N 15/8261* (2013.01)

(58) Field of Classification Search
None
See application file for complete search history.

(56) References Cited

U.S. PATENT DOCUMENTS

2011/0167514 A1* 7/2011 Brover ................. C07K 14/415 800/278

FOREIGN PATENT DOCUMENTS

WO WO 2007117693 A2 * 10/2007

OTHER PUBLICATIONS

Guo et al (2004, Proc. Natl. Acad. Sci. USA 101: 9205-9210). (Year: 2004).*
Zhao et al. (New phytologist 190.4 (2011): 906-915). (Year: 2011).*
Helliwell et al. (Methods in enzymology. vol. 392. Academic Press, 2005. 24-35). (Year: 2005).*
GenBank Accession EU975023, dated Dec. 10, 2008. (Year: 2008).*
Meinkoth et al. (Analytical biochemistry 138.2 (1984): 267-284). (Year: 1984).*
Zhao et al. (New phytologist 190.4 (2011): 906-915)—supplementary data. (Year: 2011).*
Abedon et al., Cell wall composition in juvenile and adult leaves of maize (*Zea mays* L.) *J. of Agriculture and Food Chemistry* 54:3896-3900, 2006.
AT5G55390.1, Locus on *Arabidopsis thaliana* chromosome 5, encoding EDM2, available at <http://www.arabidopsis.org/servlets/TairObject?id=135952&type=gene>, Feb. 4, 2013.
Os08g24946.1, Locus on *Oryza sativa ssp japonica cv. Nipponbare* chromosome 8, encoding EDM2, available at <http://rice.plantbiology.msu.edu/cgi-bin/ORF infopage.cgi?orf=LOC Os08g24946.1>, undated.
Bradi4g27190.1, Gene on *Brachypodium distachyon* chromosome 4, available at <http://plants.ensembl.org/Brachypodium_distachyon/Gene/Summary?db=core;g=BRADI4G27190;r=4:32266132-32280768>, 2013.
Buckler et al., "The genetic architecture of maize flowering time," *Science* 325:714-718, 2009.
Chuck et al., "The heterochronic maize mutant Corngrass1 results from overexpression of a tandem microRNA," *Nature Genetics* 39:544-549, 2007.
Chuck et al., "Overexpression of the maize Corngrass1 microRNA prevents flowering, improves digestibility, and increases starch content of switchgrass," *PNAS* 108:17550-17555, Sep. 3, 2011.
Elshire et al., "A robust, simple genotyping-by-sequencing (GBS) approach for high diversity species," *PLoS ONE* 6(5):e19379, May 2011.
Evans et al., "Heterochronic effects of glossy15 mutations on epidermal cell identity in maize," *Devel.* 120:1971-1981, Jul. 1, 1994.
Flint-Garcia et al., "Maize association population: a high-resolution platform for quantitative trait locus dissection," *Plant J* 44(6):1054-64, 2005.
Hansey et al., "Cell wall composition and ruminant digestibility of various maize tissues across development," *Bioenergy Res.* 3:28-37, 2010.
Hansey et al., "Maize (*Zea mays* L.) Genome diversity as revealed by RNA-sequencing," *PLOS ONE* 7(3):e33071, Oct. 31, 2011.
Lee et al., "Expanding the genetic map of maize with the intermated B73xMo17 (IBM) population," *Plant Mol Biol* 48(5-6): 453-61, 2002.
Moose et al., "Glossy15, an APETALA2-like gene from maize that regulates leaf epidermal cell identity," Genes *Dev.* 10:3018-3027, 1996.

(Continued)

*Primary Examiner* — Charles Logsdon
(74) *Attorney, Agent, or Firm* — Dentons US LLP

(57) ABSTRACT

The present invention relates to compositions and methods for modulating the juvenile to adult developmental growth transition in plants, such as grasses (e.g. maize). In particular, the invention provides methods for enhancing agronomic properties in plants by modulating expression of GRMZM2G362718, GRMZM2G096016, or homologs thereof. Modulation of expression of one or more additional genes which affect juvenile to adult developmental growth transition such as Glossy15 or Cg1, in conjunction with such modulation of expression is also contemplated. Nucleic acid constructs for down-regulation of GRMZM2G362718 and/or GRMZM2G096016 are also contemplated, as are transgenic plants and products produced there from, that demonstrate altered, such as extended juvenile growth, and display associated phenotypes such as enhanced yield, improved digestibility, and increased disease resistance. Plants described herein may be used, for example, as improved forage or feed crops or in biofuel production.

33 Claims, 12 Drawing Sheets

Specification includes a Sequence Listing.

(56) References Cited

OTHER PUBLICATIONS

Nonogaki, "MicroRNA gene regulation cascades during early stages of plant development," *Plant Cell Physiol.* 51(11):1840-1846, 2010.

Peragine et al., "SGS3 and SGS2/SDE1/RDR6 are required for juvenile development and the production of trans-acting siRNAs in *Arabidopsis," Genes Devel.* 18(19):2368-2379, Oct. 1, 2004.

Riedeman et al., "Divergent recurrent selection for vegetative phase change and effects on agronomic traits and corn borer resistance," *Crop Sci.* 48:1723-1731, 2008.

Schnable et al., "The B73 maize genome: complexity, diversity, and dynamics," *Science* 326:1112, Nov. 20, 2009.

Sekhon et al., "Genome-wide atlas of transcription during maize development," *Plant J.* 66:553-563, May 2011.

Tsuchiya et al., "The *Arabidopsis* defense component EDM2 affects the floral transition in an FLC-dependent manner," *Plant J.* 62:518-528, 2010.

Willmann et al., "Time to Grow up: the Temporal Role of small RNAs in Plants," *Curr. Opin. Plant Biol.* 8:548-552, 2005.

Willmann et al., "The effect of the floral repressor FLC on the timing and progression of vegetative phase change in *Arabidopsis," Devel.* 138:677-685, Feb. 15, 2011.

Tsuchiya et al., "Mutations in EDM2 selectively affect silencing states of transposons and induce plant developmental plasticity," *Scientific Reports* 3:1701, 2013.

Guo et al., "Protein tolerance to random amino acid change," *PNAS* 101(25):9205-9210, 2004.

Accession No. Sb02g003420.1, Predicted protein sequence of Sb02g003420.1 from Sorghum bicolor, accessed on Nov. 25, 2013.

GenBank GQ905502.1, *Zea mays* clone zma-miR156c/b precursor miRNA zma-miR156c/b, precursor RNA, complete sequence, accessed on Nov. 25, 2013.

GenBank EU975023.1, *Zea mays* clone 465284 nuclear transcription factor Y subunit A-10 mRNA, complete coding sequence, accessed on Nov. 25, 2013.

* cited by examiner

FIG. 2

```
AT5G55390.1              MTFVDDDEEEDFSVPQSASNYYFEDDDKEPVSFARLPIQWSVEEKVDGS-GLGFYLRGRS
GRMZM2G362718_P01        --MFDDDDGVDPQIEDVNRYYFEDGEEKPVCFSILPFQFGEDDSEAVFLRKDVFLCGFV
                           :.***::      :....***** :::**.*: **:*:. ::.        .:* *

AT5G55390.1              DNGLLPLHKLVKAWRYDLSNFQPEISVLTKDNIWIKLEEPRKSYGELIRTVLVTLHSIQF
GRMZM2G362718_P01        -DKNLPVYKEVVAWKIRLDSEHPNIYVLSIEHKWIKLLKPRKCYGDIVRSTLITVQMLHF
                          :  **::* * **:  *.. :*:* **: :. **** :***.**:::*:.*:*:: ::*

AT5G55390.1              LRRNPQASEKALWEKLTRSLRSYDVKPSQNDLVDHIGLIAEAAKRDRNLANSKFILAFLT
GRMZM2G362718_P01        FGRGEQRSSNHLWDHLDEVFGKYNPKPVEDDLMKHHTLIKLFVEKDQTLMKSKILQRLIE
                         : *  * *.: **::* . : .*: ** ::**:.*  **   .::*:.* :**::  ::

AT5G55390.1              KKPTK--RRLP----------------DEDNAKDDFIVGDEDTYVASDEDELDDEDDDFF
GRMZM2G362718_P01        NGFKRTKKALGMEAQSIVSDGWRARKNDDNNYGNKDDSGDDCDGDGSSDDGDGSSDDDVT
                         :  .:  : *                 *::*  :.   **:    .*.:*   ..***.

AT5G55390.1              ESVCAICDNGGEILCCEGSCLRSFHATKKDGEDSLCDSLGFNKMQVEAIQKYFCPNCEHK
GRMZM2G362718_P01        DQICALCDDGGHLLSCDGPCKRSFHPTKKDGRESKCESLHYTSAEVKRIGTYLCANCKNK
                         :.:**:**:**.:*.*:* * **** *****.:* *:** :.. :*: * .*:* **:.*

AT5G55390.1              IHQCFICKNLGSSDNSSGAAEVFQCVSATCGYFYHPHCVTRRLRLGNKEESEALERQII-
GRMZM2G362718_P01        QHQCFRCGELEPSHG--PNAKVFQCNQASCGYFYHPKCIAQLLDPNAT--DGELERRIMS
                          **** * :*  *.     *:**** .*:*******:*::: *    .  .  ***:*:

AT5G55390.1              AGEYTCPLHKCSVCENGEVKTDSNLQFAVCRRCPKSYHRKCLPREISFEDIEDEDILTRA
GRMZM2G362718_P01        GMSFPCPIHWCFKCGHMENKAQRALQLAVCRRCPRAYHRECLPRDLSFGTKDK-DGNQRA
                         . .: **:* *  * . * *::  **:*******::***:****::**   :. *   **

AT5G55390.1              WDGLLHNRVLIYCQEHEIDEELLTPVRDHVKFPFTEEQKVFVKEQRRILESHVGRDKARL
GRMZM2G362718_P01        WK--LSDTIFIYCLDHEIDKDTGTTSRNHIKFPATPEYTKTK---------GLGNSKGRM
                         *.  * : ::*** :****::  *  *:*:*** * * .             :*..*.*:

AT5G55390.1              KVKDP----------------ALQDTCGKASKNSFRSSFPSSKDGFSTKKHGLVSSVPD-
GRMZM2G362718_P01        TGKRRKNKRRKNTDQSTKPTDLPNRLCGAESEQAD--------------NVGAKSTLPQI
                         . *                    :  **  *:::               : *  *::*:

AT5G55390.1              -----HSRKRKDIDPSIKHKMVPQKSQKMMEDSREAGKNKLGVKEARDAGKSKISLGERL
GRMZM2G362718_P01        VVEPHCAAKHLKGDPQIAKQ---------------------GVA-ARQNGAETMKGHENQ
                               : *: . **.* ::                     **  **: * ..:.  *.

AT5G55390.1              FSYTQEPNPVKPGRVIPVDSKHNKTDSIASKEPGSEIPTLDNDSQRRLLAVMKKATEEIT
GRMZM2G362718_P01        FGIS-----------FC----------VAS-----------TETEKRVTCLAQR---GTC
                         *. :           :           :**           .::::*: .: ::

AT5G55390.1              MGTILKKFKIQSTMSTHSTRNVVDKTITMGKVEGSVQAIRTALKKLEEGGNIEDAKAVCE
GRMZM2G362718_P01        LGTQYD---------GPSTK---------GMYDCSVQDT-------PMDDDVELDNVACI
                         :**  .           **:         *  : ***             ::*  :..*
```

FIG. 2 (continued)

```
AT5G55390.1             PEVLSQILKWKDKLKVYLAPFLHGARYTSFGRHFTNPEKLQQIVDRLHWYADDGDMIVDF
GRMZM2G362718_P01       I---------------AVDKYVNGRGKTQ--EDYTRKEAAQRK-D---SS---------E
                                         :  ::.*   *.  ..:*. *  *:  *

AT5G55390.1             CCGSNDFSCLMNAKLEETGKKCLYKNYDLFPAKNNFNFERKDWMTVSKDELEPGSKL---
GRMZM2G362718_P01       NQGQNDALELDNLRM---------------------------EMQADERPLEPGNKRDRK
                          *.**   * * ::                            * ..:  ****.*

AT5G55390.1             ----IMGLNPPFGVNASLANKFITKALEFRPKILILIVPPETERLDKKKSSYVLIWEDKT
GRMZM2G362718_P01       WQKNVVYGLGSASGQKETLSRRE---------------NPRSDR------GMVHSND---
                            : **    * : :*:.:                  *.::*      . *   :

AT5G55390.1             FLSGNSFYLPGSVNEEDKQLEDWNLVPPPLSLWSRSDFAAKHKKIAEKHCHLSRDVGSSK
GRMZM2G362718_P01       --SKTIYYRKGGTEVDN--VDD-----HPLEKQDHQDTSSDGSKK--RSRPVDNASGGNR
                          * . :*  *..: ::  ::*      **.  .:.* ::. .*   :   :..  *..:

AT5G55390.1             LKIVEEEANASLHPLGASDGMCDDIPMEKDELEVAECVNKILVSEKIDTVETVARVHQSD
GRMZM2G362718_P01       -PYLDENKKRNLREDGRYA-HYEDWRSERNT--AADTSGYKAQSE-EKPVWTNTRTGSRE
                           ::*: : .*:  *      :*   *::   .*:       **  . * * :*. . :

AT5G55390.1             HLSRRSQLKKEGKTKDYSGRKLGKSMDSNNVDWKSNDMEEDQGELSRAPESIKVKIPEMT
GRMZM2G362718_P01       HSLDRQRIEC---GDSYRG----TYNNRQRHEWLHPHASGNSSRIG----------WDDR
                        *   *.:::     ..* *    .  : :. :*   . . :...:.           :

AT5G55390.1             SDWQSPVRSSPDDIYAVCTSISTTTPQRSHEAVEASLPAITRTKSNLGKNIREHGCKVQG
GRMZM2G362718_P01       RQWSSSRSPFPSAEFGGDRSCSRAHPRGSK----------------YRTGGRHDHPQYLG
                         :*.*     *.  :.   * * : *: *:                  .  *..  :  *

AT5G55390.1             TGKPEVSRDRPSSVRTSREDIYTV-----RPSPENTG--QKPFEAFEPSYGASLSHFDDG
GRMZM2G362718_P01       LGTPQHGTSRPHHTMGWDRDTFHDHQHGRRPPHHTMGWDRAPFRDH------QHGEYDDS
                         *.*: . .**  .    .* :       **  .. *  : **. .      . ..:**.

AT5G55390.1             LAAKYGGFGGGYRMPDPPFLPDQFPLRNGPNEMFDFRGYSDLDRGIGQREYPQQYGGHLD
GRMZM2G362718_P01       RYGEYDATDNGPDSAHRPYTAAGVAGRSAPSYQL-AGGYG-----EGSRAWR--------
                          .:* .   *    . *:    .  *..*.  :   **.      *.* :

AT5G55390.1             PMLAPPPPPNLMDNAFPLQQRYAPHFDQMNYQRMSSFPPQPPLQPSGHNLLNPHDFPLPP
GRMZM2G362718_P01       ----------------PVTDKYAP-------------------------------WPLP-
                                        *: ::***                               :***

AT5G55390.1             PPPSDFEMSPRGFAPGPNPNYPYMSRSGGWIND
GRMZM2G362718_P01       ---------------------------------
```

FIG. 3

```
Sorghum|Sb02g003420.1_Sb02g003430.1          -MSDDDDGVDPEIEDVNGYYFEDGEGEPVCFSILPFQFGENDNEADFSRKNVFLHGFVDQ
Maize|GRMZM2G362718_P01                      MFDDDDDGVDPQIEDVNRYYFEDGEEKPVCFSILPFQFGEDDSEAVFLRKDVFLCGFVDK
Rice|LOC_Os08g24946.1|13108.m23057|protein   -MMSSDDDLEPQLKAVENYYFVDDNDVPVSFDVLPFQFDAAEGVASF-KKDVYLRGFTDG
                                              : ..** ::*::: *: *** * :  **.*.:*****   :  * * :*:*:* **.*

Sorghum|Sb02g003420.1_Sb02g003430.1          SP-HVYKEVVAWKIL---------------------------------------------
Maize|GRMZM2G362718_P01                      NL-PVYKEVVAWKIRLDSEHPNIYVLSIEHKWIKLLKPRKCYGDIVRSTLITVQMLHFFG
Rice|LOC_Os08g24946.1|13108.m23057|protein   GLQKVYKQVVAWKLVLDGDSPEIAVLSTEGSWIALLKPRPSYEETIRSVLITVEMLHFVR
                                                ***:*****:

Sorghum|Sb02g003420.1_Sb02g003430.1          -----------------------------------------------------QRLIENG
Maize|GRMZM2G362718_P01                      RGEQRSSNHLWDHLDEVFGKYNPKPVEDDLMKHHTLIKLFVEKDQTLMKSKILQRLIENG
Rice|LOC_Os08g24946.1|13108.m23057|protein   RRPTDSEKDMWDHLYGVFERFVVRPLEDDFANHQNLIKLFAQRDPDLANSQVLQVFIKDK
                                                                                                  * :*::

Sorghum|Sb02g003420.1_Sb02g003430.1          FERTKKV-----------------------------------------------------
Maize|GRMZM2G362718_P01                      FKRTKKALGMEAQSIVSDG-WRAR---KNDDNNYGN-----KDDSGDDCDGDGSSDDGDG
Rice|LOC_Os08g24946.1|13108.m23057|protein   IMEKTNEVGSNNLDNKREPDIKQEPDIKQEPVAAGDEMEEIVEEGIPDAPSNDDDDDEED
                                             : ...:

Sorghum|Sb02g003420.1_Sb02g003430.1          ------------------------------------------------------------
Maize|GRMZM2G362718_P01                      SSDDDVTDQICALCDDGGHLLSCDGPCKRSFHPTKKDGRESKCESLHYTSAEVKRIGTYL
Rice|LOC_Os08g24946.1|13108.m23057|protein   EEDGDLFDSVCAICDNGGELLCCEGPCMRSFHAKIRDGEDSYCATLGYTKAEVKALKNFV


Sorghum|Sb02g003420.1_Sb02g003430.1          ------------------------------------------------------------
Maize|GRMZM2G362718_P01                      CANCKNKQHQCFRCGELEPSHGPNAKVFQCNQASCGYFYHPKCIAQLLDPNATD--GELE
Rice|LOC_Os08g24946.1|13108.m23057|protein   CKNCDHKQHQCFVCGELEPSDGPNAKVFLCNNATCGHFYHPRCVAQLLHPNSRNEASEME


Sorghum|Sb02g003420.1_Sb02g003430.1          --------------------CMENKTQRALQLAVCRRCPRAYHWECLPRELSLGAKDKDG
Maize|GRMZM2G362718_P01                      RRIMSGMSFPCPIHWCFKCGHMENKAQRALQLAVCRRCPRAYHRECLPRDLSFGTKDKDG
Rice|LOC_Os08g24946.1|13108.m23057|protein   KKIMAGFSFTCPVHWCFHCKGLEDRTQEPLQFAVCRRCPRSYHRKCLPREISFEDINTQG
                                                                     :*:::*. **:*********:** :****::*:   :.:*

Sorghum|Sb02g003420.1_Sb02g003430.1          -NPRAWKLSKTIFFYCLDHEIDKDTRTASRNHIKFPATPECTK-----TKELGNRKGRMT
Maize|GRMZM2G362718_P01                      -NQRAWKLSDTIFIYCLDHEIDKDTGTTSRNHIKFPATPEYTK-----TKGLGNSKGRMT
Rice|LOC_Os08g24946.1|13108.m23057|protein   IITRAWELSKRILIYCLDHEIDLDIGTPPRDHIKFPHVEKSAYSAKKKVKELAEKKRRIC
                                                ***:**. *::********* *  *  *:***** . : :      .* *.: * *:
```

FIG. 3 (continued)

```
Sorghum|Sb02g003420.1_Sb02g003430.1         GKRR-----KNTDQSTEPTEL---SNRLYGAESEQADNVGAKSTSPQIVVEPHCAAKVLK
Maize|GRMZM2G362718_P01                     GKRRKNKRRKNTDQSTKPTDL---PNRLCGAESEQADNVGAKSTLPQIVVEPHCAAKHLK
Rice|LOC_Os08g24946.1|13108.m23057|protein  DDSY----------VSEPLQKRAKLNEKFNAKGDKSKKAGVKSEFEEVLESEKKKTRSLK
                                             .             ::* :     *.   *:.:::.:.*.**   ::: . :  :: **

Sorghum|Sb02g003420.1_Sb02g003430.1         GDPQIEQSIIGV---AGSQNGAETMNGHEKQFG-----------IS-CVARTETEKRVTY
Maize|GRMZM2G362718_P01                     GDPQIAK--QGV---AARQNGAETMKGHENQFG-----------ISFCVASTETEKRVTC
Rice|LOC_Os08g24946.1|13108.m23057|protein  KRTQPEEPLVECAAAAAANNANRPVKEREKELGTSSLDMGKIPLSSFPIVDSETEKRISA
                                               *  :        *. :*. . :: :*:::*            *  :. :*****::

Sorghum|Sb02g003420.1_Sb02g003430.1         LAQKG-------------------TCLGTPYDGPSTKDMSDCSVQDTPVD-----KDFEL
Maize|GRMZM2G362718_P01                     LAQRG-------------------TCLGTQYDGPSTKGMYDCSVQDTPMD-----DDVEL
Rice|LOC_Os08g24946.1|13108.m23057|protein  LVEKEVSSLTVADISRRCVIPSTYACSGRQIDKIVVRGKLERSIQAVKAALQKLENGGAV
                                            *.::                    :* *   *   .:   : *:* .        .   :

Sorghum|Sb02g003420.1_Sb02g003430.1         D--NVAYR---------------IMEDKYANGREET--QEDYTRKETAHRKDSSENQGQN
Maize|GRMZM2G362718_P01                     D--NVACI---------------IAVDKYVNGRGKT--QEDYTRKEAAQRKDSSENQGQN
Rice|LOC_Os08g24946.1|13108.m23057|protein  DDAKAVCESEVLRQLTRWHNKLRVYLAPFIHGMRYTSFGRHFTKKEK-------------
                                            *  :..                 :    : .*   *   ..:*:**

Sorghum|Sb02g003420.1_Sb02g003430.1         DVLELD--NLWVEIQAD--GSPLEPGNKRYK--EENAYGLGSASGHEKET--SSSRRENV
Maize|GRMZM2G362718_P01                     DALELD--NLRMEMQAD--ERPLEPGNKRDRKWQKNVYGLGSASGQKE----TLSRRENP
Rice|LOC_Os08g24946.1|13108.m23057|protein  -LIEIAEKLHWYVQPGDMKSNNVDPETRPRR--VNMLRGFGALSQFMKEKLDKVGKRCNF
                                              :*:          .*     ::* .:  :   :   *:*: *   :    . .:* *

Sorghum|Sb02g003420.1_Sb02g003430.1         QSDRGMVPMNDSKTIDYRKG-GTTLDNNVYDHS---SEGSYPCQGECS---HSKCN----
Maize|GRMZM2G362718_P01                     RSDRGMVHSNDSKTIYYRKG-GTEVDNVD-DHP---LE----------------------
Rice|LOC_Os08g24946.1|13108.m23057|protein  KNYD-VIQPKNS--FSFEKRDWMTVRQKELPHGSKLIMGLNPPFGPKAMLANKFIDKALT
                                            :.   ::  ::*  : :.*     : :    *

Sorghum|Sb02g003420.1_Sb02g003430.1         --DGLVAIDQDTSSDRLKKRSQPVEKA------SDGNKTDLDKNKKHNLKE--------D
Maize|GRMZM2G362718_P01                     -----KQDHQDTSSDGSKKRSRPVDNA------SGGNRPYLDENKKRNLRE--------D
Rice|LOC_Os08g24946.1|13108.m23057|protein  FKPKLIILIVPKEAERLDRKQQPYDLVWEDDQRLSGKSFYLPGSLDVSDKQIDQWNKSPP
                                                       ..::  .::.:* : .        *:   *  . . . ::

Sorghum|Sb02g003420.1_Sb02g003430.1         GR-DAHYEDRRTERNTAADTSRYKCRDKIQLDRREPELVGRNTRARSSEHSPERQRMERD
Maize|GRMZM2G362718_P01                     GR-YAHYEDWRSERNTAADTSGYKAQSE-------EKPVWTNTRTGSREHSLDRQRIECG
Rice|LOC_Os08g24946.1|13108.m23057|protein  PLYLWSRPDWTQKHKRIAEQHGHTKANV--FSHNEEDLVYLFEDRATQNHDVNNKNYTSG
                                                    *   :::  *:   :.  .         . *       : :*. :.:.
```

FIG. 3 (continued)

```
Sorghum|Sb02g003420.1_Sb02g003430.1          ------------GSYPGT-YNRRRYESL-H------NFNPPRSGCDDRRQLSPCQSSFPL
Maize|GRMZM2G362718_P01                      ------------DSYRGT-YNNRQRHEWLH---PHASGNSSRIGWDDRRQWSSSRSPFPS
Rice|LOC_Os08g24946.1|13108.m23057|protein   NGNFTAEKPVQADAFPPEKLVEVAYEEMKVASNRSSMYQSDQISVHDERD---AHSDLPM
                                                          ::      .   ..           :  : . .*.*:   .:* :*

Sorghum|Sb02g003420.1_Sb02g003430.1          PEFCGDHSH--L-Y--PRDS---TIGRH---------NPHRYLG----I-----------
Maize|GRMZM2G362718_P01                      AEFGGDRSC--S-RAHPRGSKYRTGGRH---------DHPQYLG----LGTPQHGTSRPH
Rice|LOC_Os08g24946.1|13108.m23057|protein   SRHNSMKAKEVSNSSRDRRKSDKTGHEADSDMSILPSDSRNFLHKSGNLEPPISS----R
                                              .. . ::         * .   *  .          :  .:*     :

Sorghum|Sb02g003420.1_Sb02g003430.1          -------------------------------------------------------PQYGP
Maize|GRMZM2G362718_P01                      HTMGWDRDTFHDHQHGRRPPHHTMGWDRAPFRDHQHGEYDDSRYGEYDATDNGPDSAHRP
Rice|LOC_Os08g24946.1|13108.m23057|protein   SGYTLERLRYHDNHFDHLVGEHSSSS-------LQMPIFEDSYFRSV-----------NE

Sorghum|Sb02g003420.1_Sb02g003430.1          YMAASAAGHSAVCYRLAGGYGEGSRASRPVTDW--YAPHLD-------------------
Maize|GRMZM2G362718_P01                      YTAAGVAGRSAPSYQLAGGYGEGSRAWRPVTDK--YAPWPL-------------------
Rice|LOC_Os08g24946.1|13108.m23057|protein   YGVASVENN---IALSTDNVGAGSRMYSPDPELNGYAVDPTVNAYGSVSGGTGGSFYRRQ
                                             * .*.. .       :   * ***   *  :   **

Sorghum|Sb02g003420.1_Sb02g003430.1          -----------RTNCQPRSQIDLQ------------------------------------
Maize|GRMZM2G362718_P01                      -----------P------------------------------------------------
Rice|LOC_Os08g24946.1|13108.m23057|protein   NLEDYTMDSSESAQMNPVPGRDVQEYARTYYGHNRDEVPQTAINTPSMDIRTHIRMYGRH

Sorghum|Sb02g003420.1_Sb02g003430.1          ------------------------------------------------------------
Maize|GRMZM2G362718_P01                      ------------------------------------------------------------
Rice|LOC_Os08g24946.1|13108.m23057|protein   IRDDHTQTTMNPPANDIRAQIRMYGQHATSDHQHASRYSSGSPDARFEQQPSFTSYGMPS

Sorghum|Sb02g003420.1_Sb02g003430.1          -LQASRPVTDKYAPQLELTNYPPRSQSDL--------------QYCTTTI*---------
Maize|GRMZM2G362718_P01                      ------------------------------------------------------------
Rice|LOC_Os08g24946.1|13108.m23057|protein   LGSTGRSMMDRYSPSIDETSYRTGQRGPYNASDFRRDRHPDDMNFALHNQYPYPHPGSSG

Sorghum|Sb02g003420.1_Sb02g003430.1          ----
Maize|GRMZM2G362718_P01                      ----
Rice|LOC_Os08g24946.1|13108.m23057|protein   GWHD
```

FIG. 5

| | NAM | | IBM | NyH | OWRI | WiDiv | CYMMIT |
|---|---|---|---|---|---|---|---|
| No. of lines | 3875 | | 302 | 243 | 277 | 573 | 503 |
| Year$^{reps}$ | $2008^{1}$ | $2009^{1}$ | $2008^{2}$ $2009^{2}$<br>$2010^{1}$ $2011^{1}$ | $2010^{1}$ $2011^{2}$ | $2010^{1}$ $2011^{2}$ | $2009^{2}$ $2010^{2}$ | $2010^{1}$ |
| Location | WM | ARL | WM ARL<br>ARL WM | WM | WM | ARL | WM |
| Plot size/ Plants | 1/42 | | 2/42 | 1/15 | 1/15 | 2/42 | 1/13 |
| Traits Measured | Transition<br>DAP<br>DAS | Transition<br>Node #<br>Plant Height | Transition<br>Node #<br>Plant Height<br>DAP | Transition | Transition | Transition<br>Node #<br>Plant Height<br>GDD | Transition |

SEQUENCE LISTING

```
<160> NUMBER OF SEQ ID NOS: 19

<210> SEQ ID NO 1
<211> LENGTH: 10679
<212> TYPE: DNA
<213> ORGANISM: Zea mays

<400> SEQUENCE: 1

tggtcgtatt gtaccaagac atattggatg tagtaaacaa caacatcagt tagttaaatt      60

taaaaaaata tgtagagagc ggagacaatc aataaaaaat ttgagatttt tttggttgat     120

agtttacgtg gatattgttg tgagccgtcg taacgcacgg gtaaccgact agttcgtttt     180

ggatggattg gtctattcct tgttttgctt caagcggaat aaaacaatct ggtttagaat     240
```

-continued

```
ccggtccatg tgttcttttt acccgaatca agaataaatc tgtatgattt tgacccacac    300
ctggatggat tcctggctat agctaggaat gagtgatcca ctgggtcccg ggctggttgg    360
cttggtggcc tggctttgat tcgggtttgc ggaacggggc tttagggcct caaccatgta    420
aggacttatt cagttattcc cattatatat ggattagatg aaattagaaa aaatttaaaa    480
gaactttaac ttaattggaa tttaaacaca tctaattcca ttcaatcgga ataagcctaa    540
tacggttact gtaacacaaa cggcctatca aaagggccta aaccacgtag tacggttact    600
gtaactccaa aacctccctg ccttctctcc ttccatcacc gcaactccaa agcctcttat    660
cgtcttcttc catcgccgaa cgacgactgg gcccgctgtc gctgccgccg ccgccctact    720
tcgccacctt cgccggcgac gggcaccacc aggtatgccc cccccccccc cggtcttccc    780
ttcctgctgc gcgaagccgt gcgcccaaac cgtaacgtaa tccgttgata cgtcctcccc    840
ttggtcctca cttcttgctg tgcgaaaccg tgcgcctaaa ccctaacgta ccttttgtat    900
ccggatctga atctagttac aagtgtatat gcatgcagta tgcctactaa cctcgatttc    960
tttgaaaaaa aatcgggtgt cctgcattca agggcggcgt taaatatttt tagacaatgg   1020
aaaaaattca gttccagcct tttacagttg cttgtatacg gccttacaaa acagtccata   1080
caaatcttga acgaactaga agtggtatag aaagaaagcc tgagatttgt gtggactgtt   1140
ttgtaacatt tttatcccac aattaagtca gaacgtctct ttcgtgtgga ctgcatttgc   1200
attagtgatt gtgtggcgtt aaatatagtc aattttatcc cacaattaag tcagaacgtc   1260
tgtttcgtgt tacttcttgt gcaacatttt tatttagtgg taatttcatg tggagcgtct   1320
gcaaacttag accactaagg gctgggccgg ctggttgatt ctgaattccc ccaaatcttt   1380
cacccccctc attgccagta gtttgatgga ggttgtgtag gaatttttca cccctcacga   1440
gcttctagct tatcggtttg tcttatcggc ttatcgctta aattctttat tgtaagtctg   1500
tagttgcagc cgagcagttg gagtgttaaa tatttgatgt attgccatga gatgtcaaat   1560
actcaaacta caatatcaaa ttagtgggaa actgtgtatt aacttttggg tgatgactgc   1620
tttgttagta acattatcaa gctagttgcc ttgcaggttg ctatattacg aacacttcaa   1680
tgtgtgctct tatattcatg gttattcacc tgataaccac atgtcatatt cctgttttca   1740
gtgtattatt tcgattagta agctaatgct tccatagatc attagttatt gtttactgca   1800
ttttgtcttg ttgttagccc tgttctgaat aaaagagtat ctatttgttc ttgctttttt   1860
tttgtgcaaa atgtcatatt gtttggtctc cgtgaaagca aattaccagt gttcatttgc   1920
tgtaacaact ttgataaatt taggcttaat agtgaactaa cttctgtcag atttcttttt   1980
tttttcttgc ttcaatcaag tgtggactgt aatgtttgat gatgatgatg atggagtgga   2040
cccacaaatt gaggatgtca acagatacta ctttgaggat ggtgaagaga aaccagtttg   2100
tttcagtatc ttgcctttcc agtttggtga ggacgatagc gaggcagttt tcctcagaaa   2160
ggatgttttc ttgtgtggat ttgtggataa aaatcttcct gtgtacaagg aggtggtagc   2220
ttggaagata aggcttgaca gtgagcatcc caacatctat gtgctttcta ttgagcacaa   2280
gtggataaag ctgttgaaac cacgaaaatg ctatggagac attgttcgat caacattgat   2340
tacggtgcaa atgctccact tttttgggag aggggagcaa agaagttcga atcacctttg   2400
ggatcacctt gatgaagttt ttgggtatcc atctacatgc ttactttgtc tttaccctcg   2460
agtatatgct tataatgttt attcgtttgt cttttgaagt aaatacaatc ctaaacccgt   2520
ggaggatgac ttgatgaagc accataccct aatcaagttg tttgtagaga aagatcaaac   2580
cttgatgaag tcaaaggtac aagttacttt gccctaccgc cctactttct actccctttc   2640
```

-continued

```
tttttgaggg aaatacacac agtagggagg gcccttgtat tgcctttgaa agcatggtaa   2700
tttgatttca agttgaaact ttacataatc aactagaatt tccaccctca atttgtttgc   2760
gtggaagttt ttatataatt tcgtcattac cttgaataat ggatcttatt gatttttcag   2820
agtcatgaga caagttagac gagtggcatg gactgatttt tctccttttt tgcatatatg   2880
cagattcttc aaaggctcat tgagaatggc tttaagagaa ctaaaaaggt atgctaagat   2940
ctatatgtta gctttacaaa caacagtgag aatcatgatg taggcatatt tgtgaagagt   3000
gacagggaga agagatgttg tggggcactt tcattttgtt tcctaactta gttgctgggc   3060
tgcggaactt caggatgcgc cagcaacttg tatggcgaaa agttgttggg gtttattcaa   3120
gaaagctttc atagttcatg gttgagtcag agttttttat agtcatgaaa tcagattgat   3180
caggaggttc caaattaagt tagatgacat ttatcgctca aatttataat gtgcacttct   3240
cttgttacta tgttccaatg tccattttac tctgtccggt agaaataagt gtcgttttgg   3300
acactgattt agtccccaaa atagaacttt gactatttct ttaatacatt tattacgaag   3360
gatagcaaaa ggccaaaagt atagtgttat tgaactattt tgtgtgaccc tacttataat   3420
atttttcaaa tacccaaact tagtacataa aaagtatttt gttatcagag gttggaatgg   3480
ttgaatgcac acaacccaaa acgacactta tttaacttga gggagaattt ttttaaaaca   3540
tattcagggt ttttcatgtt tcacttttct tttgaatgag cctattttaa aggccttagg   3600
tatggaagca caatccattg ttagtgacgg gtggcgtgct agaaaaaatg atgataacaa   3660
ttatggtaac aaagatgaca gtggtgatga ttgtgatggt gatggtagca gtgatgatgg   3720
tgatggcagc agtgatgatg atgttaccga tcaaatatgt gcgctatgtg atgatggagg   3780
acatttgctt aggtaggtgc acaaaattga ctatctgtct tttattccat ttcttgtaca   3840
tgtgctccat atctttatcc atgccatgat caatattatt aagcaccttc cacttggatc   3900
aacaccttta acgcttgcat gaaatatggt cactaacagt atgcgaagat taaggcaata   3960
ggcaagggga aataaggtta acgttaaaga gataacagaa gcaaaaggta gcagagaaaa   4020
gagaaagggg aagatagata acaatggcca ccaattcagc ctaattgcag ctagatccac   4080
cttgcttaat ccttctaagt cccatttcct aatcgtagca gtctccctta aattgtctcc   4140
caatttgaac acagttggta tatgtgagct atagacaaag atgcaataaa gagtggatcc   4200
aaaagctgtg aaccgcatat gaggcggact aggatgccac gcctaagttt gggtgtttca   4260
actatcaact ttcaagatca cttgtgcctc ttatttacac tgtcagttca taggctatga   4320
gttgtctcct tgaatttgta caaggtgaat ttactttatg cagtttcaca ttaagggttt   4380
gcttctggag taaatgtgga aatctactga attacttgta agatcagcga gttgaagttt   4440
tgatgaacca taacaaggaa aaacacttat tactttctgc atgcaagtga cagatgagga   4500
tgtcttccac gatatccatg gagtgttcat tgtgttttgt agcatataat gtttctgtct   4560
gtaagctctt gttgggttat taaatcagtt cgattatata ctttaattct tacaatgatt   4620
taattcagct gtgacggtcc atgcaagagg tctttccacc ccacaaagaa agatggcaga   4680
gaatctaaat gtgaaagtct tcattacact tcagcagaag taaaggtagc ttcttgaaat   4740
ttttactcaa tggtgctgcc agccttttca ttttcctggc tttaattagt gacatgtcat   4800
ttttgtttac agagaattgg tacttatcta tgtgcaaact gcaaaaaataa gcaacaccaa   4860
tgttttagat gtggagagct tgaaccatcc catgggccaa atgctaaggt atactgaagc   4920
cactatgctt agtatttttt ttcatttaac agacacactt ttttcttgaa cataaaggag   4980
```

-continued agctgtgtat cattatatga acaagatata actgaataga gaaaccctta caaaacatac 5040
actagcacgg tagcacccca tcacactcga acagctagat cgcctatgtt acaccacaaa 5100
gcactaccat gaccaggagg aaaaaacacc tctaaacccc tcaagtgaca aggcagctag 5160
ataagcaatg cctttagccc ctgccaaacc cctaatctca tctcctcagc agccaacagt 5220
gtgatgctct caaattttgg tgaggcccca taaaatgcac agcgattaag atgattctaa 5280
atggtccaag ttttgagaat agaatttaga cttgccaaac ctgtccgatc acctcttcgt 5340
tgattctaga ccaccagcca tcaaaggaag actcctgctg agggaattta agacagtgtt 5400
gcttatttcc tatcatagtt ttcctatttt cctattccat tatgtttttg aattttagta 5460
ttccctccat gccacatgga atgctaaact agtgtggaaa caaaagacaa tattatggca 5520
ctgggccttc gcagcggtac atggccaagc acagcagtat atgcacgaca aggcagtagc 5580
agcatggtac acattacagt tattgttagc tactttagag cattccaaca aaaagtcctt 5640
tatttgagtc atcaaaatta aataggactt gatttgaagt gtttaggacc acaaaaacgt 5700
ttgcagctcc aacaattgag ccatatatca tattattagg aaacaaatca tgttatttgg 5760
aaaataaaag attaggaata gtgtaccaaa tgaggatagg gctccggtaa atggggtact 5820
atatttagga gttaggaccc gagagaccga gccctataat cattcgatga atttttgtaa 5880
aatagggccc cttttggagc atgtttttgg tgttagagtc ctatatttca aaataggacc 5940
ccgtttgtgg ctcatgttgg agatgctctt agagctttag atataataga ttgtatggct 6000
taaattcatg tatgcgactg acctatcaga ttgcacattg cttagtttgg ttaggggtgc 6060
agcctattta ataggcatcc atgtattggt gtgggtaagc aatgtaggcc ctcatgtact 6120
atctagcaac attcttctct cttttgaaca tcattatcct cagtcactct tcctatattt 6180
tagagttaca tgcatgagca gcccctgaag tcgttaagag gtgccacttt ggtccatgaa 6240
ctttgaaaac acatttctaa gaccctaaac ttgttaagtg gtgcaccaca atggtcggta 6300
tggtccagaa atagacctgg cggtgcacca ttttacaagt ttagtgatgt gtggtgcacc 6360
atgaaacaaa attaggggcc ctaaaccaca tttacaaagt tcatgggcct aaagtggtgc 6420
ccttttataa gtttaggcgc cgctgatgca tttaactcta ttttactacc tccgacccaa 6480
attataggtt attttggctt ttgtgatatc ctggcccaag tggattgtgt gatatcatgg 6540
cccaaggctt aataatattg atagaatcct cataccaaca aggtgcatct tctttttcgg 6600
aagcctgtct cgaaaaaacc tctggcttaa gcatgcatag cccagagcaa tcatgggatg 6660
ggtgaccgac cgagaagtct tctcggttgc gcatgaggcc aaagtgtgca caaaaggctc 6720
gtgttggttt gtggggatga tctatggtcc tagagggttg ccagaattaa gtaccgtcgg 6780
tctgagagcg gacggggtgt tacagttttt tggaacatag tatttgctat ccacctaaat 6840
atatgttatg tctagataca tagcttgtgc tctctccatt caatatttgc tatgcacact 6900
tagatatata ctatctctag atacataata aaagtaatgt atctaaaaaa ccaaaatgtc 6960
gtataatttg gaatggagta ctatgtattt agaaagccaa aatgacctaa atttagaatg 7020
gaggaattaa ctgctaaatc tattttggtc ttaatcagta gcgtacattc tgttaggtct 7080
ttcaatgcaa tcaagcatct tgtggatatt tttaccaccc taagtgcatt gcacaattat 7140
tggatcctaa tgccactgat ggtgagttgg aaagaaggat tatgtcggga atgtcatttc 7200
cgtgccccat acattggtgt ttcaaatgtg gccacatgga gaacaaagct caaagagcac 7260
ttcagcttgc agtgtgtaga cgctgtccaa gagcatatca cagggaatgc cttccaaggt 7320
actgttcatc cagattggtt gcttagattg tttagtttgt ctagttgtgc tgttcttatg 7380

```
ccgtctaatg tatattctag ggacttatcc ttgttcatcc agattggttg cttagattgt   7440
ttagtttgtc tagttgtgct gttcttatgc cgtctaatgt atattctagg gacttatcct   7500
ttggaacaaa ggacaaggat ggtaaccaac gcgcttggaa gctttccgac acaattttca   7560
tttactgcct gtaagttatt cctgatttgt ttgccattat ttttctgcaa ttgctgctca   7620
cagcatttga cttctgttaa atatcgtgca gagatcatga aatagacaag gatactggca   7680
caactagtag gaaccatata aaatttccag ctacacctga atacaccaaa acaaaagggc   7740
ttggtaacag caaaggaagg atgactggca aaaggagaaa gaacaaaagg agaaagaaca   7800
ctgaccaatc aacaaaacct acagatttgc caaacaggtt gtgtggagca gaaagtgagc   7860
aagctgacaa tgtaggtgca aaaagcacat tgccccagat tgttgtagag cctcactgtg   7920
cagcaaagca cttgaagggt gatccacaaa ttgccaaaca gggtgttgct gctcgtcaaa   7980
atggtgcaga aactatgaaa gggcatgaaa atcaatttgg catttcattt tgtgttgcaa   8040
gtactgaaac agagaagagg tagctcagtg tcctttttca cctgtttttt ttatactttt   8100
gcctacagaa tatatagatt agattaaaaa tttcaacttg tgacttcaac aaaccttatc   8160
ttttatattt tggctggctc taatgtacaa ctaccaatat tttcttttgt agataaattt   8220
ttggtttgct gtattgttcc tattcattct ttctgtggtg tagctcaagt ggcaatatgc   8280
cacaagagta tggctaacag ttgacagggg tctgttggtt tttcatttca gggtaacatg   8340
tttggcacaa aggggaacat gtttagggac acaatatgat gggccatcaa ccaagggcat   8400
gtatgattgt tctgttcagg tgcttataga ctaacacgac tagcctatta acatctgcaa   8460
actgtaatct attcttacat ctgtacaaga aaacatgttt tatgtgaact aattggaaac   8520
cttgttgcag gacaccccta tggacgacga tgttgagttg gataatgtgg cctgcataat   8580
cgcggtggat aaatatgtca atgggagggg gaaaacacaa gaggactaca ctagaaaaga   8640
agctgctcag cgcaaagact cgagtgaaaa tcaagggcag aatgatgctc tagagctaga   8700
caacctccgg atggagatgc aagctgacga acgtccgtta gaaccaggaa acaagaggga   8760
caggaagtgg cagaaaaatg tatatggact cggatcagct tcgggacaga aggaaacctt   8820
gtccaggaga gaaaatccac ggtcagatag agggatggtc cacagtaacg acagcaaaac   8880
aatttattac aggaagggtg ggacggaagt cgataatgtt gatgaccacc ctttagaaaa   8940
gcaagaccac caggatacat caagtgacgg atctaaaaag agaagccgac cagtggacaa   9000
cgcatctggt ggcaacagac catacttgga tgagaacaag aagcgtaatc tcagagaaga   9060
tggaagatat gctcattatg aagactggag aagtgaaagg aatacagcag cagacacgtc   9120
tggatataag gcccaatcag aagagaagcc tgtatggaca aacactcgaa caggatcaag   9180
ggagcattca ctggacaggc aaaggataga gtgcggtgac agctatcgtg gaacctataa   9240
caatagacaa agacatgaat ggctgcaccc gcacgctagt ggtaattcct cgagaattgg   9300
ttgggatgac aggaggcagt ggagttcatc tcggtcacca tttccttcgg ctgaatttgg   9360
tggtgaccgt tcctgttctc gtgcccatcc gagaggttct aaatacagaa ccggcgggag   9420
gcatgatcac ccccagtacc tgggactggg aacacctcaa catggtacaa gtagaccgca   9480
ccacacaatg ggctgggaca gggacacctt ccatgatcac cagcatggca gaagaccgcc   9540
gcaccacaca atgggctggg acagggcccc cttccgtgat caccagcatg gcgaatacga   9600
cgactccagg tatggtgaat atgatgcaac tgacaatggt cctgacagcg cgcatcgacc   9660
ctacacggct gctggcgtgg ctggacgttc agcaccgagt tatcagcttg ctggtggtta   9720
```

-continued

```
tggagaggga tcaagggctt ggcggccagt tacggacaag tacgccccat ggcccttgcc   9780
ttgaccgcac aaactaatat tagccaagga gccagagtga gctacaagaa caccgtttgc   9840
tattgtcgga aatgctttct tcgaggactg tctcagtacg gggaattgat gggtcggtgt   9900
tgaaacccaa atgatatctg ccttccagtt gcttgctttg cctatcgtaa tcactgcatg   9960
ttatttcaca taagcagctg gattctcaag ttatgtgggc ggtgcatttg agttatacta  10020
gatgacagcc tgtgcatatt gttactgaag taaaatatct tttttattag gttcccctta  10080
tctcgctgtg ttgttggtca atggttatgg actatctagt ttgtcaaccc catttttttga  10140
agaaattttt atttttaaa gaaaaatcag ttcattttaa aaaaatgaga atctctgaga  10200
aagttgataa acaagccctt aattggtaaa aagactctaa tgaactacgt gttttagtcc  10260
caacatcgtg atagaatagg gtcactttta taagtatttg aacaactgat tttctgtcgg  10320
tggttataac gctccttcaa acggcaacgc aaaaattgtt ttacaattcg gttttcatct  10380
ctatgagtaa aaaatatcaa tagacttagc cccaatccgt tttagcaaaa tttaaatttg  10440
cccaacaaat agacttagtc cattgataaa aagttaattt tgtcttggct ggggtgcgcc  10500
atgctcgggc agcagtgcaa cgtccgagcg acactcaagg accccaatag caagctatta  10560
tgatgggttc tcccccgtaa aaaataaatt taatatcgaa atgaacacat ggttcacata  10620
tcagatatta aactgataag aacagatact acacttgatc ttagccaaaa ggccgagaa   10679
```

<210> SEQ ID NO 2
<211> LENGTH: 3479
<212> TYPE: DNA
<213> ORGANISM: Zea mays

<400> SEQUENCE: 2

```
gtaactccaa aacctccctg ccttctctcc ttccatcacc gcaactccaa agcctcttat     60
cgtcttcttc catcgccgaa cgacgactgg gcccgctgtc gctgccgccg ccgccctact    120
tcgccacctt cgccggcgac gggcaccacc agtgtggact gtaatgtttg atgatgatga    180
tgatggagtg gacccacaaa ttgaggatgt caacagatac tactttgagg atggtgaaga    240
gaaaccagtt tgtttcagta tcttgccttt ccagtttggt gaggacgata gcgaggcagt    300
tttcctcaga aaggatgttt tcttgtgtgg atttgtggat aaaaatcttc ctgtgtacaa    360
ggaggtggta gcttggaaga taaggcttga cagtgagcat cccaacatct atgtgctttc    420
tattgagcac aagtggataa agctgttgaa accacgaaaa tgctatggag acattgttcg    480
atcaacattg attacggtgc aaatgctcca ctttttttggg agaggggagc aaagaagttc    540
gaatcacctt tgggatcacc ttgatgaagt ttttggtaaa tacaatccta aacccgtgga    600
ggatgacttg atgaagcacc ataccctaat caagttgttt gtagagaaag atcaaacctt    660
gatgaagtca aagattcttc aaaggctcat tgagaatggc tttaagagaa ctaaaaaggc    720
cttaggtatg gaagcacaat ccattgttag tgacgggtgg cgtgctagaa aaaatgatga    780
taacaattat ggtaacaaag atgacagtgg tgatgattgt gatggtgatg gtagcagtga    840
tgatggtgat ggcagcagtg atgatgatgt taccgatcaa atatgtgcgc tatgtgatga    900
tggaggacat ttgcttagct gtgacggtcc atgcaagagg tctttccacc ccacaaagaa    960
agatggcaga gaatctaaat gtgaaagtct tcattacact tcagcagaag taaagagaat   1020
tggtacttat ctatgtgcaa actgcaaaaa taagcaacac caatgtttta gatgtggaga   1080
gcttgaacca tcccatgggc caaatgctaa ggtctttcaa tgcaatcaag catcttgtgg   1140
atattttttac caccctaagt gcattgcaca attattggat cctaatgcca ctgatggtga   1200
```

-continued

```
gttggaaaga aggattatgt cgggaatgtc atttccgtgc cccatacatt ggtgtttcaa   1260
atgtggccac atggagaaca aagctcaaag agcacttcag cttgcagtgt gtagacgctg   1320
tccaagagca tatcacaggg aatgccttcc aagggactta tcctttggaa caaaggacaa   1380
ggatggtaac caacgcgctt ggaagctttc cgacacaatt ttcatttact gcctagatca   1440
tgaaatagac aaggatactg gcacaactag taggaaccat ataaaatttc cagctacacc   1500
tgaatacacc aaaacaaaag ggcttggtaa cagcaaagga aggatgactg gcaaaaggag   1560
aaagaacaaa aggagaaaga acactgacca atcaacaaaa cctacagatt tgccaaacag   1620
gttgtgtgga gcagaaagtg agcaagctga caatgtaggt gcaaaaagca cattgcccca   1680
gattgttgta gagcctcact gtgcagcaaa gcacttgaag ggtgatccac aaattgccaa   1740
acagggtgtt gctgctcgtc aaaatggtgc agaaactatg aaagggcatg aaaatcaatt   1800
tggcatttca ttttgtgttg caagtactga aacagagaag agggtaacat gtttggcaca   1860
aaggggaaca tgtttaggga cacaatatga tgggccatca accaagggca tgtatgattg   1920
ttctgttcag gacaccccta tggacgacga tgttgagttg gataatgtgg cctgcataat   1980
cgcggtggat aaatatgtca atgggagggg gaaaacacaa gaggactaca ctagaaaaga   2040
agctgctcag cgcaaagact cgagtgaaaa tcaagggcag aatgatgctc tagagctaga   2100
caacctccgg atggagatgc aagctgacga acgtccgtta gaaccaggaa acaagaggga   2160
caggaagtgg cagaaaaatg tatatggact cggatcagct tcgggacaga aggaaacctt   2220
gtccaggaga gaaaatccac ggtcagatag agggatggtc cacagtaacg acagcaaaac   2280
aatttattac aggaagggtg ggacggaagt cgataatgtt gatgaccacc ctttagaaaa   2340
gcaagaccac caggatacat caagtgacgg atctaaaaag agaagccgac cagtggacaa   2400
cgcatctggt ggcaacagac catacttgga tgagaacaag aagcgtaatc tcagagaaga   2460
tggaagatat gctcattatg aagactggag aagtgaaagg aatacagcag cagacacgtc   2520
tggatataag gcccaatcag aagagaagcc tgtatggaca aacactcgaa caggatcaag   2580
ggagcattca ctggacaggc aaaggataga gtgcggtgac agctatcgtg gaacctataa   2640
caatagacaa agacatgaat ggctgcaccc gcacgctagt ggtaattcct cgagaattgg   2700
ttgggatgac aggaggcagt ggagttcatc tcggtcacca tttccttcgg ctgaatttgg   2760
tggtgaccgt tcctgttctc gtgcccatcc gagaggttct aaatacagaa ccggcgggag   2820
gcatgatcac ccccagtacc tgggactggg aacacctcaa catggtacaa gtagaccgca   2880
ccacacaatg ggctgggaca gggacacctt ccatgatcac cagcatggca gaagaccgcc   2940
gcaccacaca atgggctggg acagggcccc cttccgtgat caccagcatg gcgaatacga   3000
cgactccagg tatggtgaat atgatgcaac tgacaatggt cctgacagcg cgcatcgacc   3060
ctacacggct gctggcgtgg ctggacgttc agcaccgagt tatcagcttg ctggtggtta   3120
tggagaggga tcaagggctt ggcggccagt tacggacaag tacgccccat ggcccttgcc   3180
ttgaccgcac aaactaatat tagccaagga gccagagtga gctacaagaa caccgtttgc   3240
tattgtcgga aatgctttct tcgaggactg tctcagtacg gggaattgat gggtcggtgt   3300
tgaaacccaa atgatatctg ccttccagtt gcttgctttg cctatcgtaa tcactgcatg   3360
ttatttcaca taagcagctg gattctcaag ttatgtgggc ggtgcatttg agttatacta   3420
gatgacagcc tgtgcatatt gttactgaag taaaatatct tttttattag gttcccctt    3479
```

<210> SEQ ID NO 3

<211> LENGTH: 1006
<212> TYPE: PRT
<213> ORGANISM: Zea mays

<400> SEQUENCE: 3

Met Phe Asp Asp Asp Asp Asp Gly Val Asp Pro Gln Ile Glu Asp Val
1 5 10 15

Asn Arg Tyr Tyr Phe Glu Asp Gly Glu Glu Lys Pro Val Cys Phe Ser
20 25 30

Ile Leu Pro Phe Gln Phe Gly Glu Asp Asp Ser Glu Ala Val Phe Leu
35 40 45

Arg Lys Asp Val Phe Leu Cys Gly Phe Val Asp Lys Asn Leu Pro Val
50 55 60

Tyr Lys Glu Val Val Ala Trp Lys Ile Arg Leu Asp Ser Glu His Pro
65 70 75 80

Asn Ile Tyr Val Leu Ser Ile Glu His Lys Trp Ile Lys Leu Leu Lys
85 90 95

Pro Arg Lys Cys Tyr Gly Asp Ile Val Arg Ser Thr Leu Ile Thr Val
100 105 110

Gln Met Leu His Phe Phe Gly Arg Gly Glu Gln Arg Ser Ser Asn His
115 120 125

Leu Trp Asp His Leu Asp Glu Val Phe Gly Lys Tyr Asn Pro Lys Pro
130 135 140

Val Glu Asp Asp Leu Met Lys His His Thr Leu Ile Lys Leu Phe Val
145 150 155 160

Glu Lys Asp Gln Thr Leu Met Lys Ser Lys Ile Leu Gln Arg Leu Ile
165 170 175

Glu Asn Gly Phe Lys Arg Thr Lys Lys Ala Leu Gly Met Glu Ala Gln
180 185 190

Ser Ile Val Ser Asp Gly Trp Arg Ala Arg Lys Asn Asp Asp Asn Asn
195 200 205

Tyr Gly Asn Lys Asp Asp Ser Gly Asp Asp Cys Asp Gly Asp Gly Ser
210 215 220

Ser Asp Asp Gly Asp Gly Ser Ser Asp Asp Asp Val Thr Asp Gln Ile
225 230 235 240

Cys Ala Leu Cys Asp Asp Gly Gly His Leu Leu Ser Cys Asp Gly Pro
245 250 255

Cys Lys Arg Ser Phe His Pro Thr Lys Lys Asp Gly Arg Glu Ser Lys
260 265 270

Cys Glu Ser Leu His Tyr Thr Ser Ala Glu Val Lys Arg Ile Gly Thr
275 280 285

Tyr Leu Cys Ala Asn Cys Lys Asn Lys Gln His Gln Cys Phe Arg Cys
290 295 300

Gly Glu Leu Glu Pro Ser His Gly Pro Asn Ala Lys Val Phe Gln Cys
305 310 315 320

Asn Gln Ala Ser Cys Gly Tyr Phe Tyr His Pro Lys Cys Ile Ala Gln
325 330 335

Leu Leu Asp Pro Asn Ala Thr Asp Gly Glu Leu Glu Arg Arg Ile Met
340 345 350

Ser Gly Met Ser Phe Pro Cys Pro Ile His Trp Cys Phe Lys Cys Gly
355 360 365

His Met Glu Asn Lys Ala Gln Arg Ala Leu Gln Leu Ala Val Cys Arg
370 375 380

Arg Cys Pro Arg Ala Tyr His Arg Glu Cys Leu Pro Arg Asp Leu Ser

-continued

```
385                 390                 395                 400

Phe Gly Thr Lys Asp Lys Asp Gly Asn Gln Arg Ala Trp Lys Leu Ser
                405                 410                 415

Asp Thr Ile Phe Ile Tyr Cys Leu Asp His Glu Ile Asp Lys Asp Thr
            420                 425                 430

Gly Thr Thr Ser Arg Asn His Ile Lys Phe Pro Ala Thr Pro Glu Tyr
        435                 440                 445

Thr Lys Thr Lys Gly Leu Gly Asn Ser Lys Gly Arg Met Thr Gly Lys
    450                 455                 460

Arg Arg Lys Asn Lys Arg Arg Lys Asn Thr Asp Gln Ser Thr Lys Pro
465                 470                 475                 480

Thr Asp Leu Pro Asn Arg Leu Cys Gly Ala Glu Ser Glu Gln Ala Asp
                485                 490                 495

Asn Val Gly Ala Lys Ser Thr Leu Pro Gln Ile Val Val Glu Pro His
            500                 505                 510

Cys Ala Ala Lys His Leu Lys Gly Asp Pro Gln Ile Ala Lys Gln Gly
        515                 520                 525

Val Ala Ala Arg Gln Asn Gly Ala Glu Thr Met Lys Gly His Glu Asn
    530                 535                 540

Gln Phe Gly Ile Ser Phe Cys Val Ala Ser Thr Glu Thr Glu Lys Arg
545                 550                 555                 560

Val Thr Cys Leu Ala Gln Arg Gly Thr Cys Leu Gly Thr Gln Tyr Asp
                565                 570                 575

Gly Pro Ser Thr Lys Gly Met Tyr Asp Cys Ser Val Gln Asp Thr Pro
            580                 585                 590

Met Asp Asp Asp Val Glu Leu Asp Asn Val Ala Cys Ile Ile Ala Val
        595                 600                 605

Asp Lys Tyr Val Asn Gly Arg Gly Lys Thr Gln Glu Asp Tyr Thr Arg
    610                 615                 620

Lys Glu Ala Ala Gln Arg Lys Asp Ser Ser Glu Asn Gln Gly Gln Asn
625                 630                 635                 640

Asp Ala Leu Glu Leu Asp Asn Leu Arg Met Glu Met Gln Ala Asp Glu
                645                 650                 655

Arg Pro Leu Glu Pro Gly Asn Lys Arg Asp Arg Lys Trp Gln Lys Asn
            660                 665                 670

Val Tyr Gly Leu Gly Ser Ala Ser Gly Gln Lys Glu Thr Leu Ser Arg
        675                 680                 685

Arg Glu Asn Pro Arg Ser Asp Arg Gly Met Val His Ser Asn Asp Ser
    690                 695                 700

Lys Thr Ile Tyr Tyr Arg Lys Gly Gly Thr Glu Val Asp Asn Val Asp
705                 710                 715                 720

Asp His Pro Leu Glu Lys Gln Asp His Gln Asp Thr Ser Ser Asp Gly
                725                 730                 735

Ser Lys Lys Arg Ser Arg Pro Val Asp Asn Ala Ser Gly Gly Asn Arg
            740                 745                 750

Pro Tyr Leu Asp Glu Asn Lys Lys Arg Asn Leu Arg Glu Asp Gly Arg
        755                 760                 765

Tyr Ala His Tyr Glu Asp Trp Arg Ser Glu Arg Asn Thr Ala Ala Asp
    770                 775                 780

Thr Ser Gly Tyr Lys Ala Gln Ser Glu Glu Lys Pro Val Trp Thr Asn
785                 790                 795                 800

Thr Arg Thr Gly Ser Arg Glu His Ser Leu Asp Arg Gln Arg Ile Glu
                805                 810                 815
```

```
Cys Gly Asp Ser Tyr Arg Gly Thr Tyr Asn Asn Arg Gln Arg His Glu
            820                 825                 830

Trp Leu His Pro His Ala Ser Gly Asn Ser Ser Arg Ile Gly Trp Asp
        835                 840                 845

Asp Arg Arg Gln Trp Ser Ser Ser Arg Ser Pro Phe Pro Ser Ala Glu
    850                 855                 860

Phe Gly Gly Asp Arg Ser Cys Ser Arg Ala His Pro Arg Gly Ser Lys
865                 870                 875                 880

Tyr Arg Thr Gly Gly Arg His Asp His Pro Gln Tyr Leu Gly Leu Gly
                885                 890                 895

Thr Pro Gln His Gly Thr Ser Arg Pro His His Thr Met Gly Trp Asp
            900                 905                 910

Arg Asp Thr Phe His Asp His Gln His Gly Arg Arg Pro Pro His His
        915                 920                 925

Thr Met Gly Trp Asp Arg Ala Pro Phe Arg Asp His Gln His Gly Glu
    930                 935                 940

Tyr Asp Asp Ser Arg Tyr Gly Glu Tyr Asp Ala Thr Asp Asn Gly Pro
945                 950                 955                 960

Asp Ser Ala His Arg Pro Tyr Thr Ala Ala Gly Val Ala Gly Arg Ser
                965                 970                 975

Ala Pro Ser Tyr Gln Leu Ala Gly Gly Tyr Gly Glu Gly Ser Arg Ala
            980                 985                 990

Trp Arg Pro Val Thr Asp Lys Tyr  Ala Pro Trp Pro Leu  Pro
        995                 1000                1005
```

<210> SEQ ID NO 4
<211> LENGTH: 3021
<212> TYPE: DNA
<213> ORGANISM: Zea mays

<400> SEQUENCE: 4

```
atgtttgatg atgatgatga tggagtggac ccacaaattg aggatgtcaa cagatactac      60

tttgaggatg gtgaagagaa accagtttgt ttcagtatct tgcctttcca gtttggtgag     120

gacgatagcg aggcagtttt cctcagaaag gatgttttct tgtgtggatt tgtggataaa     180

aatcttcctg tgtacaagga ggtggtagct tggaagataa ggcttgacag tgagcatccc     240

aacatctatg tgctttctat tgagcacaag tggataaagc tgttgaaacc acgaaaatgc     300

tatggagaca ttgttcgatc aacattgatt acggtgcaaa tgctccactt ttttgggaga     360

ggggagcaaa gaagtttgaa tcacctttgg gatcaccttg atgaagtttt tggtaaatac     420

aatcctaaac ccgtggagga tgacttgatg aagcaccata ccctaatcaa gttgtttgta     480

gagaaagatc aaaccttgat gaagtcaaag attcttcaaa ggctcattga gaatggcttt     540

aagagaacta aaaaggcctt aggtatggaa gcacaatcca ttgttagtga cgggtggcgt     600

gctagaaaaa atgatgataa caattatggt aacaaagatg acagtggtga tgattgtgat     660

ggtgatggta gcagtgatga tggtgatggc agcagtgatg atgatgttac cgatcaaata     720

tgtgcgctat gtgatgatgg aggacatttg cttagctgtg acggtccatg caagaggtct     780

ttccacccca caaagaaaga tggcagagaa tctaaatgtg aaagtcttca ttacacttca     840

gcagaagtaa agagaattgg tacttatcta tgtgcaaact gcaaaaaataa gcaacaccaa     900

tgttttagat gtggagagct tgaaccatcc catgggccaa atgctaaggt ctttcaatgc     960

aatcaagcat cttgtggata tttttaccac cctaagtgca ttgcacaatt attggatcct    1020
```

```
aatgccactg atggtgagtt ggaaagaagg attatgtcgg gaatgtcatt tccgtgcccc   1080

atacattggt gtttcaaatg tggccacatg gagaacaaag ctcaaagagc acttcagctt   1140

gcagtgtgta gacgctgtcc aagagcatat cacagggaat gccttccaag ggacttatcc   1200

tttggaacaa aggacaagga tggtaaccaa cgcgcttgga agctttccga cacaattttc   1260

atttactgcc tagatcatga aatagacaag gatactggca caactagtag gaaccatata   1320

aaatttccag ctacacctga atacaccaaa acaaaagggc ttggtaacag caaatgaagg   1380

atgactggca aaaggagaaa gaacaaaagg agaaagaaca ctgaccaatc aacaaaacct   1440

acagatttgc caaacaggtt gtgtggagca gaaagtgagc aagctgacaa tgtaggtgca   1500

aaaagcacat tgccccagat tgttgtagag cctcactgtg cagcaaagca cttgaagggt   1560

gatccacaaa ttgccaaaca gggtgttgct gctcgtcaaa atggtgcaga aactatgaaa   1620

gggcatgaaa atcaatttgg catttcattt tgtgttgcaa gtactgaaac agagaagagg   1680

gtaacatgtt tggcacaaag ggggacatgt ttagggacac aatatgatgg gccatcaacc   1740

aagggcatgt atgattgttc tgttcaggac accccaatgg acgacgatgt tgagttggat   1800

aatgtggcct gcataatcgc ggtggataaa tatgtcaata ggaggaggaa aacacaagag   1860

gactacacta gaaaagaagc tgctcagcgc aaagactcga gtgaaaatca agggcagaat   1920

gatgctctag agctagacaa cctccggatg gagatgcaag ctgacaaacg tccgttagaa   1980

ccaggaaaca agagggacag gaagtggcag aaaaatgcat atggactcgg atcagcttcg   2040

ggacagaagg aaaccttgtc caggagagaa aatccaccgt cagatagagg gatggtccac   2100

agtaacgaca gcaaaacaat ttattacagg aagggtggga cggaagtcga taatgttgat   2160

gaccaccctt tagaaaagca agaccaccag gatacatcaa gtgacggatc taaaaagaga   2220

agccgatctg tggacaacgc atctggtggc aacagaccat acttggatga gagcaagaag   2280

cgtaatctca gagaagatgg aagatatgct cattatgaag actggagaag tgaaaggaat   2340

acagcagcag acacgtctgg atataaggcc caatcagaag agaagcctgt atggacaaac   2400

actcgaacag gatcaaggga gcattcactg gacaggcaaa ggatagagtg cggtgacagc   2460

tatcgtggaa cctataacaa tagacaaaga catgaatggc tgcacccgca cgctagtggt   2520

aattcctcga gaattggttg ggatgacagg aggcagtgga gttcatctcg gtcaccattt   2580

ccttcggctg aatttggtgg tgaccgttcc tgttctcgtg cccatccgag aggttctaaa   2640

tacagaaccg gcgggaggca tgatcacccc cagtacctgg gactgggaac acctcaacat   2700

ggtacaagta gaccgcacca cacaatgggc tgggacaggg acaccttcca tgatcaccag   2760

catggcagaa gaccgccgca ccacacaatg ggctgggaca gggccccctt ccgtgatcac   2820

cagcatggcg aatacgacga ctccaggtat ggtgaatatg atgcaactga caatggtcct   2880

gacagcgcgc atcgacccta cacggctgct ggcgtggctg gacgttcagc accgagttat   2940

cagcttgctg gtggttatgg agagggatca agggcttggc ggccagttac ggacaagtac   3000

gccccatggc ccttgccttg a                                             3021
```

<210> SEQ ID NO 5
<211> LENGTH: 1005
<212> TYPE: PRT
<213> ORGANISM: Zea mays

<400> SEQUENCE: 5

```
Met Phe Asp Asp Asp Asp Asp Gly Val Asp Pro Gln Ile Glu Asp Val
1               5                   10                  15
```

-continued

```
Asn Arg Tyr Tyr Phe Glu Asp Gly Glu Glu Lys Pro Val Cys Phe Ser
            20                  25                  30

Ile Leu Pro Phe Gln Phe Gly Glu Asp Asp Ser Glu Ala Val Phe Leu
        35                  40                  45

Arg Lys Asp Val Phe Leu Cys Gly Phe Val Asp Lys Asn Leu Pro Val
    50                  55                  60

Tyr Lys Glu Val Val Ala Trp Lys Ile Arg Leu Asp Ser Glu His Pro
65                  70                  75                  80

Asn Ile Tyr Val Leu Ser Ile Glu His Lys Trp Ile Lys Leu Leu Lys
                85                  90                  95

Pro Arg Lys Cys Tyr Gly Asp Ile Val Arg Ser Thr Leu Ile Thr Val
            100                 105                 110

Gln Met Leu His Phe Phe Gly Arg Gly Glu Gln Arg Ser Leu Asn His
        115                 120                 125

Leu Trp Asp His Leu Asp Glu Val Phe Gly Lys Tyr Asn Pro Lys Pro
    130                 135                 140

Val Glu Asp Asp Leu Met Lys His His Thr Leu Ile Lys Leu Phe Val
145                 150                 155                 160

Glu Lys Asp Gln Thr Leu Met Lys Ser Lys Ile Leu Gln Arg Leu Ile
                165                 170                 175

Glu Asn Gly Phe Lys Arg Thr Lys Lys Ala Leu Gly Met Glu Ala Gln
            180                 185                 190

Ser Ile Val Ser Asp Gly Trp Arg Ala Arg Lys Asn Asp Asp Asn Asn
        195                 200                 205

Tyr Gly Asn Lys Asp Asp Ser Gly Asp Asp Cys Asp Gly Asp Gly Ser
    210                 215                 220

Ser Asp Asp Gly Asp Gly Ser Ser Asp Asp Asp Val Thr Asp Gln Ile
225                 230                 235                 240

Cys Ala Leu Cys Asp Asp Gly Gly His Leu Leu Ser Cys Asp Gly Pro
                245                 250                 255

Cys Lys Arg Ser Phe His Pro Thr Lys Lys Asp Gly Arg Glu Ser Lys
            260                 265                 270

Cys Glu Ser Leu His Tyr Thr Ser Ala Glu Val Lys Arg Ile Gly Thr
        275                 280                 285

Tyr Leu Cys Ala Asn Cys Lys Asn Lys Gln His Gln Cys Phe Arg Cys
    290                 295                 300

Gly Glu Leu Glu Pro Ser His Gly Pro Asn Ala Lys Val Phe Gln Cys
305                 310                 315                 320

Asn Gln Ala Ser Cys Gly Tyr Phe Tyr His Pro Lys Cys Ile Ala Gln
                325                 330                 335

Leu Leu Asp Pro Asn Ala Thr Asp Gly Glu Leu Glu Arg Arg Ile Met
            340                 345                 350

Ser Gly Met Ser Phe Pro Cys Pro Ile His Trp Cys Phe Lys Cys Gly
        355                 360                 365

His Met Glu Asn Lys Ala Gln Arg Ala Leu Gln Leu Ala Val Cys Arg
    370                 375                 380

Arg Cys Pro Arg Ala Tyr His Arg Glu Cys Leu Pro Arg Asp Leu Ser
385                 390                 395                 400

Phe Gly Thr Lys Asp Lys Asp Gly Asn Gln Arg Ala Trp Lys Leu Ser
                405                 410                 415

Asp Thr Ile Phe Ile Tyr Cys Leu Asp His Glu Ile Asp Lys Asp Thr
            420                 425                 430

Gly Thr Thr Ser Arg Asn His Ile Lys Phe Pro Ala Thr Pro Glu Tyr
```

```
        435                 440                 445

Thr Lys Thr Lys Gly Leu Gly Asn Ser Lys Arg Met Thr Gly Lys Arg
    450                 455                 460

Arg Lys Asn Lys Arg Arg Lys Asn Thr Asp Gln Ser Thr Lys Pro Thr
465                 470                 475                 480

Asp Leu Pro Asn Arg Leu Cys Gly Ala Glu Ser Glu Gln Ala Asp Asn
                485                 490                 495

Val Gly Ala Lys Ser Thr Leu Pro Gln Ile Val Val Glu Pro His Cys
            500                 505                 510

Ala Ala Lys His Leu Lys Gly Asp Pro Gln Ile Ala Lys Gln Gly Val
        515                 520                 525

Ala Ala Arg Gln Asn Gly Ala Glu Thr Met Lys Gly His Glu Asn Gln
    530                 535                 540

Phe Gly Ile Ser Phe Cys Val Ala Ser Thr Glu Thr Glu Lys Arg Val
545                 550                 555                 560

Thr Cys Leu Ala Gln Arg Gly Thr Cys Leu Gly Thr Gln Tyr Asp Gly
                565                 570                 575

Pro Ser Thr Lys Gly Met Tyr Asp Cys Ser Val Gln Asp Thr Pro Met
            580                 585                 590

Asp Asp Asp Val Glu Leu Asp Asn Val Ala Cys Ile Ile Ala Val Asp
        595                 600                 605

Lys Tyr Val Asn Arg Arg Arg Lys Thr Gln Glu Asp Tyr Thr Arg Lys
    610                 615                 620

Glu Ala Ala Gln Arg Lys Asp Ser Ser Glu Asn Gln Gly Gln Asn Asp
625                 630                 635                 640

Ala Leu Glu Leu Asp Asn Leu Arg Met Glu Met Gln Ala Asp Lys Arg
                645                 650                 655

Pro Leu Glu Pro Gly Asn Lys Arg Asp Arg Lys Trp Gln Lys Asn Ala
            660                 665                 670

Tyr Gly Leu Gly Ser Ala Ser Gly Gln Lys Glu Thr Leu Ser Arg Arg
        675                 680                 685

Glu Asn Pro Pro Ser Asp Arg Gly Met Val His Ser Asn Asp Ser Lys
    690                 695                 700

Thr Ile Tyr Tyr Arg Lys Gly Gly Thr Glu Val Asp Asn Val Asp Asp
705                 710                 715                 720

His Pro Leu Glu Lys Gln Asp His Gln Asp Thr Ser Ser Asp Gly Ser
                725                 730                 735

Lys Lys Arg Ser Arg Ser Val Asp Asn Ala Ser Gly Gly Asn Arg Pro
            740                 745                 750

Tyr Leu Asp Glu Ser Lys Lys Arg Asn Leu Arg Glu Asp Gly Arg Tyr
        755                 760                 765

Ala His Tyr Glu Asp Trp Arg Ser Glu Arg Asn Thr Ala Ala Asp Thr
    770                 775                 780

Ser Gly Tyr Lys Ala Gln Ser Glu Glu Lys Pro Val Trp Thr Asn Thr
785                 790                 795                 800

Arg Thr Gly Ser Arg Glu His Ser Leu Asp Arg Gln Arg Ile Glu Cys
                805                 810                 815

Gly Asp Ser Tyr Arg Gly Thr Tyr Asn Asn Arg Gln Arg His Glu Trp
            820                 825                 830

Leu His Pro His Ala Ser Gly Asn Ser Ser Arg Ile Gly Trp Asp Asp
        835                 840                 845

Arg Arg Gln Trp Ser Ser Ser Arg Ser Pro Phe Pro Ser Ala Glu Phe
    850                 855                 860
```

-continued

```
Gly Gly Asp Arg Ser Cys Ser Arg Ala His Pro Arg Gly Ser Lys Tyr
865                 870                 875                 880

Arg Thr Gly Gly Arg His Asp His Pro Gln Tyr Leu Gly Leu Gly Thr
                885                 890                 895

Pro Gln His Gly Thr Ser Arg Pro His His Thr Met Gly Trp Asp Arg
            900                 905                 910

Asp Thr Phe His Asp His Gln His Gly Arg Arg Pro Pro His His Thr
        915                 920                 925

Met Gly Trp Asp Arg Ala Pro Phe Arg Asp His Gln His Gly Glu Tyr
    930                 935                 940

Asp Asp Ser Arg Tyr Gly Glu Tyr Asp Ala Thr Asp Asn Gly Pro Asp
945                 950                 955                 960

Ser Ala His Arg Pro Tyr Thr Ala Ala Gly Val Ala Gly Arg Ser Ala
                965                 970                 975

Pro Ser Tyr Gln Leu Ala Gly Gly Tyr Gly Glu Gly Ser Arg Ala Trp
            980                 985                 990

Arg Pro Val Thr Asp Lys Tyr Ala  Pro Trp Pro Leu Pro
        995                 1000                1005
```

<210> SEQ ID NO 6
<211> LENGTH: 3021
<212> TYPE: DNA
<213> ORGANISM: Zea mays

<400> SEQUENCE: 6

```
atgtttgatg atgatgatga tggagtggac ccacaaattg aggatgtcaa cagatactac      60

tttgaggatg gtgaagagaa accagtttgt ttcagtatct tgcctttcca gtttggtgag     120

gacgatagcg aggcagtttt cctcagaaag gatgttttct tgtgtggatt tgtggataaa     180

aatcttcctg tgtacaagga ggtggtagct tggaagataa ggcttgacag tgagcatccc     240

aacatctatg tgctttctat tgagcacaag tggataaagc tgttgaaacc acgaaaatgc     300

tatggagaca ttgttcgatc aacattgatt acggtgcaaa tgctccactt ttttgggaga     360

ggggagcaaa gaagtttgaa tcacctttgg gatcaccttg atgaagtttt tggtaaatcc     420

aatcctaaac ccgtggagga tgacttgatg aagcaccata ccctaatcaa gttgtttgta     480

gagaaagatc aaaccttgat gaagtcaaag attcttcaaa ggctcattga gaatggcttt     540

aagagaacta aaaaggcctt aggtatggaa gcacaatcca ttgttagtga cgggtggcgt     600

gctagaaaaa atgatgataa caattatggt aacaaagatg acagtggtga tgattgtgat     660

ggtgatggta gcagtgatga tggtgatggc agcagtgatg atgatgttac cgatcaaata     720

tgtgcgctat gtgatgatgg aggacatttg cttagctgtg acggtccatg caagaggtct     780

ttccacccca caaagaaaga tggcagagaa tctaaatgtg aaagtcttca ttacacttca     840

gcagaagtaa agagaattgg tacttatcta tgtgcaaact gcaaaaataa gcaacaccaa     900

tgttttagat gtggagagct tgaaccatcc catgggccaa atgctaaggt ctttcaatgc     960

aatcaagcat cttgtggata tttttaccac cctaagtgca ttgcacaatt attggatcct    1020

aatgccactg atggtgagtt ggaaagaagg attatgtcgg gaatgtcatt tccgtgcccc    1080

atacattggt gtttcaaatg tggccacatg gagaacaaag ctcaaagagc acttcagctt    1140

gcagtgtgta gacgctgtcc aagagcatat cacagggaat gccttccaag ggacttatcc    1200

tttggaacaa aggacaagga tggtaaccaa cgcgcttgga agctttccga cacaattttc    1260

atttactgcc tagatcatga aatagacaag gatactggca caactagtag gaaccatata    1320
```

```
aaatttccag ctacacctga atacaccaaa acaaaagggc ttggtaacag caaatgaagg   1380

atgactggca aaaggagaaa gaacaaaagg agaaagaaca ctgaccaatc aacaaaacct   1440

acagatttgc caaacaggtt gtgtggagca gaaagtgagc aagctgacaa tgtaggtgca   1500

aaaagcacat tgccccagat tgttgtagag cctcactgtg cagcaaagca cctgaagggt   1560

gatccacaaa ttgccaaaca gggtgttgct gctcgtcaaa atggtgcaga aactatgaaa   1620

gggcatgaaa atcaatttgg catttcattt tgtgttgcaa gtactgaaac agagaagagg   1680

gtaacatgtt tggcacaaag ggggacatgt ttagggacac aatatgatgg gccatcaacc   1740

aagggcatgt atgattgttc tgttcaggac accccaatgg acgacgatgt tgagttggat   1800

aatgtggcct gcataatcgc ggtggataaa tatgtcaatg agagggagaa aacacaagag   1860

gactacacta gaaaagaagc tgctcagcgc aaagactcga gtgaaaatca agggcagaat   1920

gatgctctag agctagacaa cctccggatg gagatgcaag ctgacaaacg tccgttagaa   1980

ccaggaaaca agagggacag gaagtggcag aaaaatgcat atggactcgg atcagcttcg   2040

ggacagaagg aaaccttgtc caggagagaa aatccaccgt cagatagagg gatggtccac   2100

agtaacgaca gcaaaacaat ttattacagg aagggtggga cggaagtcga taatgttgat   2160

gaccaccctt tagaaaagca agaccaccag gatacatcaa gtgacggatc taaaaagaga   2220

agccgatctg tggacaacgc atctggtggc aacagaccat acttggatga gagcaagaag   2280

cgtaatctca gagaagatgg aagatatgct cattatgaag actggagaag tgaaaggaat   2340

acagcagcag acacgtctgg atataaggcc caatcagaag agaagcctgt atggacaaac   2400

actcgaacag gatcaaggga gcattcactg gacaggcaaa ggatagagtg tggtgacagc   2460

tatcgtggaa cctataacaa tagacaaaga catgaatggc cgcacccgca cgctagtggt   2520

aattcctcga gaattggttg ggatgacagg aggcagtgga gttcatctcg gtcaccattt   2580

ccttcggctg aatttggtgg tgaccgttcc tgttctcgtg cccatccgag aggttctaaa   2640

tacagaaccg gcgggaggca tgatcacccc cagtacctgg gactgggaac acctcaacat   2700

ggtacaagta gaccgcacca cacaatgggc tgggacaggg acacctccca tgatcaccag   2760

catggcagaa gaccgccgca ccacacaatg ggctgggaca gggcccccctt ccgtgatcac   2820

cagcatggcg aataccacga ctccaggtat ggtgaatatg atgcaactga caatggtcct   2880

gacagcgcgc atcgacccta cacggctgct ggcgtggctg gacgttcagc accgagttat   2940

cagcttgctg gtggttatgg agagggatca agggcttggc ggccagttac ggacaagtac   3000

gccccatggc ccttgccttg a                                               3021
```

<210> SEQ ID NO 7
<211> LENGTH: 1005
<212> TYPE: PRT
<213> ORGANISM: Zea mays

<400> SEQUENCE: 7

```
Met Phe Asp Asp Asp Asp Asp Gly Val Asp Pro Gln Ile Glu Asp Val
1               5                   10                  15

Asn Arg Tyr Tyr Phe Glu Asp Gly Glu Glu Lys Pro Val Cys Phe Ser
            20                  25                  30

Ile Leu Pro Phe Gln Phe Gly Glu Asp Asp Ser Glu Ala Val Phe Leu
        35                  40                  45

Arg Lys Asp Val Phe Leu Cys Gly Phe Val Asp Lys Asn Leu Pro Val
    50                  55                  60
```

-continued

```
Tyr Lys Glu Val Val Ala Trp Lys Ile Arg Leu Asp Ser Glu His Pro
65                  70                  75                  80

Asn Ile Tyr Val Leu Ser Ile Glu His Lys Trp Ile Lys Leu Leu Lys
                85                  90                  95

Pro Arg Lys Cys Tyr Gly Asp Ile Val Arg Ser Thr Leu Ile Thr Val
            100                 105                 110

Gln Met Leu His Phe Phe Gly Arg Gly Glu Gln Arg Ser Leu Asn His
        115                 120                 125

Leu Trp Asp His Leu Asp Glu Val Phe Gly Lys Ser Asn Pro Lys Pro
    130                 135                 140

Val Glu Asp Asp Leu Met Lys His His Thr Leu Ile Lys Leu Phe Val
145                 150                 155                 160

Glu Lys Asp Gln Thr Leu Met Lys Ser Lys Ile Leu Gln Arg Leu Ile
                165                 170                 175

Glu Asn Gly Phe Lys Arg Thr Lys Lys Ala Leu Gly Met Glu Ala Gln
            180                 185                 190

Ser Ile Val Ser Asp Gly Trp Arg Ala Arg Lys Asn Asp Asp Asn Asn
        195                 200                 205

Tyr Gly Asn Lys Asp Asp Ser Gly Asp Asp Cys Asp Gly Asp Gly Ser
    210                 215                 220

Ser Asp Asp Gly Asp Gly Ser Ser Asp Asp Asp Val Thr Asp Gln Ile
225                 230                 235                 240

Cys Ala Leu Cys Asp Asp Gly Gly His Leu Leu Ser Cys Asp Gly Pro
                245                 250                 255

Cys Lys Arg Ser Phe His Pro Thr Lys Lys Asp Gly Arg Glu Ser Lys
            260                 265                 270

Cys Glu Ser Leu His Tyr Thr Ser Ala Glu Val Lys Arg Ile Gly Thr
        275                 280                 285

Tyr Leu Cys Ala Asn Cys Lys Asn Lys Gln His Gln Cys Phe Arg Cys
    290                 295                 300

Gly Glu Leu Glu Pro Ser His Gly Pro Asn Ala Lys Val Phe Gln Cys
305                 310                 315                 320

Asn Gln Ala Ser Cys Gly Tyr Phe Tyr His Pro Lys Cys Ile Ala Gln
                325                 330                 335

Leu Leu Asp Pro Asn Ala Thr Asp Gly Glu Leu Glu Arg Arg Ile Met
            340                 345                 350

Ser Gly Met Ser Phe Pro Cys Pro Ile His Trp Cys Phe Lys Cys Gly
        355                 360                 365

His Met Glu Asn Lys Ala Gln Arg Ala Leu Gln Leu Ala Val Cys Arg
    370                 375                 380

Arg Cys Pro Arg Ala Tyr His Arg Glu Cys Leu Pro Arg Asp Leu Ser
385                 390                 395                 400

Phe Gly Thr Lys Asp Lys Asp Gly Asn Gln Arg Ala Trp Lys Leu Ser
                405                 410                 415

Asp Thr Ile Phe Ile Tyr Cys Leu Asp His Glu Ile Asp Lys Asp Thr
            420                 425                 430

Gly Thr Thr Ser Arg Asn His Ile Lys Phe Pro Ala Thr Pro Glu Tyr
        435                 440                 445

Thr Lys Thr Lys Gly Leu Gly Asn Ser Lys Arg Met Thr Gly Lys Arg
    450                 455                 460

Arg Lys Asn Lys Arg Arg Lys Asn Thr Asp Gln Ser Thr Lys Pro Thr
465                 470                 475                 480

Asp Leu Pro Asn Arg Leu Cys Gly Ala Glu Ser Glu Gln Ala Asp Asn
```

-continued

```
                485                 490                 495

Val Gly Ala Lys Ser Thr Leu Pro Gln Ile Val Val Glu Pro His Cys
            500                 505                 510

Ala Ala Lys His Leu Lys Gly Asp Pro Gln Ile Ala Lys Gln Gly Val
        515                 520                 525

Ala Ala Arg Gln Asn Gly Ala Glu Thr Met Lys Gly His Glu Asn Gln
    530                 535                 540

Phe Gly Ile Ser Phe Cys Val Ala Ser Thr Glu Thr Glu Lys Arg Val
545                 550                 555                 560

Thr Cys Leu Ala Gln Arg Gly Thr Cys Leu Gly Thr Gln Tyr Asp Gly
                565                 570                 575

Pro Ser Thr Lys Gly Met Tyr Asp Cys Ser Val Gln Asp Thr Pro Met
            580                 585                 590

Asp Asp Asp Val Glu Leu Asp Asn Val Ala Cys Ile Ile Ala Val Asp
        595                 600                 605

Lys Tyr Val Asn Glu Arg Glu Lys Thr Gln Glu Asp Tyr Thr Arg Lys
    610                 615                 620

Glu Ala Ala Gln Arg Lys Asp Ser Ser Glu Asn Gln Gly Gln Asn Asp
625                 630                 635                 640

Ala Leu Glu Leu Asp Asn Leu Arg Met Glu Met Gln Ala Asp Lys Arg
                645                 650                 655

Pro Leu Glu Pro Gly Asn Lys Arg Asp Arg Lys Trp Gln Lys Asn Ala
            660                 665                 670

Tyr Gly Leu Gly Ser Ala Ser Gly Gln Lys Glu Thr Leu Ser Arg Arg
        675                 680                 685

Glu Asn Pro Pro Ser Asp Arg Gly Met Val His Ser Asn Asp Ser Lys
    690                 695                 700

Thr Ile Tyr Tyr Arg Lys Gly Gly Thr Glu Val Asp Asn Val Asp Asp
705                 710                 715                 720

His Pro Leu Glu Lys Gln Asp His Gln Asp Thr Ser Ser Asp Gly Ser
                725                 730                 735

Lys Lys Arg Ser Arg Ser Val Asp Asn Ala Ser Gly Gly Asn Arg Pro
            740                 745                 750

Tyr Leu Asp Glu Ser Lys Lys Arg Asn Leu Arg Glu Asp Gly Arg Tyr
        755                 760                 765

Ala His Tyr Glu Asp Trp Arg Ser Glu Arg Asn Thr Ala Ala Asp Thr
    770                 775                 780

Ser Gly Tyr Lys Ala Gln Ser Glu Glu Lys Pro Val Trp Thr Asn Thr
785                 790                 795                 800

Arg Thr Gly Ser Arg Glu His Ser Leu Asp Arg Gln Arg Ile Glu Cys
                805                 810                 815

Gly Asp Ser Tyr Arg Gly Thr Tyr Asn Asn Arg Gln Arg His Glu Trp
            820                 825                 830

Pro His Pro His Ala Ser Gly Asn Ser Ser Arg Ile Gly Trp Asp Asp
        835                 840                 845

Arg Arg Gln Trp Ser Ser Ser Arg Ser Pro Phe Pro Ser Ala Glu Phe
    850                 855                 860

Gly Gly Asp Arg Ser Cys Ser Arg Ala His Pro Arg Gly Ser Lys Tyr
865                 870                 875                 880

Arg Thr Gly Gly Arg His Asp His Pro Gln Tyr Leu Gly Leu Gly Thr
                885                 890                 895

Pro Gln His Gly Thr Ser Arg Pro His His Thr Met Gly Trp Asp Arg
            900                 905                 910
```

-continued

Asp Thr Ser His Asp His Gln His Gly Arg Arg Pro Pro His His Thr
        915                 920                 925

Met Gly Trp Asp Arg Ala Pro Phe Arg Asp His Gln His Gly Glu Tyr
    930                 935                 940

His Asp Ser Arg Tyr Gly Glu Tyr Asp Ala Thr Asp Asn Gly Pro Asp
945                 950                 955                 960

Ser Ala His Arg Pro Tyr Thr Ala Ala Gly Val Ala Gly Arg Ser Ala
                965                 970                 975

Pro Ser Tyr Gln Leu Ala Gly Gly Tyr Gly Glu Gly Ser Arg Ala Trp
            980                 985                 990

Arg Pro Val Thr Asp Lys Tyr Ala  Pro Trp Pro Leu Pro
        995                 1000                1005

<210> SEQ ID NO 8
<211> LENGTH: 3021
<212> TYPE: DNA
<213> ORGANISM: Zea mays

<400> SEQUENCE: 8
atgtttgatg atgatgatga tggagtggac ccacaaattg aggatgtcaa cagatactac     60
tttgaggatg gtgaagagaa accagtttgt ttcagtatct tgcctttcca gtttggtgag    120
gacgatagcg aggcagtttt cctcagaaag gatgttttct tgtgtggatt tgtggataaa    180
aatcttcctg tgtacaagga ggtggtagct tggaagataa ggcttgacag tgagcatccc    240
aacatctatg tgctttctat tgagcacaag tggataaagc tgttgaaacc acgaaaatgc    300
tatggagaca ttgttcgatc aacattgatt acggtgcaaa tgctccactt ttttgggaga    360
ggggagcaaa gaagtttgaa tcacctttgg gatcaccttg atgaagtttt tggtaaatcc    420
aatcctaaac ccgtggagga tgacttgatg aagcaccata ccctaatcaa gttgtttgta    480
gagaaagatc aaaccttgat gaagtcaaag attcttcaaa ggctcattga gaatggcttt    540
aagagaacta aaaaggcctt aggtatggaa gcacaatcca ttgttagtga cgggtggcgt    600
gctagaaaaa atgatgataa caattatggt aacaaagatg acagtggtga tgattgtgat    660
ggtgatggta gcagtgatga tggtgatggc agcagtgatg atgatgttac cgatcaaata    720
tgtgcgctat gtgatgatgg aggacatttg cttagctgtg acggtccatg caagaggtct    780
ttccacccca caaagaaaga tggcagagaa tctaaatgtg aaagtcttca ttacacttca    840
gcagaagtaa agagaattgg tacttatcta tgtgcaaact gcaaaaataa gcaacaccaa    900
tgttttagat gtggagagct tgaaccatcc catgggccaa atgctaaggt ctttcaatgc    960
aatcaagcat cttgtggata tttttaccac cctaagtgca ttgcacaatt attggatcct   1020
aatgccactg atggtgagtt ggaaagaagg attatgtcgg gaatgtcatt tccgtgcccc   1080
atacattggt gtttcaaatg tggccacatg gagaacaaag ctcaaagagc acttcagctt   1140
gcagtgtgta gacgctgtcc aagagcatat cacagggaat gccttccaag ggacttatcc   1200
tttggaacaa aggacaagga tggtaaccaa cgcgcttgga agctttccga cacaattttc   1260
atttactgcc tagatcatga aatagacaag gatactggca caactagtag gaaccatata   1320
aaatttccag ctacacctga atacaccaaa acaaaagggc ttggtaacag caaagtaagg   1380
atgactggca aaaggagaaa gaacaaaagg agaaagaaca ctgaccaatc aacaaaacct   1440
acagatttgc caaacaggtt gtgtggagca gaaagtgagc aagctgacaa tgtaggtgca   1500
aaaagcacat tgccccagat tgttgtagag cctcactgtg cagcaaagca ctcgaagggt   1560

```
gatccacaaa ttgccaaaca gggtgttgct gctcgtcaaa atggtgcaga aactatgaaa   1620
gggcatgaaa atcaatttgg catttcattt tgtgttgcaa gtactgaaac agagaagagg   1680
gtaacatgtt tggcacaaag ggggacatgt ttagggacac aatatgatgg gccatcaacc   1740
aagggcatgt atgattgttc tgttcaggac accccaatgg acgacgatgt tgagttggat   1800
aatgtggcct gcataatcgc ggtggataaa tatgtcaatg gaaggggaaa aacacaagag   1860
gactacacta gaaaagaagc tgctcagcgc aaagactcga gtgaaaatca agggcagaat   1920
gatgctctag agctagacaa cctccggatg gagatgcaag ctgacaaacg tccgttagaa   1980
ccaggaaaca agagggacag gaagtggcag aaaaatgcat atggactcgg atcagcttcg   2040
ggacagaagg aaaccttgtc caggagagaa aatccaccgt cagatagagg gatggtccac   2100
agtaacgaca gcaaaacaat ttattacagg aagggtggga cggaagtcga taatgttgat   2160
gaccaccctt tagaaaagca agaccaccag gatacatcaa gtgacggatc taaaaagaga   2220
agccgaccag tggacaacgc atctggtggc aacagaccat acttggatga gaacaagaag   2280
cgtaatttct gagaagatgg aagatatgct cattatgaag actggagaag tgaaaggaat   2340
acagcagcag acacgtctgg atataaggcc caatcagaag agaagcctgt atggacaaac   2400
actcgaacag gatcaaggga gcattcactg gacaggcaaa ggatagagtg cggtgacagc   2460
tatcgtggaa cctataacaa tagacaaaga catgaatggc tgcacccgca cgctagtggt   2520
aattcctcga gaattggttg ggatgacagg aggcagtgga gttcatctcg gtcaccattt   2580
ccttcggctg aatttggtgg tgaccgttcc tgttctcgtg cccatccgag aggttctaaa   2640
tacagaaccg gcgggaggca tgatcacccc cagtacctgg gactgggaac acctcaacat   2700
ggtacaagta gaccgcacca cacaatgggc tgggacaggg acaccttcca tgatcaccag   2760
catggcagaa gaccgccgca ccacacaatg ggctgggaca gggccccctt ccgtgatcac   2820
cagcatggcg aatacgacga ctccaggtat ggtgaatatg atgcaactga caatggtcct   2880
gacagcgcgc atcgacccta cacggctgct ggcgtggctg gacgttcagc accgagttat   2940
cagcttgctg gtggttatgg agagggatca agggcttggc ggccagttac ggacaagtac   3000
gccccatggc ccttgccttg a                                               3021
```

```
<210> SEQ ID NO 9
<211> LENGTH: 1005
<212> TYPE: PRT
<213> ORGANISM: Zea mays

<400> SEQUENCE: 9

Met Phe Asp Asp Asp Asp Asp Gly Val Asp Pro Gln Ile Glu Asp Val
1               5                   10                  15

Asn Arg Tyr Tyr Phe Glu Asp Gly Glu Glu Lys Pro Val Cys Phe Ser
            20                  25                  30

Ile Leu Pro Phe Gln Phe Gly Glu Asp Asp Ser Glu Ala Val Phe Leu
        35                  40                  45

Arg Lys Asp Val Phe Leu Cys Gly Phe Val Asp Lys Asn Leu Pro Val
    50                  55                  60

Tyr Lys Glu Val Val Ala Trp Lys Ile Arg Leu Asp Ser Glu His Pro
65                  70                  75                  80

Asn Ile Tyr Val Leu Ser Ile Glu His Lys Trp Ile Lys Leu Leu Lys
                85                  90                  95

Pro Arg Lys Cys Tyr Gly Asp Ile Val Arg Ser Thr Leu Ile Thr Val
            100                 105                 110
```

-continued

```
Gln Met Leu His Phe Phe Gly Arg Gly Glu Gln Arg Ser Leu Asn His
        115                 120                 125

Leu Trp Asp His Leu Asp Glu Val Phe Gly Lys Ser Asn Pro Lys Pro
    130                 135                 140

Val Glu Asp Asp Leu Met Lys His His Thr Leu Ile Lys Leu Phe Val
145                 150                 155                 160

Glu Lys Asp Gln Thr Leu Met Lys Ser Lys Ile Leu Gln Arg Leu Ile
                165                 170                 175

Glu Asn Gly Phe Lys Arg Thr Lys Lys Ala Leu Gly Met Glu Ala Gln
            180                 185                 190

Ser Ile Val Ser Asp Gly Trp Arg Ala Arg Lys Asn Asp Asp Asn Asn
        195                 200                 205

Tyr Gly Asn Lys Asp Asp Ser Gly Asp Asp Cys Asp Gly Asp Gly Ser
    210                 215                 220

Ser Asp Asp Gly Asp Gly Ser Ser Asp Asp Asp Val Thr Asp Gln Ile
225                 230                 235                 240

Cys Ala Leu Cys Asp Asp Gly Gly His Leu Leu Ser Cys Asp Gly Pro
                245                 250                 255

Cys Lys Arg Ser Phe His Pro Thr Lys Lys Asp Gly Arg Glu Ser Lys
            260                 265                 270

Cys Glu Ser Leu His Tyr Thr Ser Ala Glu Val Lys Arg Ile Gly Thr
        275                 280                 285

Tyr Leu Cys Ala Asn Cys Lys Asn Lys Gln His Gln Cys Phe Arg Cys
    290                 295                 300

Gly Glu Leu Glu Pro Ser His Gly Pro Asn Ala Lys Val Phe Gln Cys
305                 310                 315                 320

Asn Gln Ala Ser Cys Gly Tyr Phe Tyr His Pro Lys Cys Ile Ala Gln
                325                 330                 335

Leu Leu Asp Pro Asn Ala Thr Asp Gly Glu Leu Glu Arg Arg Ile Met
            340                 345                 350

Ser Gly Met Ser Phe Pro Cys Pro Ile His Trp Cys Phe Lys Cys Gly
        355                 360                 365

His Met Glu Asn Lys Ala Gln Arg Ala Leu Gln Leu Ala Val Cys Arg
    370                 375                 380

Arg Cys Pro Arg Ala Tyr His Arg Glu Cys Leu Pro Arg Asp Leu Ser
385                 390                 395                 400

Phe Gly Thr Lys Asp Lys Asp Gly Asn Gln Arg Ala Trp Lys Leu Ser
                405                 410                 415

Asp Thr Ile Phe Ile Tyr Cys Leu Asp His Glu Ile Asp Lys Asp Thr
            420                 425                 430

Gly Thr Thr Ser Arg Asn His Ile Lys Phe Pro Ala Thr Pro Glu Tyr
        435                 440                 445

Thr Lys Thr Lys Gly Leu Gly Asn Ser Lys Val Arg Met Thr Gly Lys
    450                 455                 460

Arg Arg Lys Asn Lys Arg Arg Lys Asn Thr Asp Gln Ser Thr Lys Pro
465                 470                 475                 480

Thr Asp Leu Pro Asn Arg Leu Cys Gly Ala Glu Ser Glu Gln Ala Asp
                485                 490                 495

Asn Val Gly Ala Lys Ser Thr Leu Pro Gln Ile Val Val Glu Pro His
            500                 505                 510

Cys Ala Ala Lys His Ser Lys Gly Asp Pro Gln Ile Ala Lys Gln Gly
        515                 520                 525

Val Ala Ala Arg Gln Asn Gly Ala Glu Thr Met Lys Gly His Glu Asn
```

```
    530                 535                 540

Gln Phe Gly Ile Ser Phe Cys Val Ala Ser Thr Glu Thr Glu Lys Arg
545                 550                 555                 560

Val Thr Cys Leu Ala Gln Arg Gly Thr Cys Leu Gly Thr Gln Tyr Asp
                565                 570                 575

Gly Pro Ser Thr Lys Gly Met Tyr Asp Cys Ser Val Gln Asp Thr Pro
            580                 585                 590

Met Asp Asp Asp Val Glu Leu Asp Asn Val Ala Cys Ile Ile Ala Val
        595                 600                 605

Asp Lys Tyr Val Asn Gly Arg Gly Lys Thr Gln Glu Asp Tyr Thr Arg
    610                 615                 620

Lys Glu Ala Ala Gln Arg Lys Asp Ser Ser Glu Asn Gln Gly Gln Asn
625                 630                 635                 640

Asp Ala Leu Glu Leu Asp Asn Leu Arg Met Glu Met Gln Ala Asp Lys
                645                 650                 655

Arg Pro Leu Glu Pro Gly Asn Lys Arg Asp Arg Lys Trp Gln Lys Asn
            660                 665                 670

Ala Tyr Gly Leu Gly Ser Ala Ser Gly Gln Lys Glu Thr Leu Ser Arg
        675                 680                 685

Arg Glu Asn Pro Pro Ser Asp Arg Gly Met Val His Ser Asn Asp Ser
    690                 695                 700

Lys Thr Ile Tyr Tyr Arg Lys Gly Gly Thr Glu Val Asp Asn Val Asp
705                 710                 715                 720

Asp His Pro Leu Glu Lys Gln Asp His Gln Asp Thr Ser Ser Asp Gly
                725                 730                 735

Ser Lys Lys Arg Ser Arg Pro Val Asp Asn Ala Ser Gly Gly Asn Arg
            740                 745                 750

Pro Tyr Leu Asp Glu Asn Lys Lys Arg Asn Phe Glu Asp Gly Arg Tyr
        755                 760                 765

Ala His Tyr Glu Asp Trp Arg Ser Glu Arg Asn Thr Ala Ala Asp Thr
    770                 775                 780

Ser Gly Tyr Lys Ala Gln Ser Glu Glu Lys Pro Val Trp Thr Asn Thr
785                 790                 795                 800

Arg Thr Gly Ser Arg Glu His Ser Leu Asp Arg Gln Arg Ile Glu Cys
                805                 810                 815

Gly Asp Ser Tyr Arg Gly Thr Tyr Asn Asn Arg Gln Arg His Glu Trp
            820                 825                 830

Leu His Pro His Ala Ser Gly Asn Ser Ser Arg Ile Gly Trp Asp Asp
        835                 840                 845

Arg Arg Gln Trp Ser Ser Ser Arg Ser Pro Phe Pro Ser Ala Glu Phe
    850                 855                 860

Gly Gly Asp Arg Ser Cys Ser Arg Ala His Pro Arg Gly Ser Lys Tyr
865                 870                 875                 880

Arg Thr Gly Gly Arg His Asp His Pro Gln Tyr Leu Gly Leu Gly Thr
                885                 890                 895

Pro Gln His Gly Thr Ser Arg Pro His His Thr Met Gly Trp Asp Arg
            900                 905                 910

Asp Thr Phe His Asp His Gln His Gly Arg Arg Pro Pro His His Thr
        915                 920                 925

Met Gly Trp Asp Arg Ala Pro Phe Arg Asp His Gln His Gly Glu Tyr
    930                 935                 940

Asp Asp Ser Arg Tyr Gly Glu Tyr Asp Ala Thr Asp Asn Gly Pro Asp
945                 950                 955                 960
```

Ser Ala His Arg Pro Tyr Thr Ala Ala Gly Val Ala Gly Arg Ser Ala
965 970 975

Pro Ser Tyr Gln Leu Ala Gly Gly Tyr Gly Glu Gly Ser Arg Ala Trp
980 985 990

Arg Pro Val Thr Asp Lys Tyr Ala Pro Trp Pro Leu Pro
995 1000 1005

<210> SEQ ID NO 10
<211> LENGTH: 1297
<212> TYPE: PRT
<213> ORGANISM: Arabidopsis thaliana

<400> SEQUENCE: 10

Met Thr Phe Val Asp Asp Asp Glu Glu Glu Asp Phe Ser Val Pro Gln
1 5 10 15

Ser Ala Ser Asn Tyr Tyr Phe Glu Asp Asp Asp Lys Glu Pro Val Ser
20 25 30

Phe Ala Arg Leu Pro Ile Gln Trp Ser Val Glu Glu Lys Val Asp Gly
35 40 45

Ser Gly Leu Gly Phe Tyr Leu Arg Gly Arg Ser Asp Asn Gly Leu Leu
50 55 60

Pro Leu His Lys Leu Val Lys Ala Trp Arg Tyr Asp Leu Ser Asn Phe
65 70 75 80

Gln Pro Glu Ile Ser Val Leu Thr Lys Asp Asn Ile Trp Ile Lys Leu
85 90 95

Glu Glu Pro Arg Lys Ser Tyr Gly Glu Leu Ile Arg Thr Val Leu Val
100 105 110

Thr Leu His Ser Ile Gln Phe Leu Arg Arg Asn Pro Gln Ala Ser Glu
115 120 125

Lys Ala Leu Trp Glu Lys Leu Thr Arg Ser Leu Arg Ser Tyr Asp Val
130 135 140

Lys Pro Ser Gln Asn Asp Leu Val Asp His Ile Gly Leu Ile Ala Glu
145 150 155 160

Ala Ala Lys Arg Asp Arg Asn Leu Ala Asn Ser Lys Phe Ile Leu Ala
165 170 175

Phe Leu Thr Lys Lys Pro Thr Lys Arg Arg Leu Pro Asp Glu Asp Asn
180 185 190

Ala Lys Asp Asp Phe Ile Val Gly Asp Glu Asp Thr Tyr Val Ala Ser
195 200 205

Asp Glu Asp Glu Leu Asp Asp Glu Asp Asp Asp Phe Phe Glu Ser Val
210 215 220

Cys Ala Ile Cys Asp Asn Gly Gly Glu Ile Leu Cys Cys Glu Gly Ser
225 230 235 240

Cys Leu Arg Ser Phe His Ala Thr Lys Lys Asp Gly Glu Asp Ser Leu
245 250 255

Cys Asp Ser Leu Gly Phe Asn Lys Met Gln Val Glu Ala Ile Gln Lys
260 265 270

Tyr Phe Cys Pro Asn Cys Glu His Lys Ile His Gln Cys Phe Ile Cys
275 280 285

Lys Asn Leu Gly Ser Ser Asp Asn Ser Ser Gly Ala Ala Glu Val Phe
290 295 300

Gln Cys Val Ser Ala Thr Cys Gly Tyr Phe Tyr His Pro His Cys Val
305 310 315 320

Thr Arg Arg Leu Arg Leu Gly Asn Lys Glu Glu Ser Glu Ala Leu Glu

-continued

```
                325                 330                 335

Arg Gln Ile Ile Ala Gly Glu Tyr Thr Cys Pro Leu His Lys Cys Ser
            340                 345                 350

Val Cys Glu Asn Gly Glu Val Lys Thr Asp Ser Asn Leu Gln Phe Ala
        355                 360                 365

Val Cys Arg Arg Cys Pro Lys Ser Tyr His Arg Lys Cys Leu Pro Arg
    370                 375                 380

Glu Ile Ser Phe Glu Asp Ile Glu Asp Glu Asp Ile Leu Thr Arg Ala
385                 390                 395                 400

Trp Asp Gly Leu Leu His Asn Arg Val Leu Ile Tyr Cys Gln Glu His
                405                 410                 415

Glu Ile Asp Glu Glu Leu Leu Thr Pro Val Arg Asp His Val Lys Phe
            420                 425                 430

Pro Phe Thr Glu Glu Gln Lys Val Phe Val Lys Glu Gln Arg Arg Ile
        435                 440                 445

Leu Glu Ser His Val Gly Arg Asp Lys Ala Arg Leu Lys Val Lys Asp
    450                 455                 460

Pro Ala Leu Gln Asp Thr Cys Gly Lys Ala Ser Lys Asn Ser Phe Arg
465                 470                 475                 480

Ser Ser Phe Pro Ser Ser Lys Asp Gly Phe Ser Thr Lys Lys His Gly
                485                 490                 495

Leu Val Ser Ser Val Pro Asp His Ser Arg Lys Arg Lys Asp Ile Asp
            500                 505                 510

Pro Ser Ile Lys His Lys Met Val Pro Gln Lys Ser Gln Lys Met Met
        515                 520                 525

Glu Asp Ser Arg Glu Ala Gly Lys Asn Lys Leu Gly Val Lys Glu Ala
    530                 535                 540

Arg Asp Ala Gly Lys Ser Lys Ile Ser Leu Gly Glu Arg Leu Phe Ser
545                 550                 555                 560

Tyr Thr Gln Glu Pro Asn Pro Val Lys Pro Gly Arg Val Ile Pro Val
                565                 570                 575

Asp Ser Lys His Asn Lys Thr Asp Ser Ile Ala Ser Lys Glu Pro Gly
            580                 585                 590

Ser Glu Ile Pro Thr Leu Asp Asn Asp Ser Gln Arg Arg Leu Leu Ala
        595                 600                 605

Val Met Lys Lys Ala Thr Glu Glu Ile Thr Met Gly Thr Ile Leu Lys
    610                 615                 620

Lys Phe Lys Ile Gln Ser Thr Met Ser Thr His Ser Thr Arg Asn Val
625                 630                 635                 640

Val Asp Lys Thr Ile Thr Met Gly Lys Val Glu Gly Ser Val Gln Ala
                645                 650                 655

Ile Arg Thr Ala Leu Lys Lys Leu Glu Glu Gly Gly Asn Ile Glu Asp
            660                 665                 670

Ala Lys Ala Val Cys Glu Pro Glu Val Leu Ser Gln Ile Leu Lys Trp
        675                 680                 685

Lys Asp Lys Leu Lys Val Tyr Leu Ala Pro Phe Leu His Gly Ala Arg
    690                 695                 700

Tyr Thr Ser Phe Gly Arg His Phe Thr Asn Pro Glu Lys Leu Gln Gln
705                 710                 715                 720

Ile Val Asp Arg Leu His Trp Tyr Ala Asp Asp Gly Asp Met Ile Val
                725                 730                 735

Asp Phe Cys Cys Gly Ser Asn Asp Phe Ser Cys Leu Met Asn Ala Lys
            740                 745                 750
```

```
Leu Glu Glu Thr Gly Lys Lys Cys Leu Tyr Lys Asn Tyr Asp Leu Phe
        755                 760                 765

Pro Ala Lys Asn Asn Phe Asn Phe Glu Arg Lys Asp Trp Met Thr Val
    770                 775                 780

Ser Lys Asp Glu Leu Glu Pro Gly Ser Lys Leu Ile Met Gly Leu Asn
785                 790                 795                 800

Pro Pro Phe Gly Val Asn Ala Ser Leu Ala Asn Lys Phe Ile Thr Lys
                805                 810                 815

Ala Leu Glu Phe Arg Pro Lys Ile Leu Ile Leu Ile Val Pro Pro Glu
            820                 825                 830

Thr Glu Arg Leu Asp Lys Lys Lys Ser Ser Tyr Val Leu Ile Trp Glu
        835                 840                 845

Asp Lys Thr Phe Leu Ser Gly Asn Ser Phe Tyr Leu Pro Gly Ser Val
    850                 855                 860

Asn Glu Glu Asp Lys Gln Leu Glu Asp Trp Asn Leu Val Pro Pro Pro
865                 870                 875                 880

Leu Ser Leu Trp Ser Arg Ser Asp Phe Ala Ala Lys His Lys Lys Ile
                885                 890                 895

Ala Glu Lys His Cys His Leu Ser Arg Asp Val Gly Ser Ser Lys Leu
            900                 905                 910

Lys Ile Val Glu Glu Glu Ala Asn Ala Ser Leu His Pro Leu Gly Ala
        915                 920                 925

Ser Asp Gly Met Cys Asp Asp Ile Pro Met Glu Lys Asp Glu Leu Glu
    930                 935                 940

Val Ala Glu Cys Val Asn Lys Ile Leu Val Ser Glu Lys Ile Asp Thr
945                 950                 955                 960

Val Glu Thr Val Ala Arg Val His Gln Ser Asp His Leu Ser Arg Arg
                965                 970                 975

Ser Gln Leu Lys Lys Glu Gly Lys Thr Lys Asp Tyr Ser Gly Arg Lys
            980                 985                 990

Leu Gly Lys Ser Met Asp Ser Asn  Asn Val Asp Trp Lys  Ser Asn Asp
        995                 1000                1005

Met Glu  Glu Asp Gln Gly Glu  Leu Ser Arg Ala Pro  Glu Ser Ile
    1010                 1015                 1020

Lys Val  Lys Ile Pro Glu Met  Thr Ser Asp Trp Gln  Ser Pro Val
    1025                 1030                 1035

Arg Ser  Ser Pro Asp Asp Ile  Tyr Ala Val Cys Thr  Ser Ile Ser
    1040                 1045                 1050

Thr Thr  Thr Pro Gln Arg Ser  His Glu Ala Val Glu  Ala Ser Leu
    1055                 1060                 1065

Pro Ala  Ile Thr Arg Thr Lys  Ser Asn Leu Gly Lys  Asn Ile Arg
    1070                 1075                 1080

Glu His  Gly Cys Lys Val Gln  Gly Thr Gly Lys Pro  Glu Val Ser
    1085                 1090                 1095

Arg Asp  Arg Pro Ser Ser Val  Arg Thr Ser Arg Glu  Asp Ile Tyr
    1100                 1105                 1110

Thr Val  Arg Pro Ser Pro Glu  Asn Thr Gly Gln Lys  Pro Phe Glu
    1115                 1120                 1125

Ala Phe  Glu Pro Ser Tyr Gly  Ala Ser Leu Ser His  Phe Asp Asp
    1130                 1135                 1140

Gly Leu  Ala Ala Lys Tyr Gly  Gly Phe Gly Gly Gly  Tyr Arg Met
    1145                 1150                 1155
```

Pro Asp Pro Pro Phe Leu Pro Asp Gln Phe Pro Leu Arg Asn Gly
1160 1165 1170

Pro Asn Glu Met Phe Asp Phe Arg Gly Tyr Ser Asp Leu Asp Arg
1175 1180 1185

Gly Ile Gly Gln Arg Glu Tyr Pro Gln Gln Tyr Gly Gly His Leu
1190 1195 1200

Asp Pro Met Leu Ala Pro Pro Pro Pro Pro Asn Leu Met Asp Asn
1205 1210 1215

Ala Phe Pro Leu Gln Gln Arg Tyr Ala Pro His Phe Asp Gln Met
1220 1225 1230

Asn Tyr Gln Arg Met Ser Ser Phe Pro Pro Gln Pro Pro Leu Gln
1235 1240 1245

Pro Ser Gly His Asn Leu Leu Asn Pro His Asp Phe Pro Leu Pro
1250 1255 1260

Pro Pro Pro Pro Ser Asp Phe Glu Met Ser Pro Arg Gly Phe Ala
1265 1270 1275

Pro Gly Pro Asn Pro Asn Tyr Pro Tyr Met Ser Arg Ser Gly Gly
1280 1285 1290

Trp Ile Asn Asp
1295

<210> SEQ ID NO 11
<211> LENGTH: 1323
<212> TYPE: PRT
<213> ORGANISM: Oryza sativa

<400> SEQUENCE: 11

Met Met Ser Ser Asp Asp Asp Leu Glu Pro Gln Leu Lys Ala Val Glu
1 5 10 15

Asn Tyr Tyr Phe Val Asp Asp Asn Asp Val Pro Val Ser Phe Asp Val
20 25 30

Leu Pro Phe Gln Phe Asp Ala Ala Glu Gly Val Ala Ser Phe Lys Lys
35 40 45

Asp Val Tyr Leu Arg Gly Phe Thr Asp Gly Gly Leu Gln Lys Val Tyr
50 55 60

Lys Gln Val Val Ala Trp Lys Leu Val Leu Asp Gly Asp Ser Pro Glu
65 70 75 80

Ile Ala Val Leu Ser Thr Glu Gly Ser Trp Ile Ala Leu Leu Lys Pro
85 90 95

Arg Pro Ser Tyr Glu Glu Thr Ile Arg Ser Val Leu Ile Thr Val Glu
100 105 110

Met Leu His Phe Val Arg Arg Arg Pro Thr Asp Ser Glu Lys Asp Met
115 120 125

Trp Asp His Leu Tyr Gly Val Phe Glu Arg Phe Val Val Arg Pro Leu
130 135 140

Glu Asp Asp Phe Ala Asn His Gln Asn Leu Ile Lys Leu Phe Ala Gln
145 150 155 160

Arg Asp Pro Asp Leu Ala Asn Ser Gln Val Leu Gln Val Phe Ile Lys
165 170 175

Asp Lys Ile Met Glu Lys Thr Asn Glu Val Gly Ser Asn Asn Leu Asp
180 185 190

Asn Lys Arg Glu Pro Asp Ile Lys Gln Glu Pro Asp Ile Lys Gln Glu
195 200 205

Pro Val Ala Ala Gly Asp Glu Met Glu Glu Ile Val Glu Glu Gly Ile
210 215 220

-continued

```
Pro Asp Ala Pro Ser Asn Asp Asp Asp Asp Asp Glu Glu Asp Glu Glu
225                 230                 235                 240

Asp Gly Asp Leu Phe Asp Ser Val Cys Ala Ile Cys Asp Asn Gly Gly
                245                 250                 255

Glu Leu Leu Cys Cys Glu Gly Pro Cys Met Arg Ser Phe His Ala Lys
            260                 265                 270

Ile Arg Asp Gly Glu Asp Ser Tyr Cys Ala Thr Leu Gly Tyr Thr Lys
        275                 280                 285

Ala Glu Val Lys Ala Leu Lys Asn Phe Val Cys Lys Asn Cys Asp His
    290                 295                 300

Lys Gln His Gln Cys Phe Val Cys Gly Glu Leu Glu Pro Ser Asp Gly
305                 310                 315                 320

Pro Asn Ala Lys Val Phe Leu Cys Asn Asn Ala Thr Cys Gly His Phe
                325                 330                 335

Tyr His Pro Arg Cys Val Ala Gln Leu Leu His Pro Asn Ser Arg Asn
            340                 345                 350

Glu Ala Ser Glu Met Glu Lys Lys Ile Met Ala Gly Phe Ser Phe Thr
        355                 360                 365

Cys Pro Val His Trp Cys Phe His Cys Lys Gly Leu Glu Asp Arg Thr
    370                 375                 380

Gln Glu Pro Leu Gln Phe Ala Val Cys Arg Arg Cys Pro Arg Ser Tyr
385                 390                 395                 400

His Arg Lys Cys Leu Pro Arg Glu Ile Ser Phe Glu Asp Ile Asn Thr
                405                 410                 415

Gln Gly Ile Ile Thr Arg Ala Trp Glu Leu Ser Lys Arg Ile Leu Ile
            420                 425                 430

Tyr Cys Leu Asp His Glu Ile Asp Leu Asp Ile Gly Thr Pro Pro Arg
        435                 440                 445

Asp His Ile Lys Phe Pro His Val Glu Lys Ser Ala Tyr Ser Ala Lys
    450                 455                 460

Lys Lys Val Lys Glu Leu Ala Glu Lys Lys Arg Arg Ile Cys Asp Asp
465                 470                 475                 480

Ser Tyr Val Ser Glu Pro Leu Gln Lys Arg Ala Lys Leu Asn Glu Lys
                485                 490                 495

Phe Asn Ala Lys Gly Asp Lys Ser Lys Lys Ala Gly Val Lys Ser Glu
            500                 505                 510

Phe Glu Glu Val Leu Glu Ser Glu Lys Lys Lys Thr Arg Ser Leu Lys
        515                 520                 525

Lys Arg Thr Gln Pro Glu Glu Pro Leu Val Glu Cys Ala Ala Ala Ala
    530                 535                 540

Ala Ala Asn Asn Ala Asn Arg Pro Val Lys Glu Arg Glu Lys Glu Leu
545                 550                 555                 560

Gly Thr Ser Ser Leu Asp Met Gly Lys Ile Pro Leu Ser Ser Phe Pro
                565                 570                 575

Ile Val Asp Ser Glu Thr Glu Lys Arg Ile Ser Ala Leu Val Glu Lys
            580                 585                 590

Glu Val Ser Ser Leu Thr Val Ala Asp Ile Ser Arg Arg Cys Val Ile
        595                 600                 605

Pro Ser Thr Tyr Ala Cys Ser Gly Arg Gln Ile Asp Lys Ile Val Val
    610                 615                 620

Arg Gly Lys Leu Glu Arg Ser Ile Gln Ala Val Lys Ala Ala Leu Gln
625                 630                 635                 640
```

-continued

```
Lys Leu Glu Asn Gly Gly Ala Val Asp Asp Ala Lys Ala Val Cys Glu
                645                 650                 655

Ser Glu Val Leu Arg Gln Leu Thr Arg Trp His Asn Lys Leu Arg Val
            660                 665                 670

Tyr Leu Ala Pro Phe Ile His Gly Met Arg Tyr Thr Ser Phe Gly Arg
        675                 680                 685

His Phe Thr Lys Lys Glu Lys Leu Ile Glu Ile Ala Glu Lys Leu His
    690                 695                 700

Trp Tyr Val Gln Pro Gly Asp Met Lys Ser Asn Asn Val Asp Pro Glu
705                 710                 715                 720

Thr Arg Pro Arg Arg Val Asn Met Leu Arg Gly Phe Gly Ala Leu Ser
                725                 730                 735

Gln Phe Met Lys Glu Lys Leu Asp Lys Val Gly Lys Arg Cys Asn Phe
            740                 745                 750

Lys Asn Tyr Asp Val Ile Gln Pro Lys Asn Ser Phe Ser Phe Glu Lys
        755                 760                 765

Arg Asp Trp Met Thr Val Arg Gln Lys Glu Leu Pro His Gly Ser Lys
    770                 775                 780

Leu Ile Met Gly Leu Asn Pro Pro Phe Gly Pro Lys Ala Met Leu Ala
785                 790                 795                 800

Asn Lys Phe Ile Asp Lys Ala Leu Thr Phe Lys Pro Lys Leu Ile Ile
                805                 810                 815

Leu Ile Val Pro Lys Glu Ala Glu Arg Leu Asp Arg Lys Gln Gln Pro
            820                 825                 830

Tyr Asp Leu Val Trp Glu Asp Asp Gln Arg Leu Ser Gly Lys Ser Phe
        835                 840                 845

Tyr Leu Pro Gly Ser Leu Asp Val Ser Asp Lys Gln Ile Asp Gln Trp
    850                 855                 860

Asn Lys Ser Pro Pro Pro Leu Tyr Leu Trp Ser Arg Pro Asp Trp Thr
865                 870                 875                 880

Gln Lys His Lys Arg Ile Ala Glu Gln His Gly His Thr Lys Ala Asn
                885                 890                 895

Val Phe Ser His Asn Glu Glu Asp Leu Val Tyr Leu Phe Glu Asp Arg
            900                 905                 910

Ala Thr Gln Asn His Asp Val Asn Asn Lys Asn Tyr Thr Ser Gly Asn
        915                 920                 925

Gly Asn Phe Thr Ala Glu Lys Pro Val Gln Ala Asp Ala Phe Pro Pro
    930                 935                 940

Glu Lys Leu Val Glu Val Ala Tyr Glu Glu Met Lys Val Ala Ser Asn
945                 950                 955                 960

Arg Ser Ser Met Tyr Gln Ser Asp Gln Ile Ser Val His Asp Glu Arg
                965                 970                 975

Asp Ala His Ser Asp Leu Pro Met Ser Arg His Asn Ser Met Lys Ala
            980                 985                 990

Lys Glu Val Ser Asn Ser Ser Arg  Asp Arg Arg Lys Ser  Asp Lys Thr
        995                 1000                1005

Gly His  Glu Ala Asp Ser Asp  Met Ser Ile Leu Pro  Ser Asp Ser
    1010                1015                1020

Arg Asn  Phe Leu His Lys Ser  Gly Asn Leu Glu Pro  Pro Ile Ser
    1025                1030                1035

Ser Arg  Ser Gly Tyr Thr Leu  Glu Arg Leu Arg Tyr  His Asp Asn
    1040                1045                1050

His Phe  Asp His Leu Val Gly  Glu His Ser Ser Ser  Ser Leu Gln
```

1055 1060 1065

Met Pro Ile Phe Glu Asp Ser Tyr Phe Arg Ser Val Asn Glu Tyr
1070 1075 1080

Gly Val Ala Ser Val Glu Asn Asn Ile Ala Leu Ser Thr Asp Asn
1085 1090 1095

Val Gly Ala Gly Ser Arg Met Tyr Ser Pro Asp Pro Glu Leu Asn
1100 1105 1110

Gly Tyr Ala Val Asp Pro Thr Val Asn Ala Tyr Gly Ser Val Ser
1115 1120 1125

Gly Gly Thr Gly Gly Ser Phe Tyr Arg Arg Gln Asn Leu Glu Asp
1130 1135 1140

Tyr Thr Met Asp Ser Ser Glu Ser Ala Gln Met Asn Pro Val Pro
1145 1150 1155

Gly Arg Asp Val Gln Glu Tyr Ala Arg Thr Tyr Tyr Gly His Asn
1160 1165 1170

Arg Asp Glu Val Pro Gln Thr Ala Ile Asn Thr Pro Ser Met Asp
1175 1180 1185

Ile Arg Thr His Ile Arg Met Tyr Gly Arg His Ile Arg Asp Asp
1190 1195 1200

His Thr Gln Thr Thr Met Asn Pro Pro Ala Asn Asp Ile Arg Ala
1205 1210 1215

Gln Ile Arg Met Tyr Gly Gln His Ala Thr Ser Asp His Gln His
1220 1225 1230

Ala Ser Arg Tyr Ser Ser Gly Ser Pro Asp Ala Arg Phe Glu Gln
1235 1240 1245

Gln Pro Ser Phe Thr Ser Tyr Gly Met Pro Ser Leu Gly Ser Thr
1250 1255 1260

Gly Arg Ser Met Met Asp Arg Tyr Ser Pro Ser Ile Asp Glu Thr
1265 1270 1275

Ser Tyr Arg Thr Gly Gln Arg Gly Pro Tyr Asn Ala Ser Asp Phe
1280 1285 1290

Arg Arg Asp Arg His Pro Asp Asp Met Asn Phe Ala Leu His Asn
1295 1300 1305

Gln Tyr Pro Tyr Pro His Pro Gly Ser Ser Gly Gly Trp His Asp
1310 1315 1320

<210> SEQ ID NO 12
<211> LENGTH: 631
<212> TYPE: PRT
<213> ORGANISM: Sorghum bicolor

<400> SEQUENCE: 12

Met Glu Asn Lys Thr Gln Arg Ala Leu Gln Leu Ala Val Cys Arg Arg
1 5 10 15

Cys Pro Arg Ala Tyr His Trp Glu Cys Leu Pro Arg Glu Leu Ser Leu
20 25 30

Gly Ala Lys Asp Lys Asp Gly Asn Pro Arg Ala Trp Lys Leu Ser Lys
35 40 45

Thr Ile Phe Phe Tyr Cys Leu Asp His Glu Ile Asp Lys Asp Thr Arg
50 55 60

Thr Ala Ser Arg Asn His Ile Lys Phe Pro Ala Thr Pro Glu Cys Thr
65 70 75 80

Lys Thr Lys Glu Leu Gly Asn Arg Lys Gly Arg Met Thr Gly Lys Arg
85 90 95

-continued

```
Arg Lys Asn Thr Asp Gln Ser Thr Glu Pro Thr Glu Leu Ser Asn Arg
            100                 105                 110

Leu Tyr Gly Ala Glu Ser Glu Gln Ala Asp Asn Val Gly Ala Lys Ser
        115                 120                 125

Thr Ser Pro Gln Ile Val Val Glu Pro His Cys Ala Ala Lys Val Leu
    130                 135                 140

Lys Gly Asp Pro Gln Ile Glu Gln Ser Ile Ile Gly Val Ala Gly Ser
145                 150                 155                 160

Gln Asn Gly Ala Glu Thr Met Asn Gly His Glu Lys Gln Phe Gly Ile
                165                 170                 175

Ser Cys Val Ala Arg Thr Glu Thr Glu Lys Arg Val Thr Tyr Leu Ala
            180                 185                 190

Gln Lys Gly Thr Cys Leu Gly Thr Pro Tyr Asp Gly Pro Ser Thr Lys
        195                 200                 205

Asp Met Ser Asp Cys Ser Val Gln Asp Thr Pro Val Asp Lys Asp Phe
    210                 215                 220

Glu Leu Asp Asn Val Ala Tyr Arg Ile Met Glu Asp Lys Tyr Ala Asn
225                 230                 235                 240

Gly Arg Glu Glu Thr Gln Glu Asp Tyr Thr Arg Lys Glu Thr Ala His
                245                 250                 255

Arg Lys Asp Ser Ser Glu Asn Gln Gly Gln Asn Asp Val Leu Glu Leu
            260                 265                 270

Asp Asn Leu Trp Val Glu Ile Gln Ala Asp Gly Ser Pro Leu Glu Pro
        275                 280                 285

Gly Asn Lys Arg Tyr Lys Glu Glu Asn Ala Tyr Gly Leu Gly Ser Ala
    290                 295                 300

Ser Gly His Glu Lys Glu Thr Ser Ser Ser Arg Arg Glu Asn Val Gln
305                 310                 315                 320

Ser Asp Arg Gly Met Val Pro Met Asn Asp Ser Lys Thr Ile Asp Tyr
                325                 330                 335

Arg Lys Gly Gly Thr Thr Leu Asp Asn Asn Val Tyr Asp His Ser Ser
            340                 345                 350

Glu Gly Ser Tyr Pro Cys Gln Gly Glu Cys Ser His Ser Lys Cys Asn
        355                 360                 365

Asp Gly Leu Val Ala Ile Asp Gln Asp Thr Ser Ser Asp Arg Leu Lys
    370                 375                 380

Lys Arg Ser Gln Pro Val Glu Lys Ala Ser Asp Gly Asn Lys Thr Asp
385                 390                 395                 400

Leu Asp Lys Asn Lys Lys His Asn Leu Lys Glu Asp Gly Arg Asp Ala
                405                 410                 415

His Tyr Glu Asp Arg Arg Thr Glu Arg Asn Thr Ala Ala Asp Thr Ser
            420                 425                 430

Arg Tyr Lys Cys Arg Asp Lys Ile Gln Leu Asp Arg Arg Glu Pro Glu
        435                 440                 445

Leu Val Gly Arg Asn Thr Arg Ala Arg Ser Ser Glu His Ser Pro Glu
    450                 455                 460

Arg Gln Arg Met Glu Arg Asp Gly Ser Tyr Pro Gly Thr Tyr Asn Arg
465                 470                 475                 480

Arg Arg Tyr Glu Ser Leu His Asn Phe Asn Pro Pro Arg Ser Gly Cys
                485                 490                 495

Asp Asp Arg Arg Gln Leu Ser Pro Cys Gln Ser Ser Phe Pro Leu Pro
            500                 505                 510

Glu Phe Cys Gly Asp His Ser His Leu Tyr Pro Arg Asp Ser Thr Ile
```

```
        515                 520                 525

Gly Arg His Asn Pro His Arg Tyr Leu Gly Ile Pro Gln Tyr Gly Pro
    530                 535                 540

Tyr Met Ala Ala Ser Ala Ala Gly His Ser Ala Val Cys Tyr Arg Leu
545                 550                 555                 560

Ala Gly Gly Tyr Gly Glu Gly Ser Arg Ala Ser Arg Pro Val Thr Asp
                565                 570                 575

Trp Tyr Ala Pro His Leu Asp Arg Thr Asn Cys Gln Pro Arg Ser Gln
            580                 585                 590

Ile Asp Leu Gln Leu Gln Ala Ser Arg Pro Val Thr Asp Lys Tyr Ala
        595                 600                 605

Pro Gln Leu Glu Leu Thr Asn Tyr Pro Pro Arg Ser Gln Ser Asp Leu
    610                 615                 620

Gln Tyr Cys Thr Thr Thr Ile
625                 630


<210> SEQ ID NO 13
<211> LENGTH: 1420
<212> TYPE: PRT
<213> ORGANISM: Brachypodium distachyon

<400> SEQUENCE: 13

Met Met Met Ser Asp Asp Asp Asp Asp Ser Glu Pro Gln Val Val Val
1               5                   10                  15

Val Lys Asp Tyr Tyr Phe Val Asp Ala Asp Lys Asn Ala Leu Cys Phe
            20                  25                  30

Ser Val Leu Pro Ile Trp Phe Lys Glu Asp Ala Val Ala Val Pro Glu
        35                  40                  45

Cys Lys Thr Gly Val Phe Leu Arg Gly Thr Val Asp Pro Gly Ile Pro
    50                  55                  60

Val Tyr Lys Gln Val Val Ala Trp Lys Leu Gly Leu Asp Ala Arg Gln
65                  70                  75                  80

Pro Asp Leu Ala Val Leu Ser Lys Glu Gly Gly Trp Ile Asn Leu Ser
                85                  90                  95

Lys Pro Lys Asn Ser Tyr Glu Glu Ser Phe Arg Thr Ile Phe Ile Thr
            100                 105                 110

Val Gln Met Leu His Phe Leu Arg Arg Lys Pro Glu Glu Pro Glu Lys
        115                 120                 125

Asp Leu Trp Ile His Leu Arg Lys Val Phe Asp Lys Phe Asp Val Arg
    130                 135                 140

Pro Ser Lys Asp Asp Phe Arg Asn His His Thr Leu Met Lys Gln Phe
145                 150                 155                 160

Ala Glu Lys Asp Leu Arg Leu Ala Asn Ser Glu Ile Leu Lys Val Phe
                165                 170                 175

Ile Gly Glu Arg Phe Arg Lys Gln Ile Ser Glu Val Asp Ser Gly Asn
            180                 185                 190

Phe Glu Val Lys Glu Ser Phe Ile Ala Ala Asp Glu Asp Val Glu Asp
        195                 200                 205

Ile Val Ala Asp Asp Asn Val Glu Ser Asp Glu Asp Gly Asp Asp Asp
    210                 215                 220

Leu Phe Asp Ser Thr Cys Ala Ile Cys Asp Asn Gly Gly Asp Leu Leu
225                 230                 235                 240

Gly Cys Asp Gly Pro Cys Met Arg Ser Phe His Ala Lys Ile Gly Thr
                245                 250                 255
```

```
Gly Glu Asp Ser Tyr Cys Gln Thr Leu Gly Phe Thr Glu Ala Glu Val
            260                 265                 270

Glu Ala Met Lys Thr Phe Leu Cys Lys Asn Cys Glu Tyr Lys Gln His
        275                 280                 285

Gln Cys Phe Ile Cys Gly Val Leu Glu Pro Ser Asp Gly Pro Thr Ala
    290                 295                 300

Lys Val Phe Leu Cys Asn Asn Ala Thr Cys Gly Tyr Phe Tyr His Pro
305                 310                 315                 320

Lys Cys Val Ala Gln Gln Leu His Pro Asn Asn Lys Ile Glu Ala Leu
                325                 330                 335

Glu Lys Glu Lys Lys Ile Ala Gly Gly Ser Ser Phe Thr Cys Ser Ile
            340                 345                 350

His Trp Cys Phe Cys Cys Lys Gly Leu Glu Asp Arg Thr Glu Glu His
        355                 360                 365

Leu Gln Phe Ala Val Cys Arg Arg Cys Pro Lys Ser Tyr His Arg Lys
    370                 375                 380

Cys Leu Pro Ser Glu Ile Pro Phe Glu Asp Ser Asp Glu Asp Ile Val
385                 390                 395                 400

Thr Arg Ala Trp Asp Leu Ser Gln Arg Ile Leu Ile Tyr Cys Met Glu
                405                 410                 415

His Glu Ile Asp Leu Asp Ile Glu Thr Pro Val Arg Asn His Ile Lys
            420                 425                 430

Phe Pro Gly Leu Pro Ile Lys Pro Thr Glu Tyr Leu Lys Lys Lys Thr
        435                 440                 445

Lys Val Leu Ile Lys Lys Lys Lys Arg Thr Phe Asp Glu Ser Phe Leu
    450                 455                 460

Asp Glu Pro Ser Ile Lys Pro Ala Lys Phe Pro Gly Lys Val Arg Val
465                 470                 475                 480

Gln Glu Asn Glu His Ala Arg Lys Ile Ala Val Arg Ser Ser Ser Glu
                485                 490                 495

Gln Leu Val Glu Lys Pro Glu Lys Lys Lys Val Lys Leu Leu Lys Gln
            500                 505                 510

Arg Thr Gln Pro Glu Ser Asn Met Val Arg Asp Ala Ala Ala Ser Ser
        515                 520                 525

Pro Lys His Ala Asn Lys Gln Glu Lys Tyr Trp Ser Ser Ser Thr Ser
    530                 535                 540

Ser Thr Thr Met Asn Met Pro Gln Ser Ser Phe Pro Ile Val Asp Ser
545                 550                 555                 560

Glu Thr Glu Arg Arg His Asp Lys Asn Leu Phe Ile Cys Leu Asp Val
                565                 570                 575

Tyr Gln Tyr Phe Cys Met Pro Phe Gly His Phe Ser Ala Leu Phe Leu
            580                 585                 590

Pro Ala Leu Ala Ile Ser Tyr Thr Ser Gln Thr Leu Ala Gly Gln Phe
        595                 600                 605

Phe Asp Lys Val Trp Leu Phe Leu Gly Ser Ser Leu Leu Pro Cys Met
    610                 615                 620

Cys Lys Val Val Ile Ala Leu Val Glu Lys Glu Val Ser Ser Leu Thr
625                 630                 635                 640

Leu Asn Asp Ile Ser Arg Lys Cys Leu Met Pro Ser Thr His Val Tyr
                645                 650                 655

Ser Gly Arg Gln Thr Asp Lys Ile Ile Ala Thr Gly Lys Leu Glu Arg
            660                 665                 670

Ser Val Gln Ala Val Arg Gln Ala Leu His Leu Leu Ala Val Gly Asp
```

-continued

```
        675                 680                 685

Val Asn Thr Ala Lys Ala Thr Cys Glu Pro Gln Val Leu Lys Gln Leu
    690                 695                 700

Ala Arg Trp His Met Lys Leu Lys Val Tyr Ile Ser Pro Phe Ile Tyr
705                 710                 715                 720

Gly Ser Arg Tyr Ser Ser Phe Gly Arg His Phe Thr Lys Val Glu Lys
                725                 730                 735

Leu Val Glu Ile Val Asp Lys Leu His Trp Tyr Val Glu Pro Gly Asp
            740                 745                 750

Met Ile Val Asp Phe Cys Cys Gly Ala Asn Asp Phe Ser Arg Leu Met
        755                 760                 765

Lys Glu Lys Leu Asp Leu Val Gln Lys Lys Cys His Phe Lys Asn Tyr
    770                 775                 780

Asp Leu Ile Gln Pro Gln Asn Thr Phe Cys Phe Glu Arg Arg Asp Trp
785                 790                 795                 800

Met Thr Val Gln Arg Asn Glu Leu Pro Arg Gly Ser Arg Leu Val Met
                805                 810                 815

Gly Leu Asn Pro Pro Phe Gly Val Lys Ala Ala Leu Ala Asn Lys Phe
            820                 825                 830

Ile Asp Lys Ala Leu Ser Phe Asn Pro Lys Leu Ile Ile Leu Ile Val
        835                 840                 845

Pro Lys Glu Thr Lys Arg Leu Asp Gln Lys Lys Thr Pro Tyr Asp Leu
    850                 855                 860

Val Trp Glu Asp Gly Asp Cys Leu Ala Gly Lys Ser Phe Tyr Leu Pro
865                 870                 875                 880

Gly Ser Val Asp Val Asn Glu Lys Ile Val Gln Gly Trp Asn Ala Ser
                885                 890                 895

Ala Pro Pro Leu Tyr Leu Trp Ser His Pro Asp Trp Thr Lys Lys His
            900                 905                 910

Lys Lys Val Ala Glu Glu His Asn His Thr Ser Leu Ala Lys Ile Ala
        915                 920                 925

Cys Arg Ile Glu Glu Gly Asn Leu Ser Asp Asp Val Pro Met Lys Lys
    930                 935                 940

Glu Ala Glu Ser Ser Asp Val His Asn Ser Arg Pro Arg Lys Glu Asp
945                 950                 955                 960

Glu Asn Thr Gly Arg Thr Ser Cys His Leu Glu Glu Ala Ser Leu Ser
                965                 970                 975

Asn Val Val Pro Val Gln Arg Gln Ala Glu Pro Lys Ser Lys Gln Asn
            980                 985                 990

Ala Arg Ser Gly Lys Ala Lys Trp  Thr Lys Glu Arg Thr  Ser Cys Asp
        995                 1000                1005

Val Arg  Asp Val Ile Pro Ser  Asp Glu Thr Leu Ala  Lys Lys Gln
    1010                 1015                 1020

Asp Arg  Ser Gly Glu Asp Gln  Ala Lys Glu Pro Asn  His Leu Val
    1025                 1030                 1035

Gln Lys  Gln Ser Arg Ser Gly  Glu Asp Lys Ala Lys  Glu Pro Asn
    1040                 1045                 1050

Arg Leu  Val Lys Lys Gln Ala  Arg Phe Gly Glu Glu  Lys Asp Lys
    1055                 1060                 1065

Glu Arg  Asn Arg Leu Val Lys  Lys Gln Ala Arg Ser  Gly Glu Asp
    1070                 1075                 1080

Lys Tyr  Ser Asn Leu Ala Gly  Gly Leu Ser Ala Lys  Asn Gln Ala
    1085                 1090                 1095
```

```
Glu Ala  Ala Leu Gln Gln Met  Cys Arg Ser Gly Lys  His Asn Ser
    1100                 1105                 1110

Arg Asp  Gly Ser Lys Ser Ser  Asp Asp Arg Ser Arg  Lys Arg Thr
    1115                 1120                 1125

Pro Asp  Glu Val Asp Ser Leu  Pro Pro Glu Lys Gln  Val Glu Val
    1130                 1135                 1140

Ala Phe  Glu Glu Arg Arg Ala  Pro Ile Lys Met Ser  Ile Gln Arg
    1145                 1150                 1155

Glu Gln  Arg Asp Ala Phe Cys  Glu Asn Leu Arg Asn  Asp His Ile
    1160                 1165                 1170

Lys Glu  Pro Ser Arg Gly Ser  Ser Asp Met Asn Met  Ser Ser Pro
    1175                 1180                 1185

Asp Thr  Ser Asn Ala Pro Asn  Arg Ser Thr Ser Tyr  Ser Pro Tyr
    1190                 1195                 1200

Met Pro  Thr Glu Gln Pro Ser  Glu Phe Arg Pro Thr  Ala Tyr Leu
    1205                 1210                 1215

Asp Gly  Asn Met Ser Tyr Pro  Val Lys Glu Pro His  Val Ser Ala
    1220                 1225                 1230

Phe Ser  Ser Ala Thr Tyr Gln  Gly Ser Tyr Leu Ala  Arg Ser Asp
    1235                 1240                 1245

Arg His  Asn Asp Ala Leu Gly  Val Lys Asn Asp Pro  Met Leu Tyr
    1250                 1255                 1260

Thr His  Ala Val Asp Gly Ser  Lys Tyr Ser Pro Ser  Phe Glu Glu
    1265                 1270                 1275

Leu Thr  Met Arg Tyr Ala Ala  Asn Pro Ala Gly Asp  Gly Tyr Ser
    1280                 1285                 1290

Met Gln  Ala Gln Gly Asp Asp  Tyr Leu Pro Met Ser  Arg His Ser
    1295                 1300                 1305

Leu Gly  Ser Ser Gly Ala Arg  Tyr Asp Gln Pro Ser  Leu Arg Ser
    1310                 1315                 1320

Tyr Tyr  Gly Leu Ser Gly Thr  Thr Ala Pro Gln Ser  Ser Ile Thr
    1325                 1330                 1335

Asp Lys  Tyr Gly Pro Gly Leu  Phe Gly Pro Ser Gly  Ser Gly Ala
    1340                 1345                 1350

Ser Val  Thr Asp Lys Tyr Ala  Pro Gly Phe Leu Gly  Pro Ser Ala
    1355                 1360                 1365

Pro Gly  Ser Ser Val Ile Asp  Asn Tyr Ala Ala Pro  Leu Asn Gly
    1370                 1375                 1380

Thr Asn  Tyr Ala Thr Gln Ser  Val Ile Asp Met Pro  Gly Tyr Gly
    1385                 1390                 1395

Arg Glu  Met Pro Pro Gln Tyr  Pro Tyr Arg Gly Pro  Gly Ser Ser
    1400                 1405                 1410

Gly Gly  Gly Leu Pro Tyr Thr
    1415                 1420
```

<210> SEQ ID NO 14
<211> LENGTH: 1341
<212> TYPE: DNA
<213> ORGANISM: Zea mays

<400> SEQUENCE: 14

```
atggccgcca ccaggagagc cttcttccac agcgccgtcg acggcattgc gcgcgccggg     60

ccgggggagg ccgagcggct gccggcgccg ccgcaggtcg ggcgaccggt ggaaggcgcc    120
```

-continued

```
agcagcatgg tcttgggctt ccccgtgccg cggcccacga tgccggaccg ccggccggcc    180
gccgtcaccc agcagttctt tccgcccact actacggccg cgcagcaggc gacgatggag    240
gagcaatgcc acgtgcccgc cggtagcgcg gcggagcagt gggtccggtc gtcggcgtcc    300
aggaagagcc ggcgcggccc gcggtcacgg agctcgcagt accgcggcgt caccttctac    360
cgccgcaccg gccgctggga gtcccacatc tgggactgtg ggaaacaggt gtacttgggt    420
ggattcgaca cggcgcaggc cgctgcgagg gcctacgacc aagccgcgat caagttccgc    480
ggcctgaacg cggacatcaa cttcaccctg gacgactaca aggacgagat gaagaagatg    540
aaggacttga gcaaggagga gttcgtgttg gtgctccggc ggcagggcgc cggcttcgtc    600
aggggcagct ccaggttccg gggagtcacc cagcacaagt gcggcaagtg ggaggccagg    660
atcggccagc tcatgggcaa gaagtatgtg tacctgggcc tgtatgacac agagacggag    720
gctgcccagg catatgacaa ggctgccatc aagtgctacg gcaaggaggc ggtgaccaac    780
ttcgatgccc agagctacga caaggagctc cagtcgcagc cctgggacgg cgagctggat    840
ctcgagctca gtctgggctg cgccagcagc gatccgtcca cggtcgccgt cgaggcgttc    900
agccccgcga cgagcagcag tagccgcaag cagaggacga tgacgctgac gctcggtctg    960
ccggaggagg aggagacggg cgccggctac cctcaccctg ctgccggcat gttcgggcgc   1020
ccggctgatg gccacgtcca cgtagcaccg ccgccacacc ggcaatggca gcagcagcag   1080
cagggacagc acgcagctcc agatgcggcg cctgagcgac gagcggcaga gccagcagat   1140
cggcagcggt ggggccgggg cgcgcgctgg cccatcgcca gcgccagcgg cattaactgg   1200
gcctgggcgc cgccgtacgc caccgcccgc gccggcaccg acgacgacga cgccagcagc   1260
gccgccgctg cagcatcatc aggattccca ctgtggcagc tgggtgcggc gtcgtccagg   1320
tccagctggc ccagctgctg a                                             1341
```

```
<210> SEQ ID NO 15
<211> LENGTH: 446
<212> TYPE: PRT
<213> ORGANISM: Zea mays

<400> SEQUENCE: 15

Met Ala Ala Thr Arg Arg Ala Phe Phe His Ser Ala Val Asp Gly Ile
1               5                   10                  15

Ala Arg Ala Gly Pro Gly Glu Ala Glu Arg Leu Pro Ala Pro Pro Gln
            20                  25                  30

Val Gly Arg Pro Val Glu Gly Ala Ser Ser Met Val Leu Gly Phe Pro
        35                  40                  45

Val Pro Arg Pro Thr Met Pro Asp Arg Arg Pro Ala Ala Val Thr Gln
    50                  55                  60

Gln Phe Phe Pro Pro Thr Thr Thr Ala Ala Gln Gln Ala Thr Met Glu
65                  70                  75                  80

Glu Gln Cys His Val Pro Ala Gly Ser Ala Ala Glu Gln Trp Val Arg
                85                  90                  95

Ser Ser Ala Ser Arg Lys Ser Arg Arg Gly Pro Arg Ser Arg Ser Ser
            100                 105                 110

Gln Tyr Arg Gly Val Thr Phe Tyr Arg Arg Thr Gly Arg Trp Glu Ser
        115                 120                 125

His Ile Trp Asp Cys Gly Lys Gln Val Tyr Leu Gly Gly Phe Asp Thr
    130                 135                 140

Ala Gln Ala Ala Ala Arg Ala Tyr Asp Gln Ala Ala Ile Lys Phe Arg
145                 150                 155                 160
```

-continued

```
Gly Leu Asn Ala Asp Ile Asn Phe Thr Leu Asp Asp Tyr Lys Asp Glu
                165                 170                 175

Met Lys Lys Met Lys Asp Leu Ser Lys Glu Glu Phe Val Leu Val Leu
            180                 185                 190

Arg Arg Gln Gly Ala Gly Phe Val Arg Gly Ser Ser Arg Phe Arg Gly
        195                 200                 205

Val Thr Gln His Lys Cys Gly Lys Trp Glu Ala Arg Ile Gly Gln Leu
    210                 215                 220

Met Gly Lys Lys Tyr Val Tyr Leu Gly Leu Tyr Asp Thr Glu Thr Glu
225                 230                 235                 240

Ala Ala Gln Ala Tyr Asp Lys Ala Ala Ile Lys Cys Tyr Gly Lys Glu
                245                 250                 255

Ala Val Thr Asn Phe Asp Ala Gln Ser Tyr Asp Lys Glu Leu Gln Ser
            260                 265                 270

Gln Pro Trp Asp Gly Glu Leu Asp Leu Glu Leu Ser Leu Gly Cys Ala
        275                 280                 285

Ser Ser Asp Pro Ser Thr Val Ala Val Glu Ala Phe Ser Pro Ala Thr
    290                 295                 300

Ser Ser Ser Ser Arg Lys Gln Arg Thr Met Thr Leu Thr Leu Gly Leu
305                 310                 315                 320

Pro Glu Glu Glu Glu Thr Gly Ala Gly Tyr Pro His Pro Ala Ala Gly
                325                 330                 335

Met Phe Gly Arg Pro Ala Asp Gly His Val His Val Ala Pro Pro Pro
            340                 345                 350

His Arg Gln Trp Gln Gln Gln Gln Gln Gly Gln His Ala Ala Pro Asp
        355                 360                 365

Ala Ala Pro Glu Arg Arg Ala Ala Glu Pro Ala Asp Arg Gln Arg Trp
    370                 375                 380

Gly Arg Gly Ala Arg Trp Pro Ile Ala Ser Ala Ser Gly Ile Asn Trp
385                 390                 395                 400

Ala Trp Ala Pro Pro Tyr Ala Thr Ala Arg Ala Gly Thr Asp Asp Asp
                405                 410                 415

Asp Ala Ser Ser Ala Ala Ala Ala Ala Ser Ser Gly Phe Pro Leu Trp
            420                 425                 430

Gln Leu Gly Ala Ala Ser Ser Arg Ser Ser Trp Pro Ser Cys
        435                 440                 445
```

<210> SEQ ID NO 16
<211> LENGTH: 588
<212> TYPE: DNA
<213> ORGANISM: Zea mays

<400> SEQUENCE: 16

```
atggccgcgc acccggagct gctgctgctg gacaggtacc agtaccacca ccatggccgc     60

ttcgacctga ccgttgggca atccatggtg cttaacaacg acagcgccat tgctagccat    120

cagatctatg gcgccgctgc gtactatccc ttctacggag cccaagctct gcacgggagg    180

gtgctcctgc cgccggcgat cgcggccgac gagccggtct acgtgaacgc caagcagttc    240

aacggcatcc tccggcggcg cctggcgcgc gccaagcgcg cggccgccac ggaccgccgg    300

gtctccggga gccgcaagcc gtacctccac gagtcacggc acctgcacgc gctgcgccgg    360

gcgcggggca ccggcggccg cttcctcaac acccggagcc gcgacggcga ccccgaggcc    420

ggcagcgcgg ggaaggcggc ggcggcggcg gcgaggatgc aggaggagga ccggcaggcg    480
```

gacgccgtgt tcctctcgtc gttggcgagc atggcgggcg gcgaggccac ccggtggccc 540
agcgcgccgt cgcgggggcg gggctgctgc gacctgctca aggcgtga 588

<210> SEQ ID NO 17
<211> LENGTH: 195
<212> TYPE: PRT
<213> ORGANISM: Zea mays

<400> SEQUENCE: 17

Met Ala Ala His Pro Glu Leu Leu Leu Leu Asp Arg Tyr Gln Tyr His
1 5 10 15

His His Gly Arg Phe Asp Leu Thr Val Gly Gln Ser Met Val Leu Asn
20 25 30

Asn Asp Ser Ala Ile Ala Ser His Gln Ile Tyr Gly Ala Ala Ala Tyr
35 40 45

Tyr Pro Phe Tyr Gly Ala Gln Ala Leu His Gly Arg Val Leu Leu Pro
50 55 60

Pro Ala Ile Ala Ala Asp Glu Pro Val Tyr Val Asn Ala Lys Gln Phe
65 70 75 80

Asn Gly Ile Leu Arg Arg Arg Leu Ala Arg Ala Lys Arg Ala Ala Ala
85 90 95

Thr Asp Arg Arg Val Ser Gly Ser Arg Lys Pro Tyr Leu His Glu Ser
100 105 110

Arg His Leu His Ala Leu Arg Arg Ala Arg Gly Thr Gly Gly Arg Phe
115 120 125

Leu Asn Thr Arg Ser Arg Asp Gly Asp Pro Glu Ala Gly Ser Ala Gly
130 135 140

Lys Ala Ala Ala Ala Ala Ala Arg Met Gln Glu Glu Asp Arg Gln Ala
145 150 155 160

Asp Ala Val Phe Leu Ser Ser Leu Ala Ser Met Ala Gly Gly Glu Ala
165 170 175

Thr Arg Trp Pro Ser Ala Pro Ser Arg Gly Arg Gly Cys Cys Asp Leu
180 185 190

Leu Lys Ala
195

<210> SEQ ID NO 18
<211> LENGTH: 1711
<212> TYPE: DNA
<213> ORGANISM: Zea mays

<400> SEQUENCE: 18
accacccaaa taagcataaa tagtagtggt tgattgtgta attccagaga tataaacgaa 60
tatctctaga gatctgcctc atcaacagct gcagtatttg ctagccacat atatatacac 120
agttcgacac gtagttataa cggaagagag aagcaaagag agaggcagag tgactgcaac 180
catcagtagt tctatgattt tatttttac cgttttgttg ctgtttcatg gtgtttattt 240
gattgtaggg tggaggagag gtgaaagctg acagaagaga gtgagcacac atggtgcctt 300
tcttgcatga tgtatgatcg agagagttca tgctcgaagc tatgcgtgct cacttctctc 360
tctgtcagcc attagaactc ctctatctct caatctcgat ctccctcttt ctttgttgat 420
ctctcccatg gtgatattta tttgcttcct acgtgttgtg ttctctttct tcagcacaca 480
cacaacctgt tcatgttacc ttagggttaa agtttttgca ctttgcgtga agatggaaag 540
acaaacagta gatgagtttt ttgaaggttt gacagaagag agtgagcaca cacggtggtt 600

-continued

```
tcttaccatg agtgtcatgc taggagctgt gcgtgctcac cctctatctg tcagtcactc    660

atcaagccca tctgtcttat tagcttgttt ccgctgctaa taaatattct agactcaagt    720

ttatttgaca cagagatcga tcgctatctt gttcgatgca tatatatata tatatataga    780

agtattattt acatgtgcgg atctcgtgta tatcttcttc ctgattagct gatgatctta    840

ttctcatgtg tagtttattt gtcttcgtat ctaacttttt cgcaggggcc aagccatgat    900

tgcgaagaaa ggaatgtaaa agatggctca gaactccatc acaaagtcta catacggtcg    960

aaataagatc tccatcagat cggagagctt tatttattga ttgttttttt agagttctag   1020

agcaaagccc atgtcttagc attaccaaga caaaagaata atccatatat atatcctttg   1080

gatggttcac atccttcact ccaggtttaa gtttaaccaa cacaaataaa aatatataat   1140

taaacgaccg gcacatagag acaaaaactc aaatctccaa gaacatctcc actgtcagca   1200

gcctccaagg taaaccataa attttcaatg gaacgatcat caaccaccag ggaggaggat   1260

atatagcctc tgctcttcaa atcttcaggt cttgtggcca gattcttgag tttctccagc   1320

ttcactttga agtccagttt ctatgcctga aggcagagca gcctcagcct tgcttgtagc   1380

atgactgcca tgttcaagag taaagacctc gtgtctctaa ggaacaccat gaaaacacag   1440

ttgtttcgtg tcagtttcga aagcctccac agggctgcaa gaatcatttg tgtagtagtg   1500

gtggttgacg tactctctct caaagaaaga acatcatgtt tcttaggttg ttttttagtg   1560

cgccttcatt tcattctctg aatatgccca taagctttag ttgaacatac tgatatgtaa   1620

atttggctcg gtggctcacc gttattgcat gtgcagaatt tatggcactg gtctgattta   1680

tatgaaaata ttttatattg ttgtggcttt a                                  1711


<210> SEQ ID NO 19
<211> LENGTH: 719
<212> TYPE: PRT
<213> ORGANISM: Sorghum bicolor

<400> SEQUENCE: 19

Met Ser Asp Asp Asp Asp Gly Val Asp Pro Glu Ile Glu Asp Val Asn
1               5                   10                  15

Gly Tyr Tyr Phe Glu Asp Gly Glu Gly Glu Pro Val Cys Phe Ser Ile
            20                  25                  30

Leu Pro Phe Gln Phe Gly Glu Asn Asp Asn Glu Ala Asp Phe Ser Arg
        35                  40                  45

Lys Asn Val Phe Leu His Gly Phe Val Asp Gln Ser Pro His Val Tyr
    50                  55                  60

Lys Glu Val Val Ala Trp Lys Ile Leu Gln Arg Leu Ile Glu Asn Gly
65                  70                  75                  80

Phe Glu Arg Thr Lys Lys Val Cys Met Glu Asn Lys Thr Gln Arg Ala
                85                  90                  95

Leu Gln Leu Ala Val Cys Arg Arg Cys Pro Arg Ala Tyr His Trp Glu
            100                 105                 110

Cys Leu Pro Arg Glu Leu Ser Leu Gly Ala Lys Asp Lys Asp Gly Asn
        115                 120                 125

Pro Arg Ala Trp Lys Leu Ser Lys Thr Ile Phe Phe Tyr Cys Leu Asp
    130                 135                 140

His Glu Ile Asp Lys Asp Thr Arg Thr Ala Ser Arg Asn His Ile Lys
145                 150                 155                 160

Phe Pro Ala Thr Pro Glu Cys Thr Lys Thr Lys Glu Leu Gly Asn Arg
                165                 170                 175
```

-continued

```
Lys Gly Arg Met Thr Gly Lys Arg Arg Lys Asn Thr Asp Gln Ser Thr
            180                 185                 190

Glu Pro Thr Glu Leu Ser Asn Arg Leu Tyr Gly Ala Glu Ser Glu Gln
        195                 200                 205

Ala Asp Asn Val Gly Ala Lys Ser Thr Ser Pro Gln Ile Val Val Glu
    210                 215                 220

Pro His Cys Ala Ala Lys Val Leu Lys Gly Asp Pro Gln Ile Glu Gln
225                 230                 235                 240

Ser Ile Ile Gly Val Ala Gly Ser Gln Asn Gly Ala Glu Thr Met Asn
                245                 250                 255

Gly His Glu Lys Gln Phe Gly Ile Ser Cys Val Ala Arg Thr Glu Thr
            260                 265                 270

Glu Lys Arg Val Thr Tyr Leu Ala Gln Lys Gly Thr Cys Leu Gly Thr
        275                 280                 285

Pro Tyr Asp Gly Pro Ser Thr Lys Asp Met Ser Asp Cys Ser Val Gln
    290                 295                 300

Asp Thr Pro Val Asp Lys Asp Phe Glu Leu Asp Asn Val Ala Tyr Arg
305                 310                 315                 320

Ile Met Glu Asp Lys Tyr Ala Asn Gly Arg Glu Glu Thr Gln Glu Asp
                325                 330                 335

Tyr Thr Arg Lys Glu Thr Ala His Arg Lys Asp Ser Ser Glu Asn Gln
            340                 345                 350

Gly Gln Asn Asp Val Leu Glu Leu Asp Asn Leu Trp Val Glu Ile Gln
        355                 360                 365

Ala Asp Gly Ser Pro Leu Glu Pro Gly Asn Lys Arg Tyr Lys Glu Glu
    370                 375                 380

Asn Ala Tyr Gly Leu Gly Ser Ala Ser Gly His Glu Lys Glu Thr Ser
385                 390                 395                 400

Ser Ser Arg Arg Glu Asn Val Gln Ser Asp Arg Gly Met Val Pro Met
                405                 410                 415

Asn Asp Ser Lys Thr Ile Asp Tyr Arg Lys Gly Gly Thr Thr Leu Asp
            420                 425                 430

Asn Asn Val Tyr Asp His Ser Ser Glu Gly Ser Tyr Pro Cys Gln Gly
        435                 440                 445

Glu Cys Ser His Ser Lys Cys Asn Asp Gly Leu Val Ala Ile Asp Gln
    450                 455                 460

Asp Thr Ser Ser Asp Arg Leu Lys Lys Arg Ser Gln Pro Val Glu Lys
465                 470                 475                 480

Ala Ser Asp Gly Asn Lys Thr Asp Leu Asp Lys Asn Lys Lys His Asn
                485                 490                 495

Leu Lys Glu Asp Gly Arg Asp Ala His Tyr Glu Asp Arg Arg Thr Glu
            500                 505                 510

Arg Asn Thr Ala Ala Asp Thr Ser Arg Tyr Lys Cys Arg Asp Lys Ile
        515                 520                 525

Gln Leu Asp Arg Arg Glu Pro Glu Leu Val Gly Arg Asn Thr Arg Ala
    530                 535                 540

Arg Ser Ser Glu His Ser Pro Glu Arg Gln Arg Met Glu Arg Asp Gly
545                 550                 555                 560

Ser Tyr Pro Gly Thr Tyr Asn Arg Arg Arg Tyr Glu Ser Leu His Asn
                565                 570                 575

Phe Asn Pro Pro Arg Ser Gly Cys Asp Asp Arg Arg Gln Leu Ser Pro
            580                 585                 590

Cys Gln Ser Ser Phe Pro Leu Pro Glu Phe Cys Gly Asp His Ser His
```

-continued

```
        595                 600                 605

Leu Tyr Pro Arg Asp Ser Thr Ile Gly Arg His Asn Pro His Arg Tyr
    610                 615                 620

Leu Gly Ile Pro Gln Tyr Gly Pro Tyr Met Ala Ala Ser Ala Ala Gly
625                 630                 635                 640

His Ser Ala Val Cys Tyr Arg Leu Ala Gly Gly Tyr Gly Glu Gly Ser
                645                 650                 655

Arg Ala Ser Arg Pro Val Thr Asp Trp Tyr Ala Pro His Leu Asp Arg
            660                 665                 670

Thr Asn Cys Gln Pro Arg Ser Gln Ile Asp Leu Gln Leu Gln Ala Ser
        675                 680                 685

Arg Pro Val Thr Asp Lys Tyr Ala Pro Gln Leu Glu Leu Thr Asn Tyr
    690                 695                 700

Pro Pro Arg Ser Gln Ser Asp Leu Gln Tyr Cys Thr Thr Thr Ile
705                 710                 715
```

EXTENDING JUVENILITY IN GRASSES

This application is a divisional of U.S. application Ser. No. 13/834,114, filed Mar. 15, 2013 (pending), which application claims the benefit of U.S. Provisional Appl. Ser. No. 61/651,540 filed May 24, 2012, the entire disclosures of which are incorporated herein by reference.

STATEMENT REGARDING FEDERALLY SPONSORED RESEARCH OR DEVELOPMENT

This invention was made with Government support under DE-FC02-07ER64494 awarded by the U.S. Department of Energy. The Government has certain rights in the invention.

INCORPORATION OF SEQUENCE LISTING

The sequence listing that is contained in the file named "WARF103US_ST25.txt", which is 116,564 bytes (measured in MS-WINDOWS) and was created on Mar. 15, 2013, is filed herewith by electronic submission and incorporated herein by reference.

BACKGROUND OF THE INVENTION

Field of the Invention

The invention relates to methods and compositions for altering the juvenile phase of growth of plants.

Background of the Invention

Juvenile and adult vegetative tissues in grasses differ dramatically in anatomy, biochemical composition, and in their ability to withstand biotic and abiotic stresses. Juvenile plants cannot flower and are capable of only vegetative growth. Juvenile leaf tissue further has inherent resistance to specific abiotic stresses such as cold and drought, is generally less recalcitrant when used for processing for biofuels, and may be more digestible when used as feed. Researchers have identified certain parameters such as age, leaf number, and certain growth conditions as playing a role in the maturation of juvenile plant tissue to adult plant tissue. However, the genetic triggers controlling the transition between juvenile and adult tissue in plants has not been well understood. Therefore, increasing the proportion of the plant that is juvenile has potential benefit for improving the yield and processing ability of plant biomass, among other agronomic traits.

SUMMARY OF THE INVENTION

In one aspect the invention provides a polynucleotide molecule comprising a sequence selected from the group consisting of: (a) a sequence encoding a polypeptide at least 85% identical to SEQ ID NO:3, SEQ ID NO:5, SEQ ID NO:7, SEQ ID NO:9, or SEQ ID NO:17; wherein the polypeptide regulates juvenile to adult phase change in grass plant leaves; (b) a sequence comprising SEQ ID NO:2, SEQ ID NO:4, SEQ ID NO:6, SEQ ID NO:8, or SEQ ID NO:16; (c) a sequence hybridizing to (b) under wash conditions of 0.15 M NaCl and 70° C. for 10 minutes, wherein the sequence encodes a protein that regulates juvenile to adult phase change in grass plant leaves; (d) a sequence comprising at least 85% sequence identity over its full length to the full length of SEQ ID NO:2 or SEQ ID NO:16, wherein the sequence encodes a protein that regulates juvenile to adult phase change in grass plant leaves; and (e) a sequence complementary to (a), (b), (c) or (d), further wherein the polynucleotide molecule is operably linked to a heterologous promoter functional in plants. In a particular embodiment the polynucleotide molecule comprises the coding sequence of SEQ ID NO:2. In another embodiment the polynucleotide molecule comprises the coding sequence of SEQ ID NO:16.

Other embodiments of the invention provide a recombinant vector comprising such a polynucleotide molecule. In certain embodiments, the invention provides the recombinant vector, further comprising an additional polynucleotide sequence which, after being transcribed, regulates the timing of the juvenile to adult phase change in a plant. Thus, in particular embodiments the recombinant vector may comprise an additional polynucleotide sequence which encodes all or part of a sequence selected from the group consisting of: Glossy15, Cg1, a homolog of either thereof, and/or a sequence complementary thereto.

In some embodiments the recombinant vector further comprises at least one additional sequence chosen from the group consisting of: a regulatory sequence such as a promoter, a selectable marker, a leader sequence and a terminator. The additional sequence may be a heterologous sequence. In some embodiments the promoter is a tissue-specific promoter. In a particular embodiment the promoter directs expression in leaf tissue. In certain embodiments the recombinant vector may be defined as an isolated expression cassette.

In other embodiments, the recombinant vector comprises a first sequence selected from the group consisting of: (a) a sequence encoding a polypeptide at least 85% identical to SEQ ID NO:3, SEQ ID NO:5, SEQ ID NO:7, SEQ ID NO:9, or SEQ ID NO:17; wherein the polypeptide regulates juvenile to adult phase change in grass plant leaves; (b) a sequence comprising SEQ ID NO:2, SEQ ID NO:4, SEQ ID NO:6, SEQ ID NO:8; or SEQ ID NO:16; (c) a sequence hybridizing to (b) under wash conditions of 0.15 M NaCl and 70° C. for 10 minutes, wherein the sequence encodes a protein that regulates juvenile to adult phase change in grass plant leaves; (d) a sequence comprising at least 85% sequence identity over its full length to the full length of SEQ ID NO:2 or SEQ ID NO:16, wherein the sequence encodes a protein that regulates juvenile to adult phase change in grass plant leaves; and (e) a sequence complementary to (a), (b), (c) or (d), or a fragment thereof; and a second sequence comprising the reverse complement of the first sequence, wherein the expression of the construct in a plant down regulates the expression of a coding sequence and/or encoded polypeptide in the plant. Some embodiments of the invention provide the recombinant vector further comprising an additional polynucleotide sequence which, after being transcribed, regulates the timing of the juvenile to adult phase change in a plant.

Another aspect of the invention is a transgenic plant or seed comprising a recombinant vector comprising a polynucleotide molecule comprising a sequence selected from the group consisting of: (a) a sequence encoding a polypeptide at least 85% identical to SEQ ID NO:3, SEQ ID NO:5, SEQ ID NO:7, SEQ ID NO:9, or SEQ ID NO:17; wherein the polypeptide regulates juvenile to adult phase change in grass plant leaves; (b) a sequence comprising SEQ ID NO:2, SEQ ID NO:4, SEQ ID NO:6, SEQ ID NO:8, or SEQ ID NO:16; (c) a sequence hybridizing to (b) under wash conditions of 0.15 M NaCl and 70° C. for 10 minutes, wherein the sequence encodes a protein that regulates juvenile to adult phase change in grass plant leaves; (d) a sequence comprising at least 85% sequence identity over its full length to the full length of SEQ ID NO:2 or SEQ ID NO:16, wherein the sequence encodes a protein that regulates juvenile to adult phase change in grass plant leaves; and (e) a sequence complementary to (a), (b), (c) or (d), further wherein the polynucleotide molecule is operably linked to a heterologous promoter functional in plants. In yet other embodiments, the transgenic plant may comprise a recombinant vector as described above, comprising an additional polynucleotide sequence which, after being transcribed, regulates the timing of the juvenile to adult phase change in the plant.

Yet another aspect of the invention is a transgenic plant or seed comprising a first sequence selected from the group consisting of: (a) a sequence encoding a polypeptide at least 85% identical to SEQ ID NO:3, SEQ ID NO:5, SEQ ID NO:7, SEQ ID NO:9, or SEQ ID NO:17; wherein the polypeptide regulates juvenile to adult phase change in grass plant leaves; (b) a sequence comprising SEQ ID NO:2, SEQ ID NO:4, SEQ ID NO:6, SEQ ID NO:8, or SEQ ID NO:16; (c) a sequence hybridizing to (b) under wash conditions of 0.15 M NaCl and 70° C. for 10 minutes, wherein the sequence encodes a protein that regulates juvenile to adult phase change in grass plant leaves; (d) a sequence comprising at least 85% sequence identity over its full length to the full length of SEQ ID NO:2 or SEQ ID NO:16, wherein the sequence encodes a protein that regulates juvenile to adult phase change in grass plant leaves; and (e) a sequence complementary to (a), (b), (c) or (d), or a fragment thereof; and a second sequence comprising the reverse complement of the first sequence, wherein the expression of the construct in a plant down regulates the expression of a coding sequence and/or encoded polypeptide in the plant.

In some embodiments the transgenic plant may further be defined as a monocotyledonous plant. In particular embodiments the transgenic plant is further defined as a member of the Poaceae. In more particular embodiments the transgenic plant is further defined as a member of the Panicoideae or the Pooideae. In yet more particular embodiments the transgenic plant may further be defined as maize, rice, sorghum, or switchgrass.

The invention also provides a seed or cell of such a transgenic plant wherein the seed or cell comprises recombinant vector.

In certain embodiments the plant is a plant wherein the last leaf with epicuticular wax is produced later during plant development relative to that found in an otherwise isogenic plant lacking the recombinant vector.

In another aspect, the invention provides a method of altering the timing of juvenile to adult phase change in a plant, the method comprising modulating the expression of GRMZM2G362718 or GRMZM2G90616, or a homolog of either thereof, in the plant. Other contemplated embodiments of such methods further comprise modulating the expression of at least a second gene which regulates the timing of the juvenile to adult phase change in a plant. In particular embodiments the second gene is selected from the group consisting of Glossy15 and Cg1. Thus in some embodiments the method comprises expressing a recombinant vector or construct, as defined above, in the plant. In certain embodiments, the timing of the juvenile to adult phase change is extended (delayed) relative to a wild type plant (i.e. an otherwise essentially isogenic plant not comprising such a recombinant construct). In some embodiments the method comprises mutagenizing said GRMZM2G362718 or GRMZM2G90616 or a homolog thereof.

In certain embodiments of the method, the timing of juvenile to adult phase in the plant is extended relative to a wild type plant. In particular embodiments, the timing of juvenile to adult phase change is calculated by a method comprising counting the last leaf displaying epicuticular wax.

In some embodiments of the method, the plant exhibits a trait selected from the group consisting of: an increase of at least one in the numbering of the last leaf which displays epicuticular wax or which does not contain abaxial trichomes; an altered proportion of juvenile, transitional, or adult leaves; enhanced yield of vegetative tissue; enhanced digestibility of vegetative tissue; enhanced resistance to a plant pest; and enhanced resistance to a plant disease. In certain embodiments of the method, the plant has altered development or morphology when compared to a wild type plant, further wherein the plant displays a trait selected from the group consisting of: enhanced disease resistance, enhanced insect resistance, improved forage digestibility, enhanced abiotic stress tolerance, and improved utility for biofuel production.

Yet another aspect of the invention provides a method of producing plant biomass, the method comprising: (a) obtaining a plant comprising a recombinant vector as described above; and (b) preparing biomass from said plant or a part thereof. In certain embodiments the method further comprises producing biofuel from the biomass. The method may also comprise producing food or feed from the biomass.

BRIEF DESCRIPTION OF THE DRAWINGS

FIG. 2 depicts a CLUSTAL protein alignment of GRMZM2G362718 with *Arabidopsis* homolog AT5G55390.1.

FIG. 3 shows a CLUSTAL protein alignment of GRMZM2G362718 with homologs from sorghum and rice.

FIG. 5 depicts a summary table of studies providing phenotypic data from defined mapping populations.

BRIEF DESCRIPTION OF THE SEQUENCES

Figure 1:
FIG. 1 depicts a maize transition leaf, with areas of juvenile tissue, and other areas of adult tissue.

SEQ ID NO:1 GRMZM2G362718 genomic nucleotide sequence from *Z. mays* B73.

SEQ ID NO:2 GRMZM2G362718 nucleotide coding sequence from *Z. mays* B73, with UTR.

SEQ ID NO:3 GRMZM2G362718 predicted protein sequence from *Z. mays* B73.

SEQ ID NO:4 GRMZM2G362718 nucleotide coding sequence from *Z. mays* Mo17.

SEQ ID NO:5 GRMZM2G362718 predicted protein sequence from *Z. mays* Mo17.

SEQ ID NO:6 GRMZM2G362718 nucleotide coding sequence from *Z. mays* Oh43.

SEQ ID NO:7 GRMZM2G362718 predicted protein sequence from *Z. mays* Oh43.

SEQ ID NO:8 GRMZM2G362718 nucleotide coding sequence from *Z. mays* W64A.

SEQ ID NO:9 GRMZM2G362718 predicted protein sequence from *Z. mays* W64A.

SEQ ID NO:10 Predicted protein sequence of AT5G55390.1 from *Arabidopsis thaliana.*

SEQ ID NO:11 Predicted protein sequence of Os08g24946.1 from *Oryza sativa.*

SEQ ID NO:12 Predicted protein sequence of Sb02g003420.1 from *Sorghum bicolor.*

SEQ ID NO:13 Predicted protein sequence of Bradi4g27190.1 from *Brachypodium distachyon.*

SEQ ID NO:14 Glossy15 nucleotide coding sequence from *Z. mays* W64A (GenBank U41466).

SEQ ID NO:15 Glossy15 predicted protein sequence from *Z. mays* W64A.

SEQ ID NO:16 GRMZM2G096016 nucleotide coding sequence from *Z. mays.*

SEQ ID NO:17 GRMZM2G096016 predicted protein sequence from *Z. mays.*

SEQ ID NO:18 Cg1 nucleotide coding sequence for miR156 transcripts.

DETAILED DESCRIPTION OF THE INVENTION

The invention provides a gene, and methods for its use, to modulate the transition of plant tissue from the juvenile to the adult phase of growth. By modulate is meant to either hasten or delay such transition. A plant or product comprising a recombinant DNA construct comprising such a gene may exhibit improved properties relating to, for instance, biofuel production and/or processing, use as animal feed, and resistance to a plant pest or plant disease, and is also an aspect of the invention. Seed of such a plant is also an aspect of the invention. Thus, for instance, one or more agronomic traits of a grass, such as a member of the Poaceae including corn, sorghum, rice, and switchgrass, among others, may be enhanced. Such traits may include one or more of: improved vegetative yield; reduced recalcitrance during biofuel processing; improved resistance to a plant pest such as European Corn Borer; improved resistance to a plant disease such as a rust disease; enhanced cold tolerance; enhanced digestibility of an animal feed ingredient such as plant vegetative tissue; and improved nutritional content of plant vegetative tissue.

GRMZM2G362718 is a gene of previously unknown function in corn (maize) which was identified through chromosomal mapping of juvenile plant tissue, and apparently functions as a trigger of juvenile to adult growth phase change. Predicted protein alignments (e.g. FIGS. 2-3) show that this gene encodes a protein with some similarity to the enhanced downy mildew 2-transcription factor (EDM2) of *Arabidopsis*, rice, *Brachypodium*, and sorghum (displaying approximately 52.9, 56.7, 42.9, 63.2, percent similarity, respectively). Modulating, such as disrupting, the expression of GRMZM2G362718 may alter, such as extend, the temporal duration during which a plant is in a juvenile phase of growth. Homologs of GRMZM2G362718 exist in other plant species such as *Arabidopsis*, rice (*Oryza sativa*), *Brachypodium*, and sorghum (*Sorghum bicolor*), among others; see exemplary sequence database accession numbers AT5G55390.1, Os08g24946.1, Bradi4g27190.1, and Sb02g003420.1, respectively (SEQ ID NOs: 10-13), so this effect may be seen in other plants, e.g. monocotyledonous plants such as grass plants (e.g. members of the Poaceae such as maize, rice sorghum, or switchgrass), as well as dicotyledonous plants.

An additional genome wide association analysis, using transcript presence/absence as the dependent variable, identified GRMZM2G096016 (LOC100285984; Maize Genome Sequencing Project; MaizeSequence.org; Schnable et al. *Science,* 326:1112, 2009) on chromosome 2 as also being associated with a change in the timing of production of the last juvenile leaf, e.g. when vegetative phase change was scored by identifying the last leaf with epicuticular wax. Although close in proximity (~24.5 Kb) to the first candidate gene underlying this QTL (i.e. GRMZM2G362718), GRMZM2G096016, which encodes a predicted nuclear transcription factor Y-subunit A-10, is not in linkage disequilibrium with EDM2. Thus, in particular embodiments, the invention provides methods and compositions for modulating expression of GRMZM2G362718 and/or GRMZM2G096016, each found on maize chromosome 2, or homologs thereof, in order to alter the timing of vegetative phase change in maize, rice, sorghum, switchgrass, or other plants.

MicroRNAs play an important role in regulating the timing of plant developmental transitions. By regulating transcripts of developmental genes, miRNAs control some aspects of leaf morphology, polarity and floral organ identity, and some stress responses (Willmann and Poethig, *Curr. Opin. Plant Biol.* 8:548-552, 2005) as well as the timing of juvenile to adult vegetative phase change. The maize and *Arabidopsis* signaling pathway and miRNA expression cascade are similar (Nonogaki, Plant Cell Physiol. 51:1840-1846, 2010). In maize, the Corngrassl (Cg1) mutant retains juvenile traits resulting in initiation of tillers at each leaf axil causing a bush-like appearance. This phenotype is due to the ectopic overexpression of two tandem miR156 genes (Chuck et al., *Nature Genetics* 39:544-549, 2007; Chuck et al., *PNAS* 108:17550-17555, 2011; GenBank: GQ905502.1). miR156 targets SBP-domain transcription factors—teosinte glume architecturel (tga1) in maize and SPL13 in *Arabidopsis*. SPB transcription factors up regulate miR172 in both species and miR172 targets AP2-like transcription factors such as glossy15 in maize and SCHNARCHSAPFEN (SNZ) in *Arabidopsis*. Glossy15 maintains expression of juvenile traits in the leaf epidermis and suppresses adult traits. Mutants of glossy15 (Gl15) show premature vegetative phase change to the adult state (Evans et al., *Devel.* 120:1971-1981, 1994). In Cg1 mutants of maize, the overexpression of miR156 causes a decrease in tga1 and miR172 (Chuck, 2007, ibid), which cause an increase in expression of Glossy15.

In further embodiments, the invention provides methods and compositions for modulating the expression of one or more additional genes involved in regulating the juvenile to adult growth phase change, in conjunction with modulating expression of GRMZM2G362718 and/or GRMZM2G096016, or homologs thereof. Thus, for instance, the expression of Glossy15 (Gl15; GRMZM2G160730), or Cg1, or a homolog thereof, may be modulated along with modulation of expression of GRMZM2G362718 and/or GRMZM2G096016, or a homolog thereof, in a plant.

I. NUCLEIC ACIDS, POLYPEPTIDES AND PLANT TRANSFORMATION CONSTRUCTS

Certain embodiments of the current invention concern polynucleotide sequences comprising a GRMZM2G362718 coding sequence, or a GRMZM2G096016 coding sequence. Exemplary coding sequences for use with the invention include SEQ ID NO: 2, SEQ ID NO:4, SEQ ID NO:6, SEQ ID NO:8, and SEQ ID NO:16, encoding the polypeptides of SEQ ID NO: 3, SEQ ID NO:5, SEQ ID NO:7, SEQ ID NO:9, and SEQ ID NO:17, respectively. Constructs may also be designed that are complementary to all or part of the promoter and other control regions, exons, introns or even exon-intron boundaries of a gene.

Other contemplated constructs may be designed which, in addition to a GRMZM2G362718 coding sequence, GRMZM2G096016 coding sequence, or homolog thereof, also comprise all or part of a Glossy15 or Cg1 and/or other coding sequence, wherein such additional sequence also modulates the juvenile to adult growth phase change. Thus for instance, such constructs, in addition to comprising all or part of a GRMZM2G362718 coding sequence, or homolog thereof, may further comprise, for instance, a Glossy15 coding sequence, or homolog thereof. Exemplary coding sequences for use with the invention therefore include SEQ ID NO:14, encoding the polypeptide of SEQ ID NO:15, and SEQ ID NO:18.

The invention provides a nucleic acid sequence identical over its entire length to each coding sequence provided herein. The invention further provides a nucleic acid sequence displaying at least 85%, 90%, 95%, or 99% identity over its entire length to a the full length, or a fragment, of the coding sequence provided herein. The invention also provides the coding sequence for the polypeptide or a fragment thereof, as well as the coding sequence for the polypeptide or a fragment thereof in a reading frame with other coding sequences, such as those encoding a leader or secretory sequence, a pre-, pro-, or prepro-protein sequence. The nucleic acid can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of a fused polypeptide. Nucleic acids of the present invention also include nucleic acids comprising a structural gene and the naturally associated sequences that control gene expression.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods. Computer programs can be used to determine "identity" between two sequences these programs include but are not limited to, GCG; suite of BLAST programs, three designed for nucleotide sequences queries (BLASTN, BLASTX, and TBLASTX) and two designed for protein sequence queries (BLASTP and TBLASTN). The BLASTX program is publicly available from NCBI and other sources (BLAST Manual, Altschul, S., et al., NCBI NLM NIH, Bethesda, Md. 20894; Altschul, S., et al., *J. Mol. Biol.* 215:403-410, 1990). The well known Smith Waterman algorithm can also be used to determine identity.

Parameters for polypeptide sequence comparison include the following: Algorithm: Needleman and Wunsch (*J. Mol. Biol.* 48:443-453, 1970); Comparison matrix: BLOSUM62 from Hentikoff and Hentikoff, (*PNAS* 89:10915-10919, 1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

The present inventors have identified chromosomal regions responsible for such growth, and in particular a specific candidate gene termed GRMZM2G362718 that may trap a plant in a juvenile phase of growth. Marker assisted breeding as well as methods of genetic modification may thus be used to introduce or introgress this gene, a modified version of this gene, or the described linkage group, into a plant to alter the timing of the juvenile to adult growth transition to achieve agronomic improvement. In certain embodiments of the invention, the process for producing such plants or lines comprises introducing a recombinant copy of GRMZM2G362718 or GRMZM2G096016, or a variant thereof into a plant. In other embodiments, the method comprises introgressing at least one chromosomal locus mapping to QTL bounded by markers mmc2184 and mmp183 on maize chromosome 2 into a plant. In other embodiments the function of a gene controlling the juvenile to adult phase change may be disrupted, allowing for enhanced juvenile growth, such as by delaying the juvenile to adult growth phase transition.

Vectors used for plant transformation may include, for example, plasmids, cosmids, YACs (yeast artificial chromosomes), BACs (bacterial artificial chromosomes) or any other suitable cloning system, as well as fragments of DNA there from. Thus when the term "vector" or "expression vector" is used, all of the foregoing types of vectors, as well as nucleic acid sequences isolated there from, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes.

II. ANTISENSE AND RNAI CONSTRUCTS

A polynucleotide construct of the present invention may comprise a DNA for expression of an antisense RNA, siRNA or miRNA, which modulates expression of a GRMZM2G362718 or GRMZM2G096016 coding sequence. By "modulates expression" is meant an increase or a decrease in such expression. Techniques for RNAi are well known in the art. Antisense and RNAi treatments represent one way of altering agronomic characteristics in accordance with the invention (e.g., by down regulation of a GRMZM2G362718 and/or GRMZM2G096016 coding sequence). In particular, constructs comprising a GRMZM2G362718 coding sequence, including fragments thereof (or a GRMZM2G096016 coding sequence or fragments thereof), in antisense orientation, or combinations of sense and antisense orientation, may be used to decrease or effectively eliminate the expression of a GRMZM2G362718 or GRMZM2G096016 coding sequence in a plant and to alter agronomic characteristics (e.g., leaf morphology or disease resistance). Accordingly, each of these may be used to "knock-out" the function of a GRMZM2G362718 or GRMZM2G096016 coding sequence or homologous sequences thereof.

III. GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts. These methods and their use are well known in the art.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. In an exemplary embodiment, MS media may be modified by including further substances such as growth regulators. Examples of such growth regulators are dicamba and 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, then transferred to media conducive to maturation of embryoids. Cultures are transferred as needed on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins m−2 s−1 of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at a suitable temperature, for instance about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Very frequently the expression of a gene product is determined by evaluating the phenotypic results of its expression. These assays also may take many forms including but not limited to analyzing changes in the chemical composition, morphology, or physiological properties of the plant. Morphological changes may include ones known to demonstrate juvenile characteristics in plant vegetative tissues, such as presence or absence of wax production, or trichome formation. Most often changes in response of plants or plant parts to imposed treatments are evaluated under carefully controlled conditions termed bioassays.

The present invention provides for a seed of a plant capable of producing a plant having enhanced juvenile growth. In one aspect, the plant can be an open-pollinated variety, a hybrid parent inbred line, or a male sterile line. In another aspect, the invention provides seed of a plant capable of producing a plant having enhanced juvenile growth.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5M abscisic acid and then transferred to growth regulator-free medium for germination.

In yet another aspect, tissue culture of the plants described herein relates to the culture of protoplasts, calli, or plant cells, that are isolated from, or present in, intact parts of the plants described herein.

Once plants are produced which display an enhanced, e.g. extended, juvenile phase of growth, the plants themselves can be cultivated in accordance with conventional procedures, including via tissue culture and by sexual reproduction. The seeds resulting from sexual reproduction can be recovered and planted or otherwise grown as a means of propagation. Plants may also be obtained through asexual reproduction. Protoplast or propagules (e.g., cuttings, scions or rootstocks) can be recovered from plants or parts thereof and may be employed to propagate additional plants.

The present invention also provides for and includes a container of seeds.

One aspect of the invention relates to vegetative tissues, including tissues harvested, dried, or otherwise processed, biomass produced by a plant having a genome that comprises at least one genetic locus giving rise to an enhanced juvenile phase of growth.

The present invention also provides progeny of plants displaying extended juvenile growth. As used herein, progeny include not only, without limitation, the products of any cross (be it a backcross or otherwise) between two plants, but all progeny whose pedigree traces back to the original cross.

One embodiment of the present invention provides for a plant that contains a genetic marker linked to one or more locus allowing for extended juvenile growth. By "extended juvenile growth locus" or "enhanced juvenile growth locus" is meant a locus that contributes to such extended or enhanced juvenile growth either alone or in combination with one more other locus.

IV. DEFINITIONS

As used herein, a "desirable trait" or "desirable traits" include, but are not limited to: increased vegetative growth, improved vegetative yield, improved digestibility when used as animal feed, and improved processing of biomass for preparation of, for instance, biofuel, among others.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found, or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs) a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, dsRNA, a transcriptional profile, and a methylation pattern may comprise polymorphisms. In addition, the presence, absence, or variation in copy number of the preceding may comprise a polymorphism.

As used herein, "genotype" is the actual nucleic acid sequence at a locus in an individual plant. As used herein, "phenotype" means the detectable characteristics (e.g. number of juvenile leaves, or timing of production of leaves displaying adult morphological characteristics, such as the presence of waxes) of a cell or organism which can be influenced by genotype.

As used herein, linkage of two nucleic acid sequences, including a nucleic acid marker sequence and a nucleic acid sequence of a genetic locus imparting a desired trait may be genetic or physical or both. In one aspect of the invention, the nucleic acid marker and genetic locus conferring an enhanced juvenile growth trait are genetically linked, and exhibit a LOD score of greater than 2.0, as judged by interval mapping for the trait based on maximum likelihood methods described by Lander and Botstein, 1989 (*Genetics,* 121:185-199), and implemented in the software package MAPMAKER (e.g. Lander et al., *Genomics* 1:174-181, (1987); default parameters). Alternatively, other software such as QTL Cartographer v1.17 (Basten et al., Zmap—a QTL cartographer. In: Proceedings of the 5th World Congress on Genetics Applied to Livestock Production: Computing Strategies and Software, edited by C. Smith, J. S. Gavora, B. Benkel, J. Chesnais, W. Fairfull, J. P. Gibson, B. W. Kennedy and E. B. Burnside. Volume 22, pages 65-66. Organizing Committee, 5th World Congress on Genetics Applied to Livestock Production, Guelph, Ontario, Canada, 1994; and Basten et al., QTL Cartographer, Version 1.17. Department of Statistics, North Carolina State University, Raleigh, N.C., 2004) may be used. Mapping of QTLs is well-described (e.g. WO 90/04651; U.S. Pat. Nos. 5,492, 547, 5,981,832, 6,455,758; reviewed in Flint-Garcia et al. 2003 (*Ann. Rev. Plant Biol.* 54:357-374, the disclosures of which are hereby incorporated by reference). In other embodiments, the marker and region conferring enhanced juvenile growth are genetically linked and exhibit a LOD score of greater than 3.0, or a LOD score of greater than 6.0, 9.0, 12.0, 15.0, or 18.0. In one embodiment, the marker and region contributing to such growth are genetically linked and exhibit a LOD score of between about 14 and about 20. When assigning the presence of a QTL, the LOD threshold score associated with a QTL analysis as described herein may be determined to be significant for instance at the 95% confidence level, or higher, such as at the 98% or 99% confidence level.

In another aspect, the nucleic acid marker is genetically linked at a distance of between about 0 and about 50 centimorgans (cM) to the locus of interest, e.g. a GRMZM2G362718 or GRMZM2G096016 coding sequence. In other embodiments, the distance between the nucleic acid marker and the locus of interest is between about 0 and about 35 cM, or between about 0 and about 25 cM, or between about 0 and about 15 cM, or between about 0 and about 10 cM, or between about 0 and about 5 cM, including less than about 4, 3, 2 or 1 cM.

As used herein, two nucleic acid molecules are said to be capable of hybridizing to one another if the two molecules are capable of forming an anti-parallel, double-stranded nucleic acid structure. Conventional stringency conditions are described by Sambrook et al., *Molecular Cloning*, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are known in the art, for example 6.0× sodium chloride/sodium citrate (SSC) at about 45° C., followed by a wash of 2.0×SSC at 50° C.; or can be found in *Current Protocols in Molecular Biology*, John Wiley & Sons, N.Y. (1989), 6.3.1-6.3.6. In some embodiments, hybridization conditions can be high, moderate or low stringency conditions. Preferred conditions include those using 50% formamide, 5.0×SSC, 1% SDS and incubation at 42° C. for 14 hours, followed by a wash using 0.2×SSC, 1% SDS and incubation at 65° C. Alternative wash conditions, such as of 0.15 M NaCl and 70° C. for 10 minutes may also be used.

The specificity of hybridization can be affected by post-hybridization washes. For example, the salt concentration in the wash step can be selected from a low stringency of about 2.0×SSC at 50° C. to a moderate stringency of about 1.0×SSC at 50° C. to a high stringency of about 0.2×SSC at 50° C.; or 0.15 M NaCl and 70° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid produced using that inbred. For example, if an inbred plant of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, ISSRs, or isozymes.

Additional markers, such as SSRs, AFLP markers, RFLP markers, RAPD markers, phenotypic markers, SNPs, isozyme markers, or microarray transcription profiles that are genetically linked to or correlated with the juvenile growth trait can be utilized (Walton, *Seed World* 22-29 (July, 1993); Burow and Blake, *Molecular Dissection of Complex Traits,* 13-29, Eds. Paterson, CRC Press, New York (1988)). Methods to isolate such markers and to design probes or primers useful in following the presence of such markers are known in the art. For example, locus-specific SSRs can be obtained by screening a genomic library for SSRs, sequencing of "positive" clones, designing primers which flank the repeats, and amplifying genomic DNA with these primers. Likewise, SNP markers may be identified as well.

The genetic linkage of marker molecules to the loci described herein can be established by a gene mapping model such as, without limitation, the flanking marker model, and the interval mapping, based on maximum likelihood methods described by Lander and Botstein, 1989 (*Genetics,* 121:185-199), and implemented in the software packages MAPMAKER (Whitehead Institute for Biomedical Research, Cambridge Mass., USA) or QTL Cartographer (North Carolina State University, Bioinformatics Research Center) or the like.

A maximum likelihood estimate (MLE) for the presence of a marker is calculated, together with an MLE assuming no trait effect, to avoid false positives. A $\log_{10}$ of an odds ratio (LOD) is then calculated as: LOD=$\log_{10}$ (MLE for the presence of a trait (MLE given no linked trait)).

The LOD score essentially indicates how much more likely the data are to have arisen assuming the presence of a resistance allele rather than in its absence. The LOD threshold value for avoiding a false positive with a given confidence, say 95%, depends on the number of markers and the length of the genome. Graphs indicating LOD thresholds are set forth in Lander and Botstein (1989), and further described by Ars and Moreno-Gonzalez, *Plant Breeding*, Hayward, Bosemark, Romagosa (eds.) Chapman & Hall, London, pp. 314-331 (1993), and van Ooijen (*Heredity* 83:613-624, 1999).

Selection of appropriate mapping or segregation populations is important in trait mapping. The choice of appropriate mapping population depends on the type of marker systems employed (Tanksley et al., Molecular mapping plant chromosomes. Chromosome structure and function: Impact of new concepts J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

Advanced breeding lines are collected from breeding programs. These are tested for their phenotype (e.g. their disease score reactions, the presence of adult leaves, an alteration in the relative proportion of juvenile vs. adult tissues, or an alteration in the timing of production of adult tissues, among others), and genotyped for markers in the QTL intervals described herein. From these data, the smallest genetic interval is identified within each QTL containing the donor parent (DP) favorable allele among the tested lines.

Considerable genetic information can be obtained from a completely classified $F_2$ population using a codominant marker system (Mather, Measurement of Linkage in Heredity: Methuen and Co., (1938)). An $F_2$ population is the first generation of self or sib pollination after the hybrid seed is produced. Usually a single $F_1$ plant is self or sib pollinated to generate a population segregating for the nuclear-encoded genes in a Mendelian (1:2:1) fashion.

In contrast to the use of codominant markers, using dominant markers often requires progeny tests (e.g., $F_3$ or back cross self families) to identify heterozygous individuals. The information gathered can be equivalent to that obtained in a completely classified $F_2$ population. This procedure is, however, often prohibitive because of the cost and time involved in progeny testing. Progeny testing of $F_2$ individuals is often used in map construction where error is associated with single plant phenotyping, or when sampling the plants for genotyping affects the ability to perform accurate phenotyping, or where trait expression is controlled by a QTL. Segregation data from progeny test populations (e.g., $F_3$ or backcrossed or selfed families) can be used in trait mapping. Marker-assisted selection can then be applied to subsequent progeny based on marker-trait map associations ($F_2$, $F_3$), where linkage has not been completely disassociated by recombination events (i.e., maximum disequilibrium).

Recombinant inbred lines (RILs) (genetically related lines; usually $>F_5$) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (e.g. Reiter et al., 1992; *Proc. Natl. Acad. Sci.* (*U.S.A.*) 89:1477-1481). However, as the distance between markers becomes larger (i.e., loci become more independent), the information in RIL populations decreases dramatically when compared to codominant markers.

Backcross populations can be utilized as mapping populations. A backcross population (BC) can be created by crossing an $F_1$ to one of its parents. Typically, backcross populations are created to recover the desirable traits (which may include most of the genes) from one of the recurrent parental (the parent that is employed in the backcrosses) while adding one or a few traits from the second parental, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., 1992; *Proc. Natl. Acad. Sci.* (*U.S.A.*) 89:1477-1481).

Information obtained from backcross populations using either codominant or dominant markers is less than that obtained from completely classified $F_2$ populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci polymorphic between the parentals are expected to segregate in the highly homozygous NIL population. Those loci that are polymorphic in a NIL population, however, are likely to be linked to the trait of interest.

Bulk segregant analysis (BSA) is a method developed for the rapid identification of linkage between markers and traits of interest (Michelmore, et al., 1991; *Proc. Natl. Acad. Sci.* (*U.S.A.*) 88:9828-9832). In BSA, two bulk DNA samples are drawn from a segregating population originating from a single cross. These bulk samples contain individuals that are identical for a particular trait (e.g., resistant or susceptible to a particular pathogen) or genomic region but arbitrary at unlinked regions (i.e., heterozygous). Regions unlinked to the target trait will not differ between the bulked samples of many individuals in BSA.

In another aspect, the present invention provides a method of producing a plant displaying enhanced juvenile growth comprising: (a) crossing a plant displaying such growth with a plant lacking such growth to form a segregating population; (b) screening the population for amount and/or duration of juvenile growth; and (c) selecting one or more members of the population having said enhanced or extended juvenile growth.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new plant lines requires the development and selection of varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Descriptions of other breeding methods that are commonly used for different traits and crops can be found in one of several available reference books (e.g., Fehr, *Principles of Cultivar Development* Vol. 1, pp. 2-3 (1987)).

The present invention also provides for parts of the plants produced by a method of the present invention. Parts of grass plants, without limitation, include plant cells or parts of plant cells, seed, endosperm, meristem, flower, anther, ovule, pollen, fruit, flowers, stems, roots, stalks or leaves, scions, and root stocks. Plant parts also include the parts of a fruit. In one embodiment of the present invention, the plant part is a seed.

In other aspects of the invention, the plants bearing one or more desirable traits in addition to enhanced juvenile growth may display a greater than 10%, or a greater than 30%, or a greater than 60%, or a greater than 80% reduction in foliar symptoms of, for instance, European corn borer damage on the second leaf above the ear (Riedeman, et al., 2008*; Crop Sci.* 48:1723-1731), relative to a an otherwise isogenic control plant. Additionally, juvenile leaves from plants displaying enhanced juvenile growth may comprise increased content of total uronosyl acids, arabinose, and galactose; decreased lignification, decreased neutral sugars, decreased glucose and xylose; decreased ester-linked monomers of p-coumaric acid, and decreased levels of ferulates, among other changes. Such changes may, for instance, beneficially allow for improved efficiency for biofuel production or allow for enhanced feed digestibility or nutritional content.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Genetic Structure of Juvenile to Adult Phase Change in Maize

Juvenile and adult vegetative tissues in grasses differ dramatically in anatomy, biochemical composition, and in their ability to withstand biotic and abiotic stresses. A maize transition leaf, with juvenile tissue distinguished by the presence of epicuticular wax with a dull blueish appearance is shown in FIG. 1. Dark glossy green portions of the leaf are adult tissue.

Figure 4A:
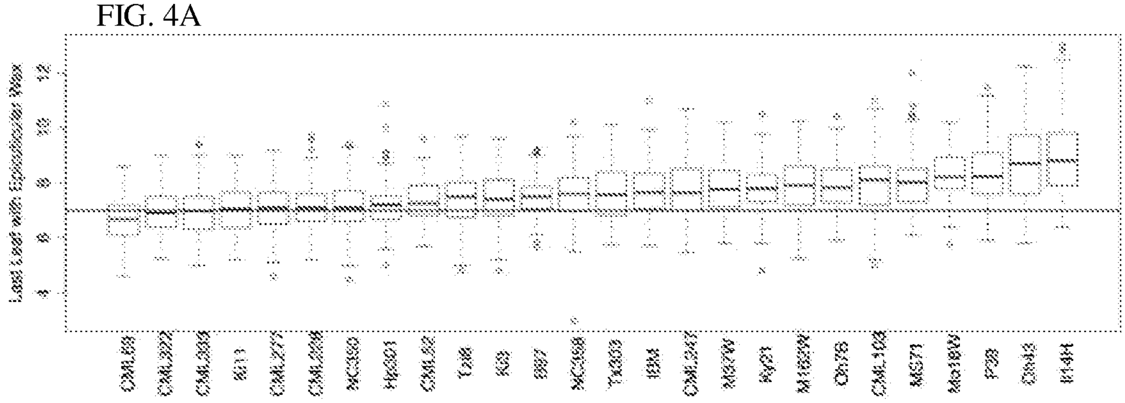
FIG. 4 depicts bar plots showing variation of transition leaf numbering. (A) Variation for transition leaf by NAM family, labeled by the non-B7 parent on top. The horizontal line at leaf 7 represents the average transition leaf for B73; (B) Phenotypic distribution of the last leaf with epicuticular wax in the NAM population. Leaf number distribution ranged from leaf 4.5 to leaf 13.25; (C) Phenotypic variation for transition leaf in the IBM, NYH, OWRI, and Wisconsin diversity panel populations (plots i-iv, respectively).
Figure 4B:
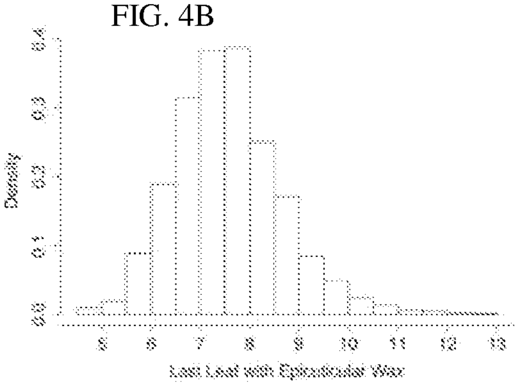
Figure 4C:
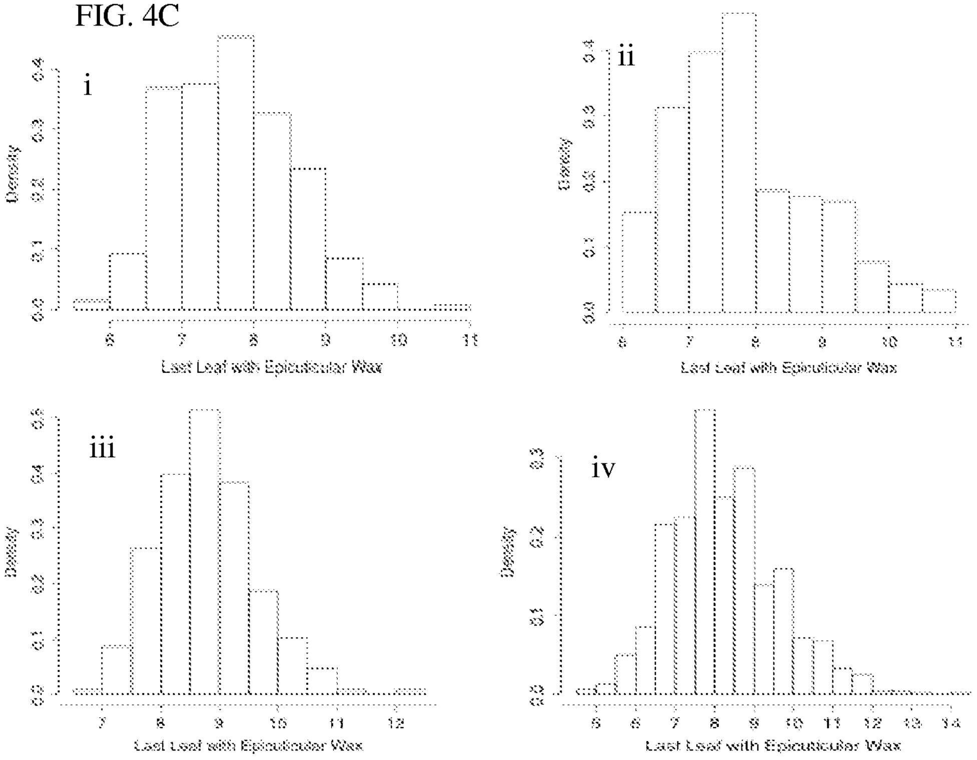

The molecular network controlling the process of developmental transition has been poorly understood. The present study utilizes the dramatic variation in the timing of juvenile to adult vegetative transition in different maize populations to identify genes and pathways controlling this fundamental biological process. This work evaluates structured populations and diverse collections of maize that have been characterized extensively for allelic variation, for instance at the GRMZM2G362718 locus, in order to provide a genetic basis for the extensive observed natural variation for developmental timing in plants such as maize. Exemplary phenotypic variation for timing of production of a transition leaf in the maize NAM population is provided in FIG. 4A-4C, with variation for transition leaf by NAM family, labeled by the non-B7 parent in FIG. 4A. The horizontal line at leaf 7 represents the average transition leaf for B73. Phenotypic distribution of the last leaf with epicuticular wax in the NAM population is shown in FIG. 4B. Transition leaf number distribution ranged from leaf 4.5 to leaf 13.25. Phenotypic variation for transition leaf in the IBM, NYH, OWRI, and Wisconsin diversity panel populations is shown in FIG. 4C, plots i-iv.

QTL discovery was accomplished by analysis of a collection of structured biparental mapping populations and a diversity panel of maize inbred lines (summarized in FIG. 5). These included the publicly available Nested Association Mapping (NAM) resource (Flint-Garcia et al *Plant J* 44(6): 1054-64, 2005) and the intermated B73×Mo17 (IBM) RIL mapping population (Lee et al., *Plant Mol Biol* 48(5-6):453-61, 2002). In addition, Oh43×W64A (OWRI) and Ny821×H99 (NyH) populations were evaluated. The diversity panel included a set of northern adapted inbreds described by Hansey et al (*Bioenergy Res.* 3:28-37, 2010) plus 512 lines released by CIMMYT (International Maize and Wheat Improvement Center; Texcoco, Mexico) that are of tropical, subtropical, and highland origin. In total, 5779 unique genotypes were evaluated in at least one location and season, with many of the materials replicated across years.

Example 2

Phenotypic Analysis

The primary trait that was scored to reflect the timing of juvenile to adult transition was the last leaf with juvenile wax (FIG. 1). Maize leaves, in order of emergence, can be fully juvenile, part juvenile and part adult (termed transition leaves), and fully adult. Since the earliest emerging juvenile leaves can senesce and become no longer visible at the time that the uppermost transition leaf can be scored, leaf 5 was marked at the young seedling stage (~V7) by punching a hole in the leaf with a leaf punch. At the ~V10 stage, a paper collar was secured around the stalk between leaf 8 and 9 to mark that internode before the punched leaf 5 fully senesced. The last leaf with juvenile wax was scored on 5 plants per plot with the exact node from which it emerged determined by the position of the leaf collar. At flowering time or thereafter, the total number of leaves (nodes) was determined by counting 5 plants per plot. Node number is both a measure of the duration of plant development (highly correlated with flowering time), but also allowing for calculation of the proportion of nodes which were juvenile versus adult. Days to pollen shed and days to silk emergence were scored by visual assessment of the day that 50% or greater of the plants in a plot had visible pollen shed and visible silk emergence, respectively.

The following linear model was used for phenotypic analysis of the NAMs:

$$Y_{ik}{\sim}G+Y_k+e_{ik}$$

where Y is the last leaf with epicuticular wax of the ith genotype (G) in the kth year (Y) and μ is the overall mean with residual error $e_{ik}$. All effects were considered random.

Repeatability in the NAM, NyH, and OWRI populations were calculated as:

$$R^2 = \frac{\sigma^2(G)}{\sigma^2(E) + \sigma^2(G)}$$

where $\sigma^2$(G) is the genotypic variance and $\sigma^2$(E) is the error variance.

The following linear model was used for phenotypic analysis of the IBM, NyH and OWRI populations as well as the Wisconsin Diversity Panel:

$$Y_{ijk} \sim \mu + G_i + R_{j(k)} + Y_k + Y_k \times G_i + e_{ijk}$$

where Y is the last leaf with epicuticular wax of the ith genotype (G) in the jth rep (R) within the kth year (Y) and μ is the overall mean. All effects were considered random.

Heritability on an entry mean basis was calculated in the IBM population and the WiDiv panel using the following formula:

$$H^2 = \frac{\sigma^2(G)}{\frac{\sigma^2(E)}{ry} + \frac{\sigma^2(GY)}{r} + \sigma^2(G)}$$

where $\sigma^2$(G) is the genotypic variance, $\sigma^2$(GY) is the genotype by year variance and $\sigma^2$(E) is the error variance.

Significant Pearson and Spearman rank correlations between years were calculated and allowed analysis of averages across years. Following correlation analysis, means across years (and replications for the IBM, NyH, and OWRI populations) were used for QTL mapping. Phenotypic Pearson correlations were performed for transition and flowering time, node number, and internode length.

Example 3

QTL Analysis and Integration of QTL Results Across Materials

1. Nested Association Mapping (NAM) Population:

1106 single nucleotide polymorphisms (SNPs) markers on the 3875 NAM lines (Buckler et al., *Science* 325:714-718, 2009) were used for composite interval mapping with Windows QTL Cartographer v2.5 (Wang, http://statgen.ncsu.edu/qtlcart/WQTLCart.htm, 2011). One thousand permutations were performed to determine an appropriate significance threshold.

QTL were then mapped in a combined analysis of all 25 NAM populations by joint stepwise regression of transition leaf on the same 1106 SNP makers. Because stepwise regression cannot use individuals with missing marker data, an initial step was to impute missing markers. In the joint stepwise regression, a population and marker by population effect was fit. Using the SAS experimental procedure, GLMSELECT, covariates were determined by forward regression (p=0.0001) and SQL was subsequently used to calculate a likelihood ratio for all markers, as per Buckler et al (2009), to determine a genome-wide error rate of 12.26 by permutation.

The 1.6 million SNPs identified in the HapMap project were imputed in the offspring of the NAM RILs based on founder genotypes. Genome wide association was conducted on top of the joint linkage mapping from above. First, residuals for each chromosome were calculated from the full joint linkage model and with the removal of any QTL located on that chromosome. Single marker analysis was then performed on the residuals across all 1.6 million SNPs to determine significance at each locus. A threshold was also set using 1000 permutation scans.

The last leaf with epicuticular wax varied in the NAM RILs ranging from leaf 4.5 to leaf 13.25 with a repeatability of 0.72. The phenotypic distribution of the NAM families in FIG. 4 shows the trait centering near leaf 7, which is the average transition leaf of B73 and the common parent among the NAMs. Although node number is highly correlated with flowering time, transition leaf was not found to be correlated with flowering time, node number, or internode length with Pearson correlation coefficients of −0.18, −0.10, and 0.07 respectively in the NAM populations.

Through single-population composite interval mapping, 56 total QTL were detected across all NAM populations. A QTL on the long arm of chromosome two in bin ten was detected in 22 of the 25 NAM populations explaining between 5-55% of the variation. The LOD scores ranged from 6.4 to 32.9, while the significance threshold was 2.5.

Similar QTL were detected with the joint-linkage composite interval mapping. The major QTL located on chromosome two had LOD scores of 303.9. The combined average additive effects of the three most significant QTL equate to almost a three-leaf difference in transition, or near 40% of the variation observed in the NAM population. Interestingly, the additive effect of all non-B73 alleles at the chromosome two QTL extends the juvenile wax phase compared to B73.

Figure 6A:
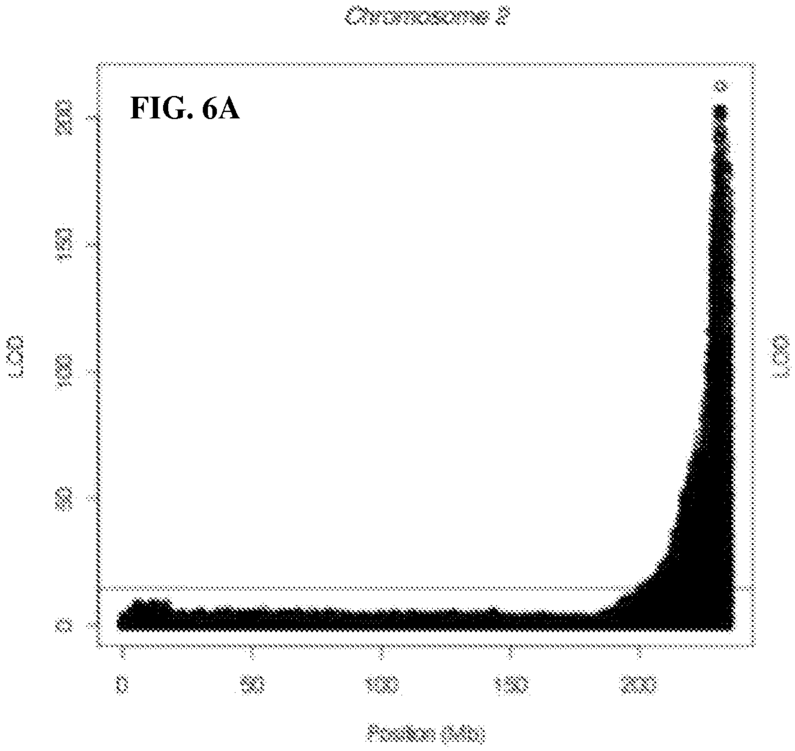
FIG. 6 shows genome wide association results with 1.6 million polymorphic markers across the NAM population. (A) Position of significant QTL found on the long arm of chromosome 2.; (B) sub sampling analysis confirming location of QTL on chromosome 2. Dashed line represents F-test log(1/P) in the final joint linkage model. Vertical position of points represents bootstrap posterior probability (BPP) of the SNP.
Figure 6B:
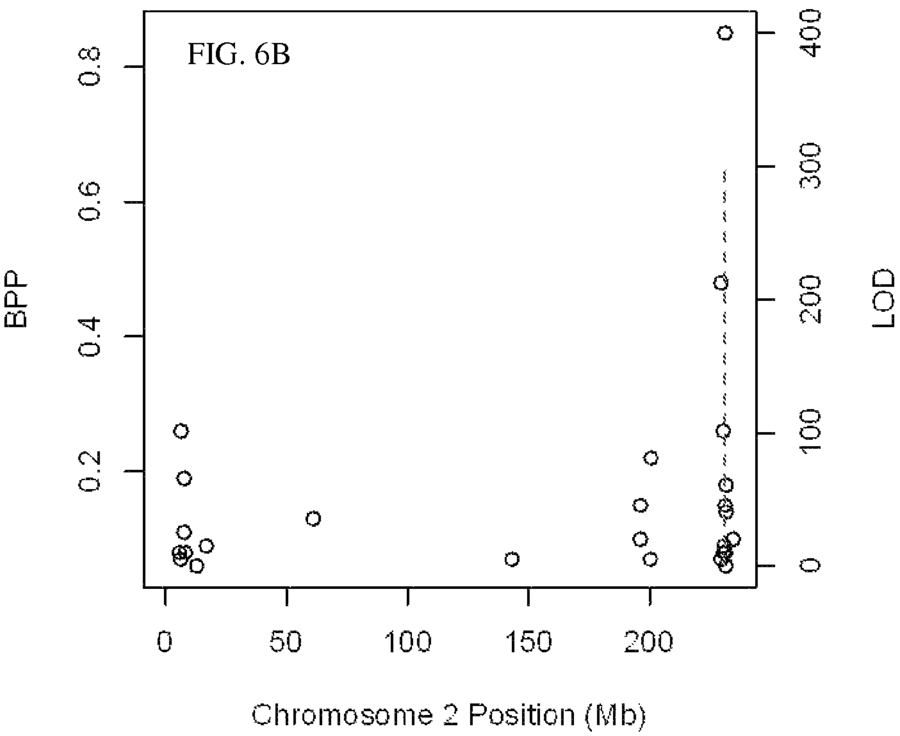

Using the genome-wide association scan, the most significant SNP is located at 234,407,421 on chromosome two (FIG. 6A) reaching a maximum LOD score of 212.4. FIG. 6B shows results of chromosome two from a similar genome-wide analysis using sub sampling. The results are in agreement with the single marker genome wide scan; the most significant SNP is at position 234,407,421 on chromosome two.

2. Intermated B73×Mo17, Ny821×H99, and Oh43×W64A Populations:

1340 markers on the recombinant inbred lines of the IBM population (Lee et al *Plant Mol Biol* 48(5-6):453-61, 2002), 78 markers on the NyH RILs, and 169 markers on the OWRI RILS were used for composite interval mapping with Windows QTL Cartographer v2.5 (Wang, 2011). One thousand permutations were performed to determine an appropriate significance threshold. Updated genetic maps of these populations are developed with over 1480 SNP markers identified through genotyping-by-sequencing, and composite interval mapping of transition leaf is analyzed. The increased marker density improves the precision of QTL detection in these populations.

The last leaf with epicuticular wax ranged from leaf 5.4 to 11 in the IBM RILs, from 4.6 to 14.2 in the diversity panel with a heritability of 0.53, 0.6 respectively. The NyH population ranged in transition from leaf 6 to 11 and from leaf 6.9 to 12.2 in the OWRI population (FIG. 4).

The same QTL on chromosome two detected in 23 NAM populations was also detected in the IBM population, having a LOD score of 18.7. This QTL explains 16% of the variation in the IBM population.

Four QTL were detected in the NyH mapping population, one located on chromosome 2. The QTL on chromosome 2 is consistent with the chromosome 2 QTL detected in NAM and IBM. This QTL explains 11.6% of the variation observed in the NyH population.

3. Wisconsin Diversity Panel (WiDiv):

Over 100,000 SNPs have been identified in this diversity panel through genotyping-by-sequencing (Elshire et al *PLoS One* 6(5): e19379, 2011). Association analysis including appropriate kinship and population structure matrices is performed; and genome-wide association analysis of transition leaf is analyzed on the WiDiv data set.

A summary of all QTL mapping results can be found in Table 1. Numbers indicate LOD score. Overlapping QTL based on the physical position of QTL support intervals are italicized. NAM QTL are presented from joint-linkage composite interval mapping (LOD threshold 12.26). IBM, NyH, and OWRI results are from composite interval mapping (LOD threshold 2.5).

TABLE 1

Summary of QTL detected across all RIL mapping populations. Numbers indicate LOD score. Overlapping QTL based on physical position of QTL support intervals are italicized.

| Mapping Population | LOD score of QTL on chromosome 2 |
|---|---|
| NAM | 21.3, 20.1, 18.2, *303.9* |
| IBM | *18.7* |
| NyH | *3.3* |

Two common QTL were detected across multiple mapping populations. The QTL on the long arm of chromosome two was detected in NAM, IBM, and NyH populations. No previously known genes affecting vegetative phase change or miRNA targets are located in the chromosome two QTL peak.

The putative chromosome two peak was initially defined as covering a 1.1 Mb region containing over 50 predicted gene models (MaizeGDB; world wide web maizegdb.org). However, the most significant polymorphism from 1.6 million loci, was narrowed to a single SNP at position 234,407,421 on chromosome two (AGP_v2). These results demonstrate that a major QTL on chromosome 2 underlies natural variation for this important developmental trait of juvenile-adult transition.

Example 4

Candidate Gene GRMZM2G362718

The gene model nearest the most significant SNP on chromosome two is GRMZM2G362718 whose predicted protein contains a DNMT1 and PHD-finger domain. A protein BLAST shows this gene is highly similar to the enhanced downy mildew 2 (EDM2-encoding) transcription factor of *Arabidopsis*, rice, *Brachypodium*, and sorghum (52.9, 56.7, 42.9, 63.2, percent similarity respectively).

Although the function of GRMZM2G362718 is unknown, several known functions of EDM2 in other species point to its potential significance in underlying the chromosome two QTL. Mutations in EDM2 show a delay in flowering and elevated transcripts of the flowering suppressor FLC (Tsuchiya and Eulgem *Plant. J.* 62:518-528, 2010). These authors reported EDM2's function in regulating the vegetative to floral transition in an FLC-dependent manner; EDM2 also has a direct effect on the juvenile to adult vegetative phase change in *Arabidopsis*.

edm2 plants appear to skip the early juvenile phase of development by not producing the initial pair of rosette leaves. The effect of edm2-2 on trichome production was also examined by these authors. In wild-type *Arabidopsis*, juvenile leaves lack trichomes on the abaxial side, while adult leaves gradually produce an increasing number of trichomes. Mutant edm2-2 plants delay the onset of trichome production and, therefore, EDM2 seems to have a role in promoting the transition from the juvenile to adult vegetative phase (Tsuchiya and Eulgem *BMC Plant Bio.* 10:203-217, 2010). Further, Willmann and Poethig (*Devel.* 138:677-685, 2011) show FLC has both flowering-dependent and flowering-independent effects on vegetative transition. EDM2 does not appear to affect expression of the trans-acting siRNAs (HASTY, ZIPPY, SGS3, RDR6) or the other five genes (ARF3, ARF4, SPL3, At1g63130, At5g18040) of this pathway that have previously been shown to control vegetative phase change in *Arabidopsis* (Peragine et al *Genes Devel.* 18:2368-2379, 2004). This suggests EDM2's role in vegetative phase change may be independent of the siRNA pathway, and GRMZM2G362718 may act similarly.

Sekhon et al (*Plant J.* 66:553-563, 2011) developed a maize B73 gene atlas showing gene expression levels across all 11 major organs at varying developmental time points (60 total tissue samples). The atlas shows some level of GRMZM2G362718 expression in all tissue sampled, such as a pooled leaf sample as well as in tissue at the base of stage two leaves and immature leaves (v9). Neighboring gene models 500 kb up and downstream of GRMZM2G362718 were therefore studied in the gene atlas to determine if any could be ruled out as candidates due to inappropriate tissue expression. All predicted neighboring gene models were either not present in the atlas data set or were expressed at some level in the shoot apical meristem.

RNA-seq expression levels on a subset of the Wisconsin diversity panel (Hansey et al *PLos ONE* 7(3):e33071, 2011) were thus used to determine if a relationship exists between expression of GRMZM2G362718 and timing of vegetative phase change. In this analysis, diverse inbreds were ordered from early to late transition and their gene expression pattern is plotted. Either categorical differences (i.e. as shown by groups of early or late transitioning inbreds have a shared expression level), or quantitative differences (i.e. via a progressive increase or decrease in expression level trending with timing of phase change) would indicate a relationship between the expression of GRMZM2G362718 and phenotype. Analysis of RNA-seq information is performed to demonstrate such differences.

Figure 7:
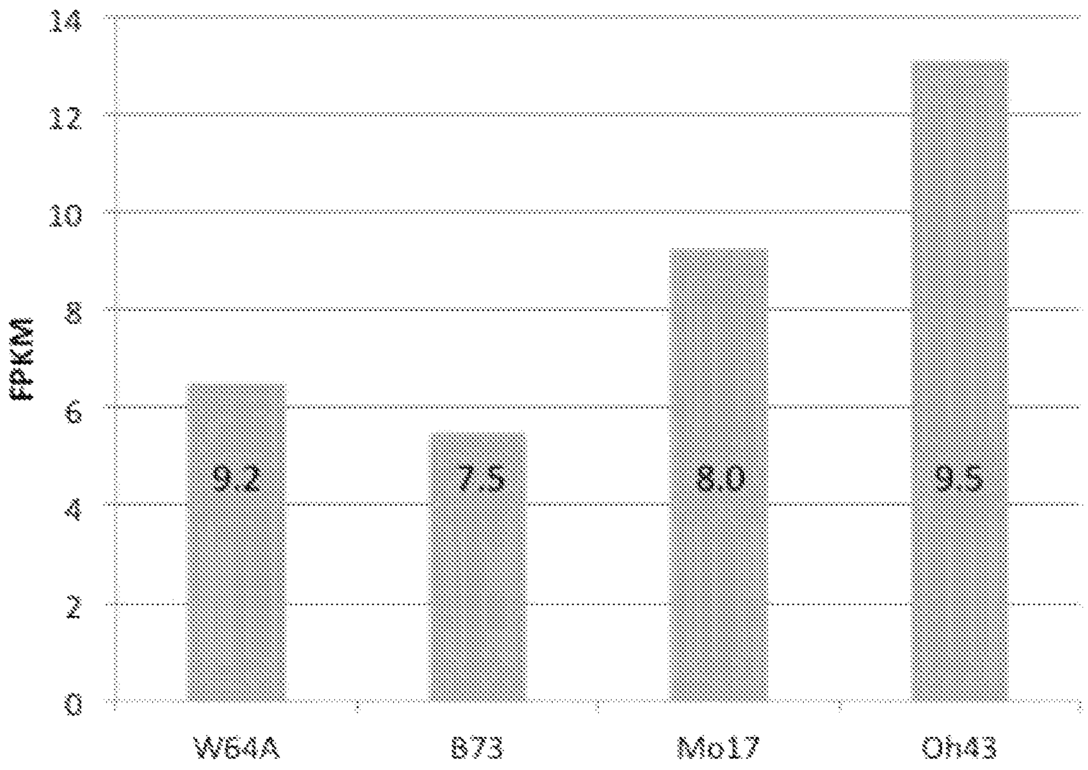
FIG. 7 depicts RNA sequence expression data of GRMZM2G362718 for four maize inbred lines that are parents of RIL mapping populations (Oh43×W64A; B73×Mo17; B73×Oh43). The inbred's transition phenotype is displayed numerically within the bar.

Specific allelic contrasts between B73, Mo17, Oh43, and W64A show some association whereby later transitioning plants displayed higher expression levels of GRMZM2G362718 (FIG. 7). For example, B73 has an average transition leaf of 7.5 and an expression level of 5 fragments per kilobase per million reads (FPKM) compared to Oh43 which transitions at leaf 9.5 on average, and has an expression level of 13 FPKM. In this comparison, the later transition corresponds with a higher expression level. However the comparison is between plants with different GRMZM2G362718 alleles which may differ in function or activity, and thus correlating function and expression level may not be straightforward. It is also important to consider the tissue sampled (whole seedling) when making these comparisons; thus further expression analysis of the shoot apical meristem at various developmental time points is performed.

Example 5

Candidate Gene Glossy 15

Figure 8:
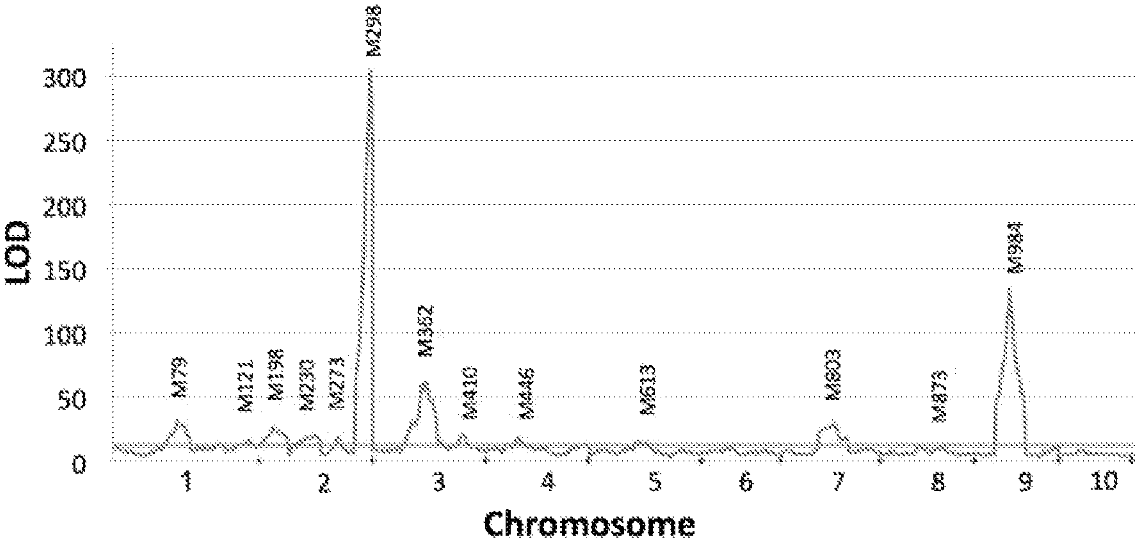
FIG. 8 depicts LOD scores for detecting the presence of QTL located on any of chromosomes 1-10. Stepwise regression with covariates was used in joint QTL mapping of all NAM populations with a threshold value of 12.26 (Buckler et al., *Science* 325:714-718, 2009).

QTL mapping performed with the NAM population detected three major QTL located on chromosomes two, three, and nine, which had LOD scores of 303.9, 87.5 and 141.2 respectively (FIG. 8). The gene model nearest the most significant SNP on chromosome nine is Glossy 15 ("Gl15" (GRMZM2G160730); e.g. Moose and Sisco, *Genes Dev.* 10:3018-3027, 1996). Glossy15 encodes an AP2-like transcription factor which is responsible for the expression of adult traits in the leaf epidermis. Additional mapping populations were also analyzed. Based on overlapping LOD confidence intervals, the QTL detected on chromosomes 2 and 9 after composite interval mapping of the IBM population are consistent with the QTL detected in the NAM population. For the Wisconsin Diversity Panel population a mixed linear model including relatedness and population structure was used to perform a genome wide association study. After an experiment wide Bonferroni correction for multiple tests, one genomic region was significantly associated with changes in the production of the last juvenile leaf ("LJL") and was located on chromosome nine with an additive effect of −0.43, relative to the minor allele. The most significant SNPs in this region are located within the gene Glossy15.

Glossy15 is thus a candidate gene, modulation of expression or activity of which can result in altering the timing of juvenile to adult phase change in plants. For instance, Glossy15 may be utilized in conjunction with GRMZM2G362718, and/or GRMZM2G096016 (see Example 6), to modulate, e.g. delay, the transition of a plant from a juvenile to an adult phase of growth.

Example 6

Candidate Gene GRMZM2G096016

Sequencing of whole seedling RNA was conducted from a set of 503 diverse maize inbred lines to evaluate the maize seedling pan-transcriptome as a proxy to the maize pan genome. Using de novo assembly of reads unmapped to the B73 reference genome, 8,681 novel representative transcript assemblies (RTAs) were identified. Genomic Presence/Absence Variation Analysis was performed, and pooled reads were cleaned using the fastx_clipper program within the FASTX toolkit. The minimum sequence length was set to 15 bp after clipping using both Illumina single end adapter sequences. Sequence reads were parsed into individual genotype files requiring a perfect match to the barcode and ApeKI cut site, and the barcode sequences were removed. Sequence reads were mapped to AGPv2 using Bowtie version 0.12.7 (Langmead, *Genome Biol.* 10:R25, 2009) requiring a unique alignment and allowing up to two mismatches. SAMtools version 0.1.7 (Li et al., *Bioinformatics* 25:2078-2079, 2009) was used to generate unfiltered pileup files. Representative genes/RTAs with at least two uniquely aligned reads were considered present at the genome level.

Sequence reads for each library were mapped to an AGPv2 formatted maize reference genome plus the 8,681 unfiltered RTAs using Bowtie version 0.12.7 (Langmead, 2009, ibid) and TopHat version 1.4.1 (Trapnell et al., *Nature Protocols* 7:562-578, 2012). Normalized gene expression levels were determined using Cufflinks version 1.3.0 (Trapnell, ibid). To characterize transcript presence/absence variation (PAV), sequence reads were also mapped to AGPv2 plus the 8,681 unfiltered RTAs requiring a unique alignment. A gene/RTA was then defined as expressed if the fragments per kilobase of exon model per million fragments mapped (FPKM) low confidence interval as described by Cufflinks was greater than zero. The 503 included inbred lines were clustered with hierarchical clustering using a Pearson correlation distance metric and average linkage using Multiple Experiment Viewer Software (MeV) version 4.5 (Saeed et al., *Biotechniques* 34:374-378, 2003).

Vegetative phase change was scored by identifying the last leaf with epicuticular wax in a subset of the 503 inbred lines. Significant natural variation for the last juvenile leaf was observed, ranging from leaf 3.45 to leaf 13.4. 186,733 SNPs were subjected to genome wide association analysis (GWAS) which was performed using a mixed linear model accounting for both familial relatedness (Q) and population structure (K) (Yu et al., *Nature Genetics* 38:203-208, 2006). GWAS was also performed with transcript presence/absence state for all of the reference genes and RTAs for last juvenile leaf. The association analysis was done using the same mixed model as described above but instead of using a SNP as the dependent variable, transcript presence/absence was used as the genetic marker. In the presence/absence analysis, GRMZM2G096016 (GenBank EU975023.1) which encodes predicted nuclear transcription factor Y-subunit A-10, was found to be significantly associated with regulation of the timing of vegetative phase change transition, and may be utilized to modulate, e.g. delay, the transition of a plant from a juvenile to an adult phase of growth.

What is claimed is:

1. A polynucleotide molecule comprising a nucleotide sequence selected from the group consisting of:

(a) a nucleotide sequence encoding a polypeptide that comprises an amino acid sequence that is at least 96% identical over its full length to the amino acid sequence of SEQ ID NO: 17; wherein the polypeptide regulates juvenile to adult phase change in grass plant leaves;

(b) a nucleotide sequence comprising SEQ ID NO: 16;

(c) a nucleotide sequence comprising at least 95% sequence identity over its full length to the full length of SEQ ID NO:16, wherein the nucleotide sequence encodes a protein that regulates juvenile to adult phase change in grass plant leaves; and (d) the nucleotide sequence complementary to (a), (b), or (c), wherein the polynucleotide molecule further comprises a heterologous promoter functional in plants that is operably linked to the nucleotide sequence.

2. The polynucleotide molecule of claim 1, wherein the nucleotide sequence comprises SEQ ID NO:16.

3. A recombinant vector comprising the polynucleotide molecule of claim 1.

4. The recombinant vector of claim 3, further comprising at least one additional sequence chosen from the group consisting of: a regulatory sequence, a selectable marker, a leader sequence and a terminator.

5. The recombinant vector of claim 4, wherein the additional sequence is a heterologous sequence.

6. The recombinant vector of claim 3, wherein the promoter is a tissue-specific promoter.

7. The recombinant vector of claim 3, wherein the promoter directs expression in leaf tissue.

8. The recombinant vector of claim 3, defined as an isolated expression cassette.

9. A recombinant vector construct comprising a polynucleotide sequence encoding a siRNA that targets a nucleotide sequence, wherein expression of the siRNA in a plant down regulates expression of the nucleotide sequence, wherein the nucleotide sequence is selected from the group consisting of:

(a) a nucleotide sequence encoding a polypeptide that comprises an amino acid sequence that is at least 95% identical over its full length to the amino acid sequence of SEQ ID NO: 17; wherein the polypeptide regulates juvenile to adult phase change in grass plant leaves;

(b) a nucleotide sequence comprising SEQ ID NO: 16;

(c) a nucleotide sequence comprising at least 95% sequence identity over its full length to the full length of SEQ ID NO:16, wherein the nucleotide sequence encodes a protein that regulates juvenile to adult phase change in grass plant leaves; and (d) the nucleotide sequence complementary to (a), (b), or (c).

10. A transgenic plant comprising a recombinant vector, the recombinant vector comprising a heterologous promoter functional in plants that is operably linked to a nucleotide sequence selected from the group consisting of:

(a) a nucleotide sequence encoding a polypeptide that comprises an amino acid sequence that is at least 95% identical over its full length to the amino acid sequence of SEQ ID NO: 17; wherein the polypeptide regulates juvenile to adult phase change in grass plant leaves;

(b) a nucleotide sequence comprising SEQ ID NO: 16;

(c) a nucleotide sequence comprising at least 95% sequence identity over its full length to the full length of SEQ ID NO:16, wherein the nucleotide sequence encodes a protein that regulates juvenile to adult phase change in grass plant leaves; and (d) the nucleotide sequence complementary to (a), (b), or (c).

11. A transgenic plant comprising the recombinant vector construct of claim 9.

12. The transgenic plant of claim 10, further defined as a monocotyledonous plant.

13. The transgenic plant of claim 10, further defined as a member of the Poaceae, the Panicoideae or the Pooideae.

14. The transgenic plant of claim 10, further defined as maize, rice, sorghum, or switchgrass.

15. A seed of the transgenic plant of claim 10, wherein the seed comprises the recombinant vector.

16. The transgenic plant of claim 10, wherein the last leaf with epicuticular wax is produced later during plant development relative to that found in an otherwise isogenic plant lacking the recombinant vector.

17. A cell transformed with the recombinant vector of claim 3.

18. A method of altering the timing of juvenile to adult phase change in a plant, the method comprising expressing the construct of claim 3 in the plant or expressing the construct of claim 9 in the plant.

19. The method of claim 18, wherein the timing of juvenile to adult phase change is calculated by a method comprising counting the last leaf displaying epicuticular wax.

20. The method of claim 18, wherein the plant exhibits an altered trait selected from the group consisting of: an increase of at least one in the numbering of the last leaf which displays epicuticular wax or which does not contain abaxial trichomes; an altered proportion of juvenile, transitional, or adult leaves; enhanced yield of vegetative tissue; enhanced digestibility of vegetative tissue; enhanced resistance to a plant pest; and enhanced resistance to a plant disease, wherein the trait exhibited by the plant is altered relative to a wild type plant.

21. The method of claim 18, wherein the plant has altered development or morphology when compared to a wild type plant, further wherein the plant displays an altered trait selected from the group consisting of: enhanced disease resistance, enhanced insect resistance, improved forage digestibility, enhanced abiotic stress tolerance, and improved utility for biofuel production, wherein the development, morphology, or trait is altered relative to a wild-type plant.

22. A method of producing plant biomass, the method comprising:

(a) obtaining a plant according to claim 10; and (b) preparing biomass from said plant or a part thereof.

23. The method of claim 22, further comprising producing biofuel, food or feed from the biomass.

24. The recombinant vector of claim 3, further comprising an additional polynucleotide sequence that encodes all or part of a sequence of Glossy15 or Cg1.

25. The recombinant vector of claim 9, further comprising an additional polynucleotide sequence which, after being transcribed, regulates the timing of the juvenile to adult phase change in a plant.

26. A transgenic plant comprising the recombinant vector of claim 3.

27. A transgenic plant comprising the recombinant vector of claim 25.

28. A seed of the transgenic plant of claim 26 wherein the seed comprises the recombinant vector.

29. The method of claim 18, further comprising modulating the expression of at least a second gene which regulates the timing of the juvenile to adult phase change in a plant.

30. The method of claim 29, wherein the second gene is selected from the group consisting of: Glossy15 and Cg1.

31. The method of claim 29, wherein the timing of juvenile to adult phase in the plant is extended relative to a wild type plant.

32. The polynucleotide molecule of claim 1, wherein the nucleotide sequence encodes a polypeptide that comprises an amino acid sequence that is at least 99% identical over its full length to the amino acid sequence of SEQ ID NO: 17.

33. The polynucleotide molecule of claim 1, wherein the nucleotide sequence comprises at least 95% sequence identity over its full length to the full length of SEQ ID NO:16.

* * * * *